(12) United States Patent
Hartmann et al.

(10) Patent No.: US 8,546,392 B2
(45) Date of Patent: Oct. 1, 2013

(54) 17BETA-HYDROXYSTEROID DEHYDROGENASE TYPE 1 INHIBITORS FOR THE TREATMENT OF HORMONE-RELATED DISEASES

(75) Inventors: Rolf Hartmann, Saarbrücken (DE); Martin Frotscher, Sulzbach (DE); Sandrine Oberwinkler, Blieskastel (DE); Erika Ziegler, Völklingen (DE); Josef Messinger, Hannover (DE); Heinrich-Hubert Thole, Hannover (DE)

(73) Assignee: Universitaet des Saarlandes, Saarbruecken (DE)

( * ) Notice: Subject to any disclaimer, the term of this patent is extended or adjusted under 35 U.S.C. 154(b) by 86 days.

(21) Appl. No.: 12/593,134

(22) PCT Filed: Mar. 27, 2008

(86) PCT No.: PCT/EP2008/053672
§ 371 (c)(1),
(2), (4) Date: Apr. 15, 2010

(87) PCT Pub. No.: WO2008/116920
PCT Pub. Date: Oct. 2, 2008

(65) Prior Publication Data
US 2010/0204234 A1 Aug. 12, 2010

(51) Int. Cl.
| | | |
|---|---|---|
| *A61K 31/5375* | (2006.01) | |
| *A61K 31/192* | (2006.01) | |
| *A61K 31/405* | (2006.01) | |
| *A61K 31/47* | (2006.01) | |
| *A61K 31/505* | (2006.01) | |
| *C07C 65/24* | (2006.01) | |
| *C07C 59/40* | (2006.01) | |
| *C07D 209/12* | (2006.01) | |
| *C07D 215/14* | (2006.01) | |
| *C07D 239/26* | (2006.01) | |
| *C07D 265/30* | (2006.01) | |

(52) U.S. Cl.
USPC ........ 514/238.8; 514/569; 514/415; 514/311; 514/256; 544/173; 544/335; 546/173; 548/509; 562/466; 562/469

(58) Field of Classification Search
None
See application file for complete search history.

(56) References Cited

U.S. PATENT DOCUMENTS

| 1,181,485 A | 5/1916 | Schwabe |
| 2005/0038053 A1 | 2/2005 | Hirvelae |
| 2005/0228038 A1 | 10/2005 | Vander Jagt et al. |

FOREIGN PATENT DOCUMENTS

| EP | 0 702 962 | 3/1996 |
| WO | 99 12540 | 3/1999 |
| WO | 03 051805 | 6/2003 |
| WO | 2004 110459 | 12/2004 |
| WO | 2005 014551 | 2/2005 |
| WO | 2005 047303 | 5/2005 |
| WO | 2006 003012 | 1/2006 |
| WO | 2006045096 | 4/2006 |
| WO | WO 2007067612 A1 * | 6/2007 |
| WO | 2007 095286 | 8/2007 |

OTHER PUBLICATIONS

STN_12593134_preliminary_(2011).*
CAS RN 201415-78-3, entering STN database on Feb. 17, 1998.*
Frotscher et al., Journal of Medicinal Chemistry (2008), vol. 51(7), p. 2158-2169.*
Smyth et al.; "Hydrocylated 2-(5'Salicyl)naphthalenes as Protein-Tyrosine Kinase Inhibitors"; J. Med. Chem. 1993, 36, pp. 3015-3020.
Raychaudhuri; "Biaryls and related compounds: a single step synthesis from cyclohexenone derivatives"; Chemistry and Industry, Apr. 5, 1980, p. 293-294.
Bass; "A new route to 6-hydroxyquinoline-4-carboxylic acids"; Chemistry and Industry, Sep. 1, 1973; p. 849.
Gillman et al; "Some Organolithium Compounds of Quinoline and 2-Phenylquinoline"; J. Organic Chemistry, vol. 23, pp. 1584-1585, Oct. 1958.
Kovács et al;"Beitrag zur synthese der Tetrahydroisochinolin-alkaloide unter physiologischen bedingungen"; Chem. Ber. 1951, No. 9, p. 795-801.
Kovács et al; "Preparation of some new quinoxaline derivatives"; Acta Univ. Szeged., Chem et Phys., 1950, 3, pp. 35-37.
Holdsworth et al; "Derivatives of 2-phenyl quinoline part III"; Journal and Proceedings of the Royal Society of New South Wales, 1933, 66, pp. 473-476.

* cited by examiner

*Primary Examiner* — Yong Chu
(74) *Attorney, Agent, or Firm* — Norris, McLaughlin & Marcus, P.A.

(57) ABSTRACT

The invention relates to the use of non-steroidal 17beta-hydroxysteroid dehydrogenase type 1 inhibitors for the treatment and prophylaxis of hormone-dependent, particularly estrogen-dependent, diseases. The invention further relates to suitable inhibitors and to a method for the production thereof.

8 Claims, No Drawings

17BETA-HYDROXYSTEROID DEHYDROGENASE TYPE 1 INHIBITORS FOR THE TREATMENT OF HORMONE-RELATED DISEASES

This application is a 371 of PCT/EP2008/053672, filed Mar. 27, 2008, which claims foreign priority benefit under 35 U.S.C. §119 of the German Patent Application No. 10 2007 015 169.3 filed Mar. 27, 2007.

The invention relates to the use of non-steroidal 17beta-hydroxysteroid dehydrogenase type 1 (17betaHSD1) inhibitors for the treatment and prophylaxis of hormone-related, especially estrogen-related, diseases. Further, suitable inhibitors and a process for the preparation thereof are provided.

BACKGROUND OF THE INVENTION

Steroid hormones are important chemical carriers of information serving for the long-term and global control of cellular functions. They control the growth and the differentiation and function of many organs. On the other hand, they may also have negative effects and favor the pathogenesis and proliferation of diseases in the organism, such as mammary and prostate cancers (Deroo, B. J. et al., J. Clin. Invest., 116: 561-570 (2006); Fernandez, S. V. et al., Int. J. Cancer, 118: 1862-1868 (2006)).

The biosynthesis of steroids takes place in the testes or ovaries, where sex hormones are produced. In addition, the production of glucocorticoids and mineral corticoids takes place in the adrenal glands. Moreover, individual synthetic steps also occur outside the glands, namely in the brain or in the peripheral tissue, e.g., adipose tissue (Bulun, S. E. et al., J. Steroid Biochem. Mol. Biol., 79: 19-25 (2001); Gangloff, A. et al., Biochem. J., 356: 269-276 (2001)). In this context, Labrie coined the term "intracrinology" in 1988 (Labrie, C. et al., Endocrinology, 123: 1412-1417 (1988); Labrie, F. et al., Ann. Endocrinol. (Paris), 56: 23-29 (1995); Labrie, F. et al., Horm. Res., 54: 218-229 (2000)). Attention was thus focused on the synthesis of steroids that are formed locally in peripheral tissues and also display their action there without getting into the blood circulation. The intensity of the activity of the hormones is modulated in the target tissue by means of various enzymes.

Thus, it could be shown that the 17β-hydroxysteroid dehydrogenase type 1 (17β-HSD1), which catalyzes the conversion of estrone to estradiol, is more abundant in endometriotic tissue and breast cancer cells while there is a deficiency in 17β-HSD type 2, which catalyzes the reverse reaction (Bulun, S. E. et al., J. Steroid Biochem. Mol. Biol., 79: 19-25 (2001); Miyoshi, Y. et al., Int. J. Cancer, 94: 685-689 (2001)).

A major class of steroid hormones is formed by the estrogens, the female sex hormones, whose biosynthesis takes place mainly in the ovaries and reaches its maximum immediately before ovulation. However, estrogens also occur in the adipose tissue, muscles and some tumors. Their main functions include a genital activity, i.e., the development and maintenance of the female sexual characteristics as well as an extragenital lipid-anabolic activity leading to the development of subcutaneous adipose tissue. In addition, they are involved in the pathogenesis and proliferation of estrogen-related diseases, such as endometriosis, endometrial carcinoma, adenomyosis and breast cancer (Bulun, S. E. et al., J. Steroid Biochem. Mol. Biol., 79: 19-25 (2001); Miyoshi, Y. et al., Int. J. Cancer, 94: 685-689 (2001); Gunnarsson, C. et al., Cancer Res., 61: 8448-8451 (2001); Kitawaki, J., Journal of Steroid Biochemistry & Molecular Biology, 83: 149-155 (2003); Vihko, P. et al., J. Steroid. Biochem. Mol. Biol., 83: 119-122 (2002); Vihko, P. et al., Mol. Cell. Endocrinol., 215: 83-88 (2004)).

The most potent estrogen is estradiol ($E_2$), which is formed in premenopausal females, mainly in the ovaries. On an endocrine route, it arrives at the target tissues, where it displays its action by means of an interaction with the estrogen receptor (ER) α. After the menopause, the plasma $E_2$ level decreases to $\frac{1}{10}$ of the estradiol level found in premenopausal females (Santner, S. J. et al., J. Clin. Endocrinol. Metab., 59: 29-33 (1984)). $E_2$ is mainly produced in the peripheral tissue, e.g., breast tissue, endometrium, adipose tissue and skin, from inactive precursors, such as estrone sulfate ($E_1$-S), dehydroepiandrosterone (DHEA) and DHEA-S. These reactions occur with the participation of various steroidogenic enzymes (hydroxysteroid dehydrogenases, aromatase), which are in part more abundantly produced in the peripheral tissue, where these active estrogens display their action. As a consequence of such intracrine mechanism for the formation of $E_2$, its concentration in the peripheral tissue, especially in estrogen-related diseases, is higher than that in the healthy tissue. Above all, the growth of many breast cancer cell lines is stimulated by a locally increased estradiol concentration. Further, the occurrence and progress of diseases such as endometriosis, leiomyosis, adenomyosis, menorrhagia, metrorrhagia and dysmenorrhea is dependent on a significantly increased estradiol level in accordingly diseased tissue.

Endometriosis is an estrogen-related disease afflicting about 5 to 10% of all females of childbearing age (Kitawaki, J., Journal of Steroid Biochemistry & Molecular Biology, 83: 149-155 (2003)). From 35 to 50% of the females suffering from abdominal pain and/or sterility show signs of endometriosis (Urdl, W., J. Reproduktionsmed. Endokrinol., 3: 24-30 (2006)). This diseases is defined as a histologically detected ectopic endometrial glandular and stromal tissue. In correspondingly severe cases, this chronic disease, which tends to relapse, leads to pain of different intensities and variable character and possibly to sterility. Three macroscopic clinical pictures are distinguished: peritoneal endometriosis, retroperitoneal deep-infiltrating endometriosis including adenomyosis uteri, and cystic ovarial endometriosis. There are various explanatory theories for the pathogenesis of endometriosis, e.g., the metaplasia theory, the transplantation theory and the theory of autotraumatization of the uterus as established by Leyendecker (Leyendecker, G. et al., Hum. Reprod., 17: 2725-2736 (2002)).

According to the metaplasia theory (Meyer, R., Zentralbl. Gynäkol., 43: 745-750 (1919); Nap, A. W. et al., Best Pract. Res. Clin. Obstet. Gynaecol., 18: 233-244 (2004)), pluripotent coelomic epithelium is supposed to have the ability to differentiate and form endometriotic foci even in adults under certain conditions. This theory is supported by the observation that endometrioses, in part severe ones, can occur in females with lacking uterus and gynastresy. Even in males who were treated with high estrogen doses due to a prostate carcinoma, an endometriosis could be detected in singular cases.

According to the theory postulated by Sampson (Halme, J. et al., Obstet. Gynecol., 64: 151-154 (1984); Sampson, J., Boston Med. Surg. J., 186: 445-473 (1922); Sampson, J., Am. J. Obstet. Gynecol., 14: 422-469 (1927)), retrograde menstruation results in the discharge of normal endometrial cells or fragments of the eutopic endometrium into the abdominal cavity with potential implantation of such cells in the peritoneal space and further development to form endometriotic foci. Retrograde menstruation could be detected as a physiological event. However, not all females with retrograde menstruation become ill with endometriosis, but various factors, such as cytokines, enzymes, growth factors (e.g., matrix metalloproteinases), play a critical role.

The enhanced autonomous non-cyclical estrogen production and activity as well as the reduced estrogen inactivation are typical peculiarities of endometriotic tissue. This enhanced local estrogen production and activity is caused by a significant overexpression of aromatase, expression of 17β-HSD1 and reduced inactivation of potent E2 due to a lack of 17β-HSD2, as compared to the normal endometrium (Bulun, S. E. et al., J. Steroid Biochem. Mol. Biol., 79: 19-25 (2001); Kitawaki, J., Journal of Steroid Biochemistry & Molecular Biology, 83: 149-155 (2003); Karaer, O. et al., Acta. Obstet. Gynecol. Scand., 83: 699-706 (2004); Zeitoun, K. et al., J. Clin. Endocrinol. Metab., 83: 4474-4480 (1998)).

The polymorphic symptoms caused by endometriosis include any pain symptoms in the minor pelvis, back pain, dyspareunia, dysuria and defecation complaints.

One of the therapeutic measures employed most frequently in endometriosis is the surgical removal of the endometriotic foci (Urdl, W., J. Reproduktionsmed. Endokrinol., 3: 24-30 (2006)). Despite new therapeutic concepts, medicamental treatment remains in need of improvement. The purely symptomatic treatment of dysmenorrhea is effected by means of non-steroidal anti-inflammatory drugs (NSAID), such as acetylsalicylic acid, indomethacine, ibuprofen and diclofenac. Since a COX2 overexpression could be observed both in malignant tumors and in the eutopic endometrium of females with endometriosis, a therapy with the selective COX2 inhibitors, such as celecoxib, suggests itself (Fagotti, A. et al., Hum. Reprod. 19: 393-397 (2004); Hayes, E. C. et al., Obstet. Gynecol. Surv., 57: 768-780 (2002)). Although they have a better gastro-intestinal side effect profile as compared to the NSAID, the risk of cardiovascular diseases, infarction and stroke is increases, especially for patients with a predamaged cardiovascular system (Dogne, J. M. et al., Curr. Pharm. Des., 12: 971-975 (2006)). The causal medicamental theory is based on estrogen deprivation with related variable side effects and a generally contraceptive character. The gestagens with their anti-estrogenic and antiproliferative effect on the endometrium have great therapeutic significance. The most frequently employed substances include medroxyprogesterone acetate, norethisterone, cyproterone acetate. The use of danazole is declining due to its androgenic side effect profile with potential gain of weight, hirsutism and acne. The treatment with GnRH analogues is of key importance in the treatment of endometriosis (Rice, V.; Ann. NY Acad. Sci., 955: 343-359 (2001)); however, the duration of the therapy should not exceed a period of 6 months since a longer term application is associated with irreversible damage and an increased risk of fracture. The side effect profile of the GnRH analogues includes hot flushes, amenorrhea, loss of libido and osteoporosis, the latter mainly within the scope of a long term treatment.

Another therapeutic approach involves the steroidal and non-steroidal aromatase inhibitors. It could be shown that the use of the non-steroidal aromatase inhibitor letrozole leads to a significant reduction of the frequency and severity of dysmenorrhea and dyspareunia and to a reduction of the endometriosis marker CA125 level (Soysal, S. et al., Hum. Reprod., 19: 160-167 (2004)). The side effect profile of aromatase inhibitors ranges from hot flushes, nausea, fatigue to osteoporosis and cardiac diseases. Long term effects cannot be excluded.

All the possible therapies mentioned herein are also employed in the combatting of diseases such as leiomyosis, adenomyosis, menorrhagia, metrorrhagia and dysmenorrhea.

Every fourth cancer disease in the female population falls under the category of mammary cancers. This disease is the main cause of death in the Western female population at the age of from 35 to 54 years (Nicholls, P. J., Pharm. J., 259: 459-470 (1997)). Many of these tumors exhibit an estrogen-dependent growth and are referred to as so-called HDBC (hormone dependent breast cancer). A distinction is made between ER+ and ER− tumors. The classification criteria are important to the choice of a suitable therapy. About 50% of the breast cancer cases in premenopausal females and 75% of the breast cancer cases in postmenopausal females are ER+ (Coulson, C., Steroid biosynthesis and action, 2nd edition, 95-122 (1994); Lower, E. et al., Breast Cancer Res. Treat., 58: 205-211 (1999)), i.e., the growth of the tumor is promoted by as low as physiological concentrations of estrogens in the diseased tissue.

The therapy of choice at an early stage of breast cancer is surgical measures, if possible, breast-preserving surgery. Only in a minor number of cases, mastectomy is performed. In order to avoid relapses, the surgery is followed by radiotherapy, or else radiotherapy is performed first in order to reduce a larger tumor to an operable size. In an advanced state, or when metastases occur in the lymph nodes, skin or brain, the objective is no longer to heal the disease, but to achieve a palliative control thereof.

The therapy of the mammary carcinoma is dependent on the hormone receptor status of the tumor, on the patient's hormone status and on the status of the tumor (Paepke, S. et al., Onkologie, 26 Suppl., 7: 4-10 (2003)). Various therapeutical approaches are available, but all are based on hormone deprivation (deprivation of growth-promoting endogenous hormones) or hormone interference (supply of exogenous hormones). However, a precondition of such responsiveness is the endocrine sensitivity of the tumors, which exists with HDBC ER+ tumors. The drugs employed in endocrine therapy include GnRH analogues, anti-estrogens and aromatase inhibitors. GnRH analogues, such as gosereline, will bind to specific membrane receptors in the target organ, the pituitary gland, which results in an increased secretion of FSH and LH. These two hormones in turn lead to a reduction of GnRH receptors in a negative feedback loop in the pituitary cells. The resulting desensitization of the pituitary cells towards GnRH leads to an inhibition of FSH and LH secretion, so that the steroid hormone feedback loop is interrupted. The side effects of such therapeutic agents include hot flushes, sweats and osteoporosis.

Another therapeutic option is the use of anti-estrogens, antagonists at the estrogen receptor. Their activity is based on the ability to competitively bind to the ER and thus avoid the specific binding of the endogenous estrogen. Thus, the natural hormone is no longer able to promote tumor growth. Today, therapeutic use involves so-called SERM (selective estrogen receptor modulators), which develop estrogen agonism in tissues such as bones or liver, but have antagonistic and/or minimal agonistic effects in breast tissue or uterus (Holzgrabe, U., Pharm. Unserer Zeit, 33: 357-359 (2004); Pasqualini, J. R., Biochim. Biophys. Acta., 1654: 123-143 (2004); Sexton, M. J. et al., Prim Care Update Ob Gyns, 8: 25-30 (2001)). Thus, these compounds are not only effective in combatting breast cancer, but also increase the bone density and reduce the risk of osteoporosis in postmenopausal females. The use of the SERM tamoxifen is most widely spread. However, after about 12-18 months of treatment, there is development of resistance, an increased risk of endometrial cancers and thrombo-embolic diseases due to the partial agonistic activity at the ER (Goss, P. E. et al., Clin.

Cancer Res., 10: 5717-5723 (2004); Nunez, N. P. et al., Clin. Cancer Res., 10: 5375-5380 (2004)).

The enzymatically catalyzed estrogen biosynthesis may also be influenced by selective enzyme inhibitors. The enzyme aromatase, which converts C19 steroids to C18 steroids, was one of the first targets for lowering the estradiol level. This enzyme complex, which belongs to the cytochrome P-450 enzymes, catalyzes the aromatization of the androgenic A ring to form estrogens. The methyl group at position 10 of the steroid is thereby cleaved off. The first aromatase inhibitor employed for the therapy of breast cancer was aminogluthetimide. However, aminogluthetimide affects several enzymes of the cytochrome P-450 superfamily and thus inhibits a number of other biochemical conversions. For example, among others, the compound interferes with the steroid production of the adrenal glands so heavily that a substitution of both glucocorticoids and mineral corticoids may be necessary. In the meantime, more potent and more selective aromatase inhibitors, which can be subdivided into steroidal and non-steroidal compounds, are on the market. The steroidal inhibitors include, for example, exemestane, which has a positive effect on the bone density, which is associated with its affinity for the androgen receptor (Goss, P. E. et al., Clin. Cancer Res., 10: 5717-5723 (2004)). However, this type of compounds are irreversible inhibitors that also have a substantial number of side effects, such as hot flushes, nausea, fatigue. However, there are also non-steroidal compounds that are employed therapeutically, for example, letrozole. The advantage of these compounds resides in the lesser side effects, they do not cause uterine hypertrophy, but have no positive effect on the bone density and result in an increase of LDL (low density lipoprotein), cholesterol and triglyceride levels (Goss, P. E. et al., Clin. Cancer Res., 10: 5717-5723 (2004); Nunez, N. P. et al., Clin. Cancer Res., 10: 5375-5380 (2004)). Today, aromatase inhibitors are predominantly employed as second-line therapeutic agents. In the meantime, however, the equivalence or even superiority of aromatase inhibitors to SERM, such as tamoxifene, has been proven in clinical studies (Geisler, J. et al., Crit. Rev. Oncol. Hematol., 57: 53-61 (2006); Howell, A. et al., Lancet, 365: 60-62 (2005)). Thus, the use of aromatase inhibitors also as first-line therapeutical agents is substantiated.

However, the estrogen biosynthesis in the peripheral tissue also includes other pathways for the production of E1 and the more potent E2 by avoiding the enzyme aromatase that is locally present in the target tissue, for example, breast tumors. Two pathways for the production of estrogens in breast cancer tissue are postulated (Pasqualini, J. R., Biochim. Biophys. Acta., 1654: 123-143 (2004)), the aromatase pathway (Abul-Hajj,Y. J. et al., Steroids, 33: 205-222 (1979); Lipton, A. et al., Cancer, 59: 779-782 (1987)) and the sulfatase pathway (Perel, E. et al., J. Steroid. Biochem., 29: 393-399 (1988)). The aromatase pathway includes the production of estrogens from androgens with participation of the enzyme aromatase. The sulfatase pathway is the pathway for the production of estrone/estradiol by means of the enzyme steroid sulfatase, an enzyme that catalyzes the conversion of estrone sulfate and DHEA-S to estrone and DHEA. In this way, 10 times as much estrone is formed in the target tissue as compared to the aromatase pathway (Santner, S. J. et al., J. Clin. Endocrinol. Metab., 59: 29-33 (1984)). The estrone is then reduced by means of the enzyme 17β-HSD1 to form E2, the most potent estrogen. Steroid sulfatase and 17β-HSD1 are new targets in the battle against estrogen-related diseases, especially for the development of therapeutic agents for mammary carcinomas (Pasqualini, J. R., Biochim. Biophys. Acta., 1654: 123-143 (2004)).

Numerous steroidal sulfatase inhibitors could be found, including the potent irreversible inhibitor EMATE, which exhibited an agonistic activity at the estrogen receptor, however (Ciobanu, L. C. et al., Cancer Res., 63: 6442-6446 (2003); Hanson, S. R. et al., Angew. Chem. Int. Ed. Engl., 43: 5736-5763 (2004)). Some potent non-steroidal sulfatase inhibitors could also be found, such as COUMATE and derivatives as well as numerous sulfamate derivatives of tetrahydronaphthalene, indanone and tetralone (Hanson, S. R. et al., Angew. Chem. Int. Ed. Engl., 43: 5736-5763 (2004)). However, no sulfatase inhibitor has been able to enter the therapy of estrogen-related diseases to date.

The inhibition of 17β-HSD1, a key enzyme in the biosynthesis of E2, the most potent estrogen, could suggest itself as an option in the therapy of estrogen-related diseases in both premenopausal and postmenopausal females (Kitawaki, J., Journal of Steroid Biochemistry & Molecular Biology, 83: 149-155 (2003); Allan, G. M. et al., Mol. Cell. Endocrinol., 248: 204-207 (2006); Penning, T. M., Endocr. Rev., 18: 281-305 (1997); Sawicki, M. W. et al., Proc. Natl. Acad. Sci. USA, 96: 840-845 (1999); Vihko, P. et al., Mol. Cell. Endocrinol., 171: 71-76 (2001)). An advantage of this approach is the fact that the intervention is effected in the last step of estrogen biosynthesis, i.e., the conversion of E1 to the highly potent E2 is inhibited. The intervention is effected in the biosynthetic step occurring in the peripheral tissue, so that a reduction of estradiol production takes place locally in the diseased tissue. The use of correspondingly selective inhibitors would probably be associated with little side effects since the synthesis of other steroids would remain unaffected. It would be important that such inhibitors exhibit no or only very little agonistic activity at the ER, especially at the ER α, since agonistic binding is accompanied by an activation and thus proliferation and differentiation of the target cell. In contrast, an antagonistic activity of such compounds at the ER would prevent the natural substrates from binding at the receptor and result in a further reduction of the proliferation of the target cells. The use of selective 17β-HSD1 inhibitors for the therapy of numerous estrogen-dependent diseases is discussed, for example, for breast cancer, tumors of the ovaries, prostate carcinoma, endometrial carcinoma, endometriosis, adenomyosis. Highly interesting and completely novel is the proposal to employ selective inhibitors of 17β-HSD1 for prevention when there is a genetic disposition for breast cancer (Miettinen, M. et al., J. Mammary Gland. Biol. Neoplasia, 5: 259-270 (2000)).

Hydroxysteroid dehydrogenases (HSD) can be subdivided into different classes. The 11β-HSD modulate the activity of glucocorticoids, 3β-HSD catalyzes the reaction of Δ5-3β-hydroxysteroids (DHEA or 5-androstene-3β,17β-diol) to form Δ5-3β-ketosteroids (androstenedione or testosterone). 17β-HSD convert the less active 17-ketosteroids to the corresponding highly active 17-hydroxy compounds (androstenedione to testosterone and $E_1$ to $E_2$) or conversely (Payne, A. H. et al., Endocr. Rev., 25: 947-970 (2004); Peltoketo, H. et al., J. Mol. Endocrinol., 23: 1-11 (1999); Suzuki, T. et al., Endocr. Relat. Cancer, 12: 701-720 (2005)). Thus, the HSD play a critical role in both the activation and the inactivation of steroid hormones. Depending on the cell's need for steroid hormones, they alter the potency of the sex hormones (Penning, T. M., Endocr. Rev., 18: 281-305 (1997)), for example, $E_1$ is converted to the highly potent $E_2$ by means of 17β-HSD1, while $E_2$ is converted to the less potent $E_1$ by means of 17β-HSD2; 17β-HSD2 inactivates $E_2$ while 17β-HSD1 activates $E_1$.

To date, fourteen different 17β-HSDs have been identified (Mindnich, R. et al., Mol. Cell. Endocrinol., 218: 7-20

(2004); Lukacik, P. et al., Mol. Cell. Endocrinol., 248: 61-71 (2006)), and twelve of these enzymes could be cloned (Suzuki, T. et al., Endocr. Relat. Cancer, 12: 701-720 (2005)). They all belong to the so-called short chain dehydrogenase/reductase (SDR) family, with the exception of 17β-HSD5, which is a ketoreductase. The amino acid identity between the different 17β-HSDs is as low as 20-30% (Luu-The, V., J. Steroid Biochem. Mol. Biol., 76: 143-151 (2001)), and they are membrane-bound or soluble enzymes. The X-ray structure of 6 human subtypes is known (1,4,5,10,11,14) (Ghosh, D. et al., Structure, 3: 503-513 (1995); Kissinger, C. R. et al., J. Mol. Biol., 342: 943-952 (2004); Zhou, M. et al., Acta Crystallogr. D. Biol. Crystallogr., 58: 1048-1050 (2002). The 17β-HSDs are NAD(H)-dependent and NADP(H)-dependent enzymes. They play a critical role in the hormonal regulation in humans. The enzymes are distinguished by their tissue distribution, catalytic preference (oxidation or reduction), substrate specificity and subcellular localization. The same HSD subtype was found in different tissues. It is likely that all 17β-HSDs are expressed in the different estrogen-dependent tissues, but in different concentrations. In diseased tissue, the ratio between the different subtypes is altered as compared to healthy tissue, some subtypes being overexpressed while others may be absent. This may cause an increase or decrease of the concentration of the corresponding steroid. Thus, the 17β-HSDs play an extremely important role in the regulation of the activity of the sex hormones. Further, they are involved in the development of estrogen-sensitive diseases, such as breast cancer, ovarian, uterine and endometrial carcinomas, as well as androgen-related diseases, such as prostate carcinoma, benign prostate hyperplasia, acne, hirsutism etc. It has been shown that some 17β-HSDs are also involved in the development of further diseases, e.g., pseudohermaphrodism (17β-HSD3 (Geissler, W. M. et al., Nat. Genet., 7: 34-39 (1994))), bifunctional enzyme deficiency (17β-HSD4 (van Grunsven, E. G. et al., Proc. Natl. Acad. Sci. USA, 95: 2128-2133 (1998))), polycystic kidney diseases (17β-HSD8 (Maxwell, M. M. et al., J. Biol. Chem., 270: 25213-25219 (1995))) and Alzheimer's (17β-HSD10 (Kissinger, C. R. et al., J. Mol. Biol., 342: 943-952 (2004); He, X. Y. et al., J. Biol. Chem., 274: 15014-15019 (1999); He, X. Y. et al., Mol. Cell. Endocrinol., 229: 111-117 (2005); He, X. Y. et al., J. Steroid Biochem. Mol. Biol., 87: 191-198 (2003); Yan, S. D. et al., Nature, 389: 689-695 (1997))).

The best characterized member of the 17β-HSDs is the type 1 17β-HSD. The 17β-HSD1 is an enzyme from the SDR family, also referred to as human placenta estradiol dehydrogenase (Gangloff, A. et al., Biochem. J., 356: 269-276 (2001); Jornvall, H. et al., Biochemistry, 34: 6003-6013 (1995)). Its designation as assigned by the enzyme commission is E.C.1.1.1.62.

Engel et al. (Langer, L. J. et al., J. Biol. Chem., 233: 583-588 (1958)) were the first to describe this enzyme in the 1950's. In the 1990's, first crystallization attempts were made, so that a total of 16 crystallographic structures can be recurred to today in the development of inhibitors (Alho-Richmond, S. et al., Mol. Cell. Endocrinol., 248: 208-213 (2006)). Available are X-ray structures of the enzyme alone, but also of binary and ternary complexes of the enzyme with its substrate and other ligands or substrate/ligand and cofactor.

17β-HSD1 is a soluble cytosolic enzyme. NADPH serves as a cofactor. 17β-HSD1 is encoded by a 3.2 kb gene consisting of 6 exons and 5 introns that is converted to a 2.2 kb transcript (Luu-The, V., J. Steroid Biochem. Mol. Biol., 76: 143-151 (2001); Labrie, F. et al., J. Mol. Endocrinol., 25: 1-16 (2000)). It is constituted by 327 amino acids. The molecular weight of the monomer is 34.9 kDa (Penning, T. M., Endocr. Rev., 18: 281-305 (1997)). 17β-HSD1 is expressed in the placenta, liver, ovaries, endometrium, prostate gland, peripheral tissue, such as adipose tissue and breast cancer cells (Penning, T. M., Endocr. Rev., 18: 281-305 (1997)). It was isolated for the first time from human placenta (Jarabak, J. et al., J. Biol. Chem., 237: 345-357 (1962)). The main function of 17β-HSD1 is the conversion of the less active estrone to the highly potent estradiol. However, it also catalyzes to a lesser extent the reaction of dehydroepiandrosterone (DHEA) to 5-androstene-3β,17β-diol, an androgen showing estrogenic activity (Labrie, F., Mol. Cell. Endocrinol., 78: C113-118 (1991); Poirier, D., Curr. Med. Chem., 10: 453-477 (2003); Poulin, R. et al., Cancer Res., 46: 4933-4937 (1986)). In vitro, the enzyme catalyzes the reduction and oxidation between $E_1$ and $E_2$ while it catalyzes only the reduction under physiological conditions. These bisubstrate reactions proceed according to a random catalytic mechanism, i.e., either the steroid or the cofactor is first to bind to the enzyme (Betz, G., J. Biol. Chem., 246: 2063-2068 (1971)). A catalytic mechanism in which the cofactor binds to the enzyme first is also postulated (Neugebauer, A. et al., Bioorg. Med. Chem., eingereicht (2005)).

The enzyme consists of a substrate binding site and a channel that opens into the cofactor binding site. The substrate binding site is a hydrophobic tunnel having a high complementarity to the steroid. The 3-hydroxy and 17-hydroxy groups in the steroid form four hydrogen bonds to the amino acid residues His221, Glu282, Ser142 and Tyr155. The hydrophobic van der Waals interactions seem to form the main interactions with the steroid while the hydrogen bonds are responsible for the specificity of the steroid for the enzyme (Labrie, F. et al., Steroids, 62: 148-158 (1997)). Like with all the other enzymes of this family, what is present as a cofactor binding site is the Rossmann fold, which is a region consisting of α-helices and β-sheets $(β-α-β-α-β)_2$, a generally occurring motif Gly-Xaa-Xaa-Xaa-Gly-Xaa-Gly, and a nonsense region Tyr-Xaa-Xaa-Xaa-Lys within the active site. What is important to the activity is a catalytic tetrade consisting of Tyr155-Lys159-Ser142-Asn114, which stabilize the steroid and the ribose in the nicotinamide during the hydride transfer (Alho-Richmond, S. et al., Mol. Cell. Endocrinol., 248: 208-213 (2006); Labrie, F. et al., Steroids, 62: 148-158 (1997); Nahoum, V. et al., Faseb. J., 17: 1334-1336 (2003)).

The gene encoding 17β-HSD1 is linked with the gene for mammary and ovarian carcinomas that is very susceptible to mutations and can be inherited, the BRCA1 gene, on chromosome 17q11-q21 (Labrie, F. et al., J. Mol. Endocrinol., 25: 1-16 (2000)). As has been demonstrated, the activity of 17β-HSD1 is higher in endometrial tissue and breast cancer cells as compared to healthy tissue, which entails high intracellular estradiol levels, which in turn cause proliferation and differentiation of the diseased tissue (Bulun, S. E. et al., J. Steroid Biochem. Mol. Biol., 79: 19-25 (2001); Miyoshi, Y. et al., Int. J. Cancer, 94: 685-689 (2001); Kitawaki, J., Journal of Steroid Biochemistry & Molecular Biology, 83: 149-155 (2003); Pasqualini, J. R., Biochim. Biophys. Acta., 1654: 123-143 (2004); Vihko, P. et al., Mol. Cell. Endocrinol., 171: 71-76

(2001); Miettinen, M. et al., Breast Cancer Res. Treat., 57: 175-182 (1999); Sasano, H. et al., J. Clin. Endocrinol. Metab., 81: 4042-4046 (1996); Yoshimura, N. et al., Breast Cancer Res., 6: R46-55 (2004)). An inhibition of 17β-HSD1 could result in the estradiol level being lowered and thus lead to a regression of the estrogen-related diseases. Further, selective inhibitors of 17β-HSD1 could be used for prevention when there is a genetic disposition for breast cancer (Miettinen, M. et al., J. Mammary Gland. Biol. Neoplasia, 5: 259-270 (2000)).

Thus, this enzyme would suggest itself as a target for the development of novel selective and non-steroidal inhibitors as therapeutic agents in the battle against estrogen-related diseases. However, there has not been a proof of concept to date.

In the literature, only a few compounds have been described as inhibitors of 17β-HSD1 (Poirier, D., Curr. Med. Chem., 10: 453-477 (2003)). Most inhibitors are steroidal compounds obtained by different variations of the estrogen skeleton (Allan, G. M. et al., J. Med. Chem., 49: 1325-1345 (2006); Deluca, D. et al., Mol. Cell. Endocrinol., 248: 218-224 (2006); WO2006/003012; US2006/652461; WO2005/047303).

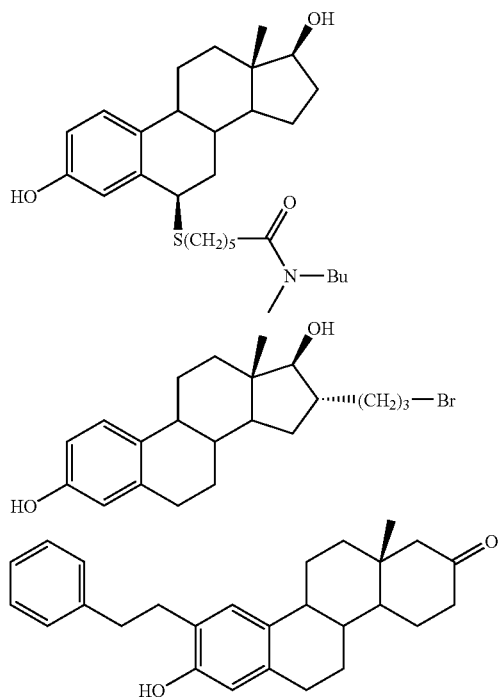

Another class of compounds which has been described is the so-called hybrid inhibitors (Qiu, W. et al., FASEB J., 16: 1829-1830 (2002); online: doi 10.1096/fj.02-0026fje), compounds that, due to their molecular structure, not only attack at the substrate binding site, but also undergo interactions with the cofactor binding site. The inhibitors have the following structure:

adenosine moiety or simplified derivatives that can interact with the cofactor binding site;

estradiol or estrone moiety, which interacts with the substrate binding site; and a spacer of varying length as a linking element between the two moieties.

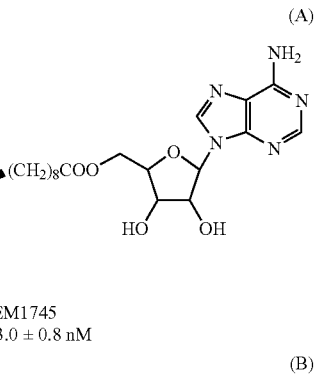

EM1745
$K_i = 3.0 \pm 0.8$ nM

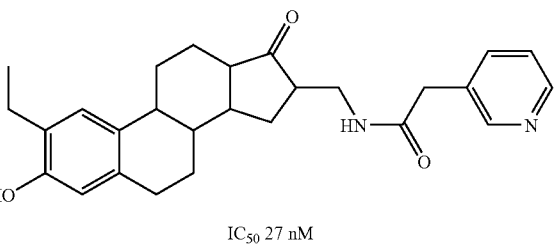

$IC_{50}$ 27 nM

Among these compounds, inhibitors have been synthesized that exhibit a good inhibition of the enzyme and a good selectivity for 17β-HSD2 (compound B (Lawrence, H. R. et al., J. Med. Chem., 48: 2759-2762 (2005))). In addition, the inventors consider that a small estrogenic effect can be achieved by a substitution at the C2 of the steroid skeleton (Cushman, M. et al., J. Med. Chem., 38: 2041-2049 (1995); Leese, M. P. et al., J. Med. Chem., 48: 5243-5256 (2005)); however, this effect has not yet been demonstrated in tests.

However, a drawback of these steroidal compounds may be a low selectivity. With steroids, there is a risk that the compounds will also attack other enzymes of the steroid biosynthesis, which would lead to side effects. In addition, due to their steroidal structure, they may have an affinity for steroid receptors and function as agonists or antagonists.

Among the phytoestrogens, which have affinity for the estrogen receptor and act as estrogens or anti-estrogens depending on the physiological conditions, flavones, isoflavones and lignans have been tested for an inhibitory activity (Makela, S. et al., Proc. Soc. Exp. Biol. Med., 217: 310-316 (1998); Makela, S. et al., Proc. Soc. Exp. Biol. Med., 208: 51-59 (1995); Brooks, J. D. et al., J. Steroid Biochem. Mol. Biol., 94: 461-467 (2005)). Coumestrol was found to be particularly potent, but of course showed estrogenic activity (Nogowski, L., J. Nutr. Biochem., 10: 664-669 (1999)). Gossypol derivatives were also synthesized as inhibitors (US2005/0228038). In this case, however, the cofactor binding site rather than the substrate binding site is chosen as the target site (Brown, W. M. et al., Chem. Biol. Interact., 143-144, 481-491 (2003)), which might entail problems in selectivity with respect to other enzymes utilizing NAD(H) or NADP(H).

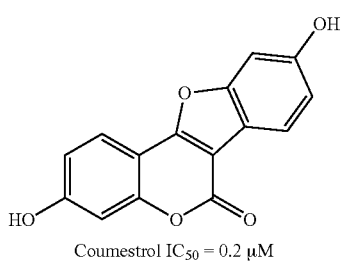 [SMILES: O=c1oc2cc(O)ccc2c2oc3cc(O)ccc3c12]

Coumestrol IC$_{50}$ = 0.2 µM

In addition to diketones, such as 2,3-butanedione and glyoxal, which were used for studies on the enzyme, suicide inhibitors were also tested. However, these were found not to be therapeutically utilizable since the oxidation rate of the alcohols to the corresponding reactive form, namely the ketones, was too weak (Poirier, D., Curr. Med. Chem., 10: 453-477 (2003)).

In other studies, Jarabak et al. (Jarabak, J. et al., Biochemistry, 8: 2203-2212 (1969)) examined various non-steroidal inhibitors for their inhibitory effect, U-11-100A having been found as the most potent compound in this group. However, as compared to other non-steroidal compounds, U-11-100A is a weak inhibitor of 17β-HSD1.

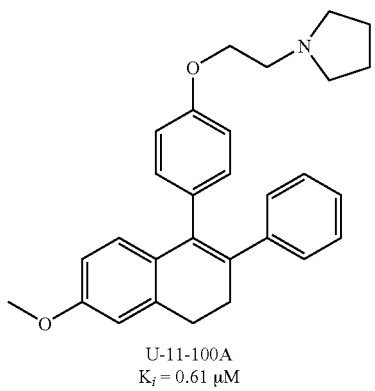 [SMILES: COc1ccc2c(c1)CCC(c1ccccc1)=C2c1ccc(OCCN2CCCC2)cc1]

U-11-100A
K$_i$ = 0.61 µM

As further non-steroidal inhibitors, thiophenepyrimidinones have been examined (US2005/038053; Messinger, J. et al., Mol. Cell. Endocrinol., 248: 192-198 (2006); WO2004/110459).

In addition, some phenylnaphthalene and phenylquinoline derivatives have been known from the literature:

6-(3-Hydroxyphenyl)naphthalene-2-ol, 6-(2-hydroxyphenyl)naphthalene-2-ol and 6-phenylnaphthalene-2-ol have been described as compounds having estrogenic activity (Cassebaum, H., Chemische Berichte, 90: 2876-2888 (1957); WO2005/014551; WO2003/051805; Mewshaw, R. E. et al., J. Med. Chem., 48: 3953-3979 (2005); Shunk, C. et al., J. Am. Chem. Soc., 71: 3946-3950 (1949); Tao, B. et al., Tetrahedron Letters, 43: 4955-4957 (2002); Hey, D. et al., J. Chem. Soc., 374-383 (1940).

4-(Naphthalene-2-yl)phenol has been described in WO2006/045096; Mewshaw, R. et al., J. Med. Chem. 48: 3953-3979 (2005), and WO2003/051805. Further derivatives of 4-(naphthalene-2-yl)phenol are known from WO2003/051805 and Smyth, M. S. et al., J. Med. Chem., 36: 3015-3020 (1993).

3-(Naphthalene-2-yl)phenol (Eichinger, K. et al., Synthesis, 8: 663-664 (1991); Nasipuri, D. et al., J. Chem. Soc. [Section] D: Chemical Communications, 13: 660-661 (1971); Raychaudhuri, S. R., Chem. Ind., 7: 293-294 (1980)), 4-(quinoline-3-yl)phenol (Cacchi, S. et al., Tetrahedron, 52: 10225-10240 (1996); Kaslow, C. et al., J. Org. Chem., 23: 271-276 (1958); Ma, Z. Z. et al., Phytochemistry, 53: 1075-1078 (2000)) and 2-(3-hydroxyphenyl)quinoline-6-ol (Kamenikova, L., Folia Pharmaceutica (Prague), 4: 37-71 (1982)) have been described as compounds having an analgetic effect.

4-Carboxy-2-(3-carboxy-4-hydroxyphenyl)quinoline, 4-carboxy-6-hydroxy-2-(3-hydroxyphenyl)quinoline, 2-(3-carboxyphenyl)quinoline, 4-carboxy-2-(3,4-dihydroxyphenyl)quinoline and 4-carboxy-7-hydroxy-2-(3,4-dihydroxyphenyl)-quinoline are known from U.S. Pat. No. 1,181,485, Bass, R. J., Chem. Ind., 17: 849 (1973), Gilman, H. and Soddy, T. S., J. Org. Chem., 23: 1584-85 (1958), and Holdsworth, M. G. and Lions, F., J. Proc. Royal Soc. NSW, 66: 473-476 (1933), respectively.

2-(3-Hydroxy-4-methoxyphenyl)quinoxaline, 2-(3-hydroxyphenyl)quinoxaline and 2-(3,4-dihydroxyphenyl)quinoxaline are known from Kovacs, Ö. et al. in Chem. Ber. 84: 795-801 (1951), and in Chem. et Phys., 3: 35-37 (1950).

3-(Quinoline-3-yl)phenol is a commercial product (Akos Consulting Solution GmbH, Basel, Switzerland, Order No. BH-1322; Aurora Fine Chemicals, Graz, Austria, Order No. kaccm-0002421).

WO2003/051805 further describes a wide variety of compounds having a 6-(4-hydroxyphenyl)naphthalene-2-ol skeleton that are estrogen receptor ligands with a high estrogen receptor affinity and a high estrogen receptor agonistic activity (estrogenicity). To date, however, none of the compounds mentioned has been reported as an inhibitor of 17β-HSD1. Since the compounds have been optimized for high estrogen receptor affinities, a strong inhibition of 17β is not to be expected in the first place. However, even if the compounds were inhibitors of 17β-HSD1, their strong estrogen receptor affinities would result in a systemic effect. However, such a systemic effect is just not desirable for certain applications.

SUMMARY OF THE INVENTION

It has now been found that certain phenylnaphthalene and phenylquinoline derivatives are potent inhibitors of 17β-HSD1, but at the same time exhibit a low affinity for 17β-HSD2 and the estrogen receptors α and β. The estrogen receptor affinities of the 17β-HSD1 inhibitors of the present invention are extremely low, as can be derived from the exemplary values shown in Table 2. Thus, the invention relates to:
(1) the use of a compound having the structure (I)

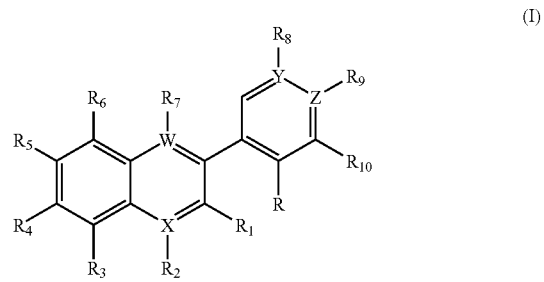

wherein
W, X, Y and Z are independently —C= or —N=,
R is H, halogen, alkyl, alkoxy or alkylsulfanyl,
R$_1$ is H, halogen, OH, CN, COOH, alkyl, alkoxy, alkylsulfanyl, aryl, heteroaryl, arylsulfanyl, —NHSO$_2$R', —R"—

$-NHSO_2R'$, $-SO_2NHR'$, $-R''-SO_2NHR'$, $-NHCOR'$, $-CONHR'$, $-R''-NHCOR'$, $-R''-CONHR'$, $-COOR'$, $-OOCR'$, $-R''-COOR'$, $-R''-OOCR'$, $-CHNR'$, $-SO_2R'$ or $-SOR'$, $R_2$ is H, halogen, OH, CN, COOH, alkyl, alkoxy, alkylsulfanyl, aryl, heteroaryl, arylsulfanyl, $-NHSO_2R'$, $-R''-NHSO_2R'$, $-SO_2NHR'$, $-R''-SO_2NHR'$, $-NHCOR'$, $-CONHR'$, $-R''-NHCOR'$, $-R''-CONHR'$, $-COOR'$, $-OOCR'$, $-R''-COOR'$, $-R''-OOCR'$, $-CHNR'$, $-SO_2R'$ or $-SOR'$, or is absent if X is $-N=$, $R_3$ is H, halogen, OH, CN, COOH, alkyl, alkoxy, alkylsulfanyl, aryl, heteroaryl, arylsulfanyl, $-NHSO_2R'$, $-R''-NHSO_2R'$, $-SO_2NHR'$, $-R''-SO_2NHR'$, $-NHCOR'$, $-CONHR'$, $-R''-NHCOR'$, $-R''-CONHR'$, $-COOR'$, $-OOCR'$, $-R''-COOR'$, $-R''-OOCR'$, $-CHNR'$, $-SO_2R'$, or $-SOR'$, $R_4$ is H or OH, $R_5$ is H, halogen, OH, CN, COOH, alkyl, alkoxy, alkylsulfanyl, aryl, heteroaryl, arylsulfanyl, $-NHSO_2R'$, $-R''-NHSO_2R'$, $-SO_2NHR'$, $-R''-SO_2NHR'$, $-NHCOR'$, $-CONHR'$, $-R''-NHCOR'$, $-R''-CONHR'$, $-COOR'$, $-OOCR'$, $-R''-COOR'$, $-R''-OOCR'$, $-CHNR'$, $-SO_2R'$ or $-SOR'$, $R_6$ is H, halogen, OH, CN, COOH, alkyl, alkoxy, alkylsulfanyl, aryl, heteroaryl, arylsulfanyl, $-NHSO_2R'$, $-R''-NHSO_2R'$, $-SO_2NHR'$, $-R''-SO_2NHR'$, $-NHCOR'$, $-CONHR'$, $-R''-NHCOR'$, $-R''-CONHR'$, $-COOR'$, $-OOCR'$, $-R''-COOR'$, $-R''-OOCR'$, $-CHNR'$, $-SO_2R'$ or $-SOR'$, $R_7$ is H, halogen, OH, CN, COOH, alkyl, alkoxy, alkylsulfanyl, aryl, heteroaryl, arylsulfanyl, $-NHSO_2R'$, $-R''-NHSO_2R'$, $-SO_2NHR'$, $-R''-SO_2NHR'$, $-NHCOR'$, $-CONHR'$, $-R''-NHCOR'$, $-R''-CONHR'$, $-COOR'$, $-OOCR'$, $-R''-COOR'$, $-R''-OOCR'$, $-CHNR'$, $-SO_2R'$ or $-SOR'$, or is absent if W is $-N=$, $R_8$ is H, halogen, OH, CN, COOH, alkyl, alkoxy, alkylsulfanyl, aryl, heteroaryl, arylsulfanyl, $-NHSO_2R'$, $-R''-NHSO_2R'$, $-SO_2NHR'$, $-R''-SO_2NHR'$, $-NHCOR'$, $-CONHR'$, $-R''-NHCOR'$, $-R''-CONHR'$, $-COOR'$, $-OOCR'$, $-R''-COOR'$, $-R''-OOCR'$, $-CHNR'$, $-SO_2R'$ or $-SOR'$, or is absent if Y is $-N=$, $R_9$ is H, halogen, CN, COOH or $CH_2OH$, or is absent if Z is $-N=$, and $R_{10}$ is H, OH, CN, COOH, $CH_2OH$, $NO_2$ or $NH_2$, with the proviso that at least one of $R_8$ and $R_{10}$ is OH or COOH, R' is alkyl, aryl or heteroaryl, R'' is alkylene, arylene or heteroarylene, the aryl, arylene, heteroaryl and heteroarylene residues in $R_1$, $R_2$, $R_3$, $R_5$, $R_6$, $R_7$, $R_8$, R' and R'' may be substituted with 1 to 5 residues R''' and wherein the residues R''' are independently selected from halogen, OH, CN, alkyl, alkoxy, halogenated alkyl, halogenated alkoxy, alkylsulfanyl, arylsulfanyl, heteroarylsulfanyl, aryl, heteroaryl (wherein these aryl and heteroaryl residues may optionally have up to 3 substituents selected from halogen, OH, CN, lower alkyl, lower alkoxy, halogenated lower alkyl, halogenated lower alkoxy, (lower alkyl)sulfanyl, $-COOR_{11}$, $-CH_2OH$, $-NO_2$ and $-N(R_{11})_2$), -(lower alkylene)-$NHSO_2R''''$, -(lower alkylene)-$SO_2NHR''''$, -(lower alkylene)-$NHCOR''''$, -(lower alkylene)-$CONHR''''$, -(lower alkylene)-$COOR''''$, -(lower alkylene)-$OOCR''''$, (wherein R'''' is optionally halogenated lower alkyl, optionally halogenated lower alkoxy, aryl or heteroaryl), $-COOR_{11}$, $-CH_2OH$, $-NO_2$ and $-N(R_{11})_2$, the alkyl, alkoxy- and alkylene residues in R, $R_1$, $R_2$, $R_3$, $R_5$, $R_6$, $R_7$, $R_8$, R' and R'' may be substituted with 1 to 3 residues independently selected from halogen, OH, CN, lower alkyl, lower alkoxy, halogenated lower alkyl, halogenated lower alkoxy, (lower alkyl)sulfanyl, $-COOR_{11}$, $-CH_2OH$, $-NO_2$ and $N(R_{11})_2$, and $R_{11}$ is independently selected from H and lower alkyl, or two residues $R_{11}$ form a 5- to 7-membered saturated heterocycle together with the N atom linking them, and pharmacologically acceptable salts thereof, for the treatment and prophylaxis of hormone-related diseases;

(2) a compound of structure (I), wherein W, X, Y, Z, R, $R_1$, $R_2$, $R_3$, $R_4$, $R_5$, $R_6$, $R_7$, $R_8$, $R_9$ and $R_{10}$ have the meanings as stated in (1), and pharmacologically acceptable salts thereof, with the proviso that:

(a) if W, X, Y and Z are $-C=$, $R_4$ is OH or H, R, $R_1$, $R_2$, $R_3$, $R_5$, $R_6$, $R_7$ and $R_9$ are H, then one of $R_8$ and $R_{10}$ is not OH and the other is H, (b) if X, Y and Z are $-C=$, W is $-N=$ and $R_7$ is absent, R, $R_1$, $R_2$, $R_3$, $R_5$, $R_6$ and $R_9$ are H, $R_4$ is OH or H, then one of $R_8$ and $R_{10}$ is not OH and the other is H;

(c) if X, Y and Z are $-C=$, W is $-N=$ and $R_7$ is absent, R, $R_1$, $R_3$, $R_5$, $R_6$ and $R_9$ are H, $R_2$ is COOH and $R_4$ is OH, then one of $R_8$ and $R_{10}$ is not OH and the other is H, (d) if X, Y and Z are $-C=$, W is $-N=$ and $R_7$ is absent and R, $R_1$, $R_2$, $R_3$, $R_4$, $R_5$, $R_6$ and $R_9$ are H, then one of $R_8$ and $R_{10}$ is not COOH and the other is H, and (e) if Y and Z are $-C=$, X and W are $-N=$, $R_2$ and $R_7$ are absent and R, $R_1$, $R_3$, $R_4$, $R_5$, $R_6$ and $R_9$ are H, then one of $R_8$ and $R_{10}$ is not OH and the other is H;

(3) a medicament or pharmaceutical composition containing at least one of the compounds as defined in (2) and optionally a pharmacologically suitable carrier;

(4) a process for the preparation of the compound as defined in (2) having the structure (I), comprising the following reaction of compounds (II) and (III):

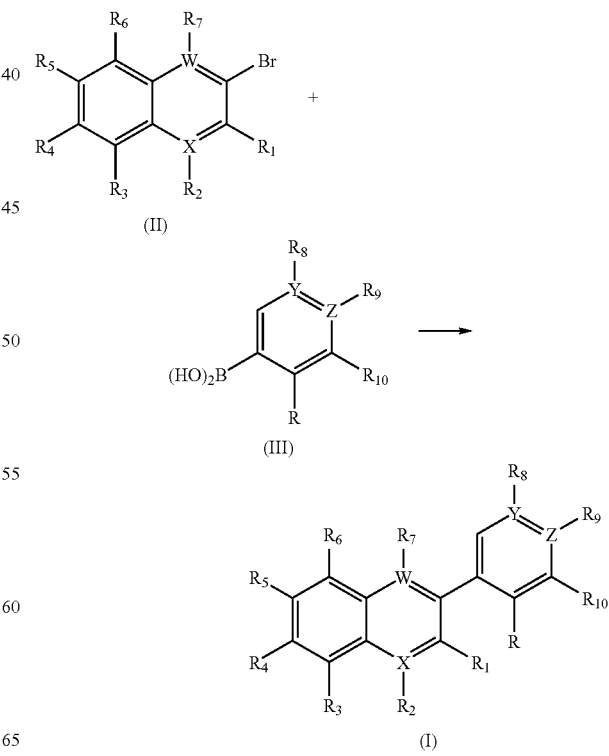

wherein W, X, Y, Z, R and $R_1$ to $R_{10}$ have the meanings as stated in (2) or are protected variants thereof; and (5) a process for the treatment and prophylaxis of hormone-related diseases in a patient, comprising administering a compound as defined in (1) or (2) having the structure (I) to said patient.

The compound of structure (I) as defined in (1) or (2) and the medicament or pharmaceutical composition as defined in (3) and the process as defined in (5) are suitable according to the invention for the treatment and prophylaxis of hormone-related, especially estrogen-related, diseases. Preferably, they are suitable for the treatment and prophylaxis of diseases in which a modulation of the estradiol level is required, such as the treatment and prophylaxis of endometriosis, endometrial carcinoma, adenomyosis, breast cancer, and ovarian carcinoma.

DETAILED DESCRIPTION OF THE INVENTION

In the compounds of formula (I) of the invention, the variables and the terms used for their characterization have the following meanings:

"Alkyl residues" and "alkoxy residues" within the meaning of the invention may be straight-chain, branched-chain or cyclic, and saturated or (partially) unsaturated. Preferable alkyl residues and alkoxy residues are saturated or have one or more double and/or triple bonds. Of straight-chain or branched-chain alkyl residues, preferred are those having from 1 to 10 carbon atoms, more preferably those having from 1 to 6 carbon atoms, even more preferably those having from 1 to 3 carbon atoms. Of the cyclic alkyl residues, more preferred are mono- or bicyclic alkyl residues having from 3 to 15 carbon atoms, especially monocyclic alkyl residues having from 3 to 8 carbon atoms.

"Lower alkyl residues" and "lower alkoxy residues" within the meaning of the invention are straight-chain, branched-chain or cyclic saturated lower alkyl residues and lower alkoxy residues or those having a double or triple bond. Of the straight-chain ones, those having from 1 to 6 carbon atoms, especially 1 to 3 carbon atoms, are particularly preferred.

"Aryls" within the meaning of the present invention include mono-, bi- and tricyclic aryl residues having from 3 to 18 ring atoms, which may optionally be anellated with one or more saturated rings. Particularly preferred are anthracenyl, dihydronaphthyl, fluorenyl, hydrindanyl, indanyl, indenyl, naphthyl, naphthenyl, phenanthrenyl, phenyl and tetralinyl.

Unless stated otherwise, "heteroaryl residues" are mono- or bicyclic heteroaryl residues having from 3 to 12 ring atoms and preferably having from 1 to 5 heteroatoms selected from nitrogen, oxygen and sulfur, which may be anellated with one or more saturated rings. The preferred nitrogen-containing monocyclic and bicyclic heteroaryls include benzimidazolyl, benzothiazolyl, benzoxazolyl, quinazolinyl, quinolyl, quinoxalinyl, cinnolinyl, dihydroindolyl, dihydroisoindolyl, dihydropyranyl, dithiazolyl, furyl, homopiperidinyl, imidazolidinyl, imidazolinyl, imidazolyl, indazolyl, indolyl, isoquinolyl, isoindolyl, isothiazolidinyl, isothiazolyl, isoxazolidinyl, isoxazolyl, morpholinyl, oxadiazolyl, oxazolidinyl, oxazolyl, phthalazinyl, piperazinyl, piperidyl, pteridinyl, purinyl, pyrazolidinyl, pyrazinyl, pyrazolyl, pyrazolinyl, pyridazinyl, pyridyl, pyrimidyl, pyrrolidinyl, pyrrolidin-2-onyl, pyrrolinyl, pyrrolyl, tetrazinyl, tetrazolyl, tetrahydropyrrolyl, thiadiazolyl, thiazinyl, thiazolidinyl, thiazolyl, triazinyl and triazolyl. Particularly preferred are mono- or bicyclic heteroaryl residues with 5 to 10 ring atoms, preferably having from 1 to 3 nitrogen atoms, oxazolyl, imidazolyl, pyridyl and pyrimidyl being more preferred.

"5- to 7-membered saturated heterocycles" within the meaning of this invention include the saturated equivalents of the above mentioned heteroaryl compounds, morpholine, piperazine and piperidine being more preferred.

"Alkylenes", "lower alkylenes", "arylenes" and "heteroarylenes" within the meaning of this invention include the bivalent equivalents of the above defined alkyl, lower alkyl, aryl and heteroaryl residues.

"Halogen" includes fluorine, chlorine, bromine and iodine.

"Halogenated" or "optionally halogenated" residues within the meaning of the present invention include any residues in which one to all H atoms have been replaced by the above mentioned halogen atoms or combinations of such halogen atoms.

"Pharmaceutically acceptable salts" within the meaning of the present invention include salts of the compounds with organic acids (such as lactic acid, acetic acid, amino acid, oxalic acid etc.), inorganic acids (such as HCl, HBr, phosphoric acid etc.), and, if the compounds have acid substituents, also with organic or inorganic bases. Preferred are salts with HCl.

"Pharmacologically suitable carriers" within the meaning of the present invention are selected by the skilled person, depending on the desired dosage form.

In the following, the preferred embodiments of the compound of formula (I) in (1) and (2) are represented. Thus, it is preferred that at least two of the variables W, X, Y and Z are —C═, more preferably at least three of the variables W, X, Y and Z are —C═.

Further, it is preferred that R is H, halogen, lower alkyl, lower alkoxy or (lower alkyl)sulfanyl.

Also preferred are those compounds in which one of $R_3$ and $R_5$ is H, halogen, OH, CN, COOH, alkyl, alkoxy, alkylsulfanyl, aryl, heteroaryl, arylsulfanyl, —NHSO$_2$R', —R"—NHSO$_2$R', —SO$_2$NHR', —R"—SO$_2$NHR', —NHCOR', —CONHR', —R"—NHCOR', —R"—CONHR', —COOR', —OOCR', —R"—COOR', —R"—OOCR', —CHNR', —SO$_2$R' or —SOR', wherein R' and R" have the meanings as stated above and, like the aryl, arylene, heteroaryl and heteroarylene residues, may be substituted with 1 to 3 residues R''', and R''' has the meaning as stated above. The other of the two residues $R_3$ and $R_5$, like the residues Reste $R_1$, $R_2$, $R_6$ and $R_7$, is preferably selected from H, halogen, OH, CN, COOH, lower alkyl, lower alkoxy, (lower alkyl)sulfanyl, aryl, heteroaryl, arylsulfanyl, —NHSO$_2$R', —SO$_2$NHR', —NHCOR', —CONHR', —COOR', —OOCR', CHNR', —SO$_2$R' and —SOR', wherein R' is lower alkyl, phenyl or pyridinyl.

Also preferred are those compounds in which $R_8$ is H, halogen, hydroxy, CN, COOH, lower alkyl, lower alkoxy, (lower alkyl)sulfanyl, aryl, heteroaryl, arylsulfanyl, —NHSO$_2$R', —SO$_2$NHR', —NHCOR', —CONHR', —COOR', —OOCR', —CHNR', —SO$_2$R' or —SOR', wherein R' is lower alkyl, phenyl or pyridinyl.

Finally, those compounds are preferred in which $R_9$ is H, CN, COOH or CH$_2$OH, or is absent if Z is —N═, and those compounds in which $R_4$ is OH.

In particularly preferred embodiments of (1) and (2), in the compounds of structure (I), W, X, Y and Z are —C═, or one of W and X is —N═ and the other, like Y and Z, is —C═.

Particularly preferred are further those compounds in which $R_3$ is selected from H, halogen, OH, CN, COOH, alkyl, alkoxy, alkylsulfanyl, aryl, heteroaryl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R' and —SOR', preferably aryl, heteroaryl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R' and —SOR', wherein R' and R" have the meanings as stated above and, like the aryl, arylene, heteroaryl and heteroarylene residues, may be substituted with 1 to 3 residues R'" and R'" has the meaning as stated above.

Particularly preferred are further those compounds in which $R_1$, $R_2$, $R_5$, $R_6$ and $R_7$ are independently selected from H, halogen, hydroxy, CN, COOH, lower alkyl, lower alkoxy, (lower alkyl)sulfanyl, phenyl, pyridyl, phenylsulfanyl, —NHSO₂R', —SO₂NHR', —NHCOR', —CONHR', SO₂R' and —SOR', wherein R' is lower alkyl, phenyl or pyridinyl. Of these, those compounds are particularly preferred in which the residues mentioned are independently H, F, Cl, CN, lower alkyl or lower alkoxy.

Also particularly preferred are compounds in which $R_8$ is H, halogen, hydroxy, CN, COOH, lower alkyl, lower alkoxy, (lower alkyl)sulfanyl, phenyl, pyridyl, phenylsulfanyl, —NHSO₂R', —SO₂NHR', —NHCOR', —CONHR', —SO₂R' or —SOR', wherein R' is lower alkyl, phenyl or pyridinyl. Of these, those compounds are particularly preferred in which $R_8$ is H, F, Cl, OH, CN, COOH, lower alkyl or lower alkoxy.

Also particularly preferred are compounds in which $R_{10}$ is H, OH, CN, COOH or CH₂OH.

Finally, those compounds are preferred in which at least one of $R_8$ and $R_{10}$ is OH. Even more preferred compounds of structure (I) are those among the above mentioned in which W, X, Y and Z are —C═, or one of W and X is —N═ and the other, like Y and Z, is —C═; R, $R_1$, $R_5$, $R_7$ and $R_9$ are H; $R_4$ and at least one of $R_8$ and $R_{10}$ is OH, and $R_2$, $R_3$, and $R_6$ independently have the meaning as stated above.

Of these, especially those compounds may be pointed out in which W, X, Y and Z are —C═; R, $R_1$, $R_2$, $R_5$, $R_6$, $R_7$ and $R_9$ are H, $R_4$ is OH; one of $R_8$ and $R_{10}$ is OH and the other is H, and $R_3$ is aryl, heteroaryl, —R"—NHSO₂R', —R"—SO₂NHR', —R"—NHCOR', —R"—CONHR', —R"—COOR' or —R"—OOCR', wherein R' is aryl or heteroaryl, and R" is arylene or heteroarylene, and the aryl and heteroaryl residues may bear a substituent R'" as defined above. Particularly preferred compounds are those in which R" has a 1,3-arylene or 1,3-heteroarylene linkage (i.e., the components —NHSO₂R', —SO₂NHR' etc. of the respective residue are in meta position with respect to the linkage of R" with the central bicyclic ring), or in which $R_3$ is aryl or heteroaryl, and the substituent R'" is in meta position with respect to the linkage of $R_3$ with the central bicyclic ring.

Further preferred among the above mentioned phenyl-naphthalenes are those compounds that bear two hydroxy groups (preferably at positions $R_4$ and $R_{10}$) and a further substituent, especially a residue $R_3$ as defined above. Preferred residues for $R_3$ are explicitly furan-3-yl, pyridin-3-yl, pyridin-4-yl, 4-methoxypyridin-3-yl, phenyl, 3-hydroxyphenyl, 3-aminophenyl and the substituted phenyl residues shown below:

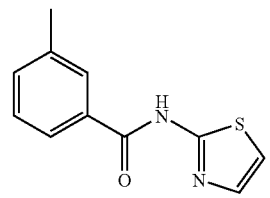

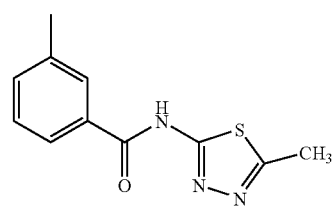

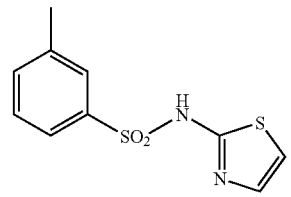

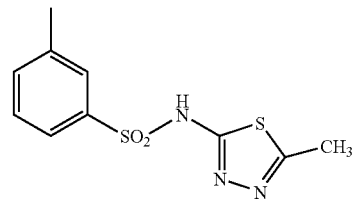

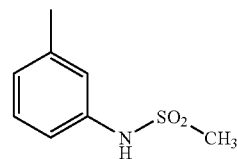

Even more preferred compounds of structure (I) are those mentioned in the following: 3-(2-naphthyl)phenol (3), 3-(6-hydroxy-2-naphthyl)pyridine (4), 3-(6-hydroxy-2-naphthyl)benzoic acid (7), 4-(6-hydroxy-2-naphthyl)benzoic acid (8), N-[3-(6-hydroxy-2-naphthyl)phenyl]acetamide (9), 6-[3-(hydroxymethyl)-phenyl]-2-naphthol (10), 6-[4-(hydroxymethyl)phenyl]-2-naphthol (11), 2-(3-hydroxyphenyl)quinoline-6-ol (12), 3-(quinoline-3-yl)phenol (13), 3-(4-hydroxyphenyl)quinoline-7-ol (15), 3-(3-hydroxyphenyl)quinoline-7-ol (16), 5-(6-hydroxynaphthalene-2-yl)pyridine-3-ol (17), 6-(2-hydroxyphenyl)-2-naphthol (18), 6-(3-hydroxyphenyl)-2-naphthol (19), 6-(3-hydroxyphenyl)-1-naphthol (24), 6-(3-hydroxy-5-methylphenyl)-2-naphthol (26), 5-(6-hydroxy-2-naphthyl)-1,1'-biphenyl-3,4'-diol (27), 6-[3-hydroxy-5-(6-hydroxy-2-naphthyl)-phenyl]-2-naphthol (28), 3-hydroxy-5-(6-hydroxy-2-naphthyl)-N-methylbenzamide (29), 3-hydroxy-5-(6-hydroxy-2-naphthyl)-N- phenylbenzamide (30), (E)-3-[3-hydroxy-5-(6-hydroxy-2-naphthyl)phenyl]-N-methylacrylamide (31), (E)-3-[3-hydroxy-5-(6-hydroxy-2-naphthyl)phenyl]-N-phenylacrylamide (32), 3-[3-hydroxy-5-(6-hydroxy-2-naphthyl)phenyl]-N-methylpropionamide (33), 3-[3-hydroxy-5-(6-hydroxy-2-naphthyl)phenyl]-N-phenylpropionamide (34), N-[2-hydroxy-4-(6-hydroxy-2-naphthyl)phenyl]acetamide (35), N-[2-hydroxy-4-(6-hydroxy-2-naphthyl)phenyl]benzamide (36), 3-hydroxy-7-(3-hydroxyphenyl)-N-methyl-2-naphthamide (37), 3-hydroxy-7-(3-hydroxyphenyl)-N-phenyl-2-naphthamide (38), (E)-3-[2-hydroxy-6-(3-hydroxyphenyl)-1-naphthyl]-N-methylacrylamide (39), (E)-3-[2-hydroxy-6-(3-hydroxyphenyl)-1-naphthyl]-N-phenyl-acrylamide (40), 2-hydroxy-6-(3-hydroxyphenyl)-N-methyl-1-naphthamide (41), 2-hydroxy-6-(3-hydroxyphenyl)-N-phenyl-1-naphthamide (42), 2-hydroxy-N,6-bis(3-hydroxyphenyl)-1-naphthamide (43), [2-hydroxy-6-(3-hydroxyphenyl)-1-naphthyl](morpholino)methanone (44), [2-hydroxy-6-(3-hydroxyphenyl)-1-naphthyl](piperazin-1-yl)methanone (45), 2-hydroxy-6-(3-hydroxyphenyl)-N-(thiazol-2-yl)-1-naphthamide (46), N-(3,4-dimethylisoxazol-5-yl)-2-hydroxy-6-(3-hydroxyphenyl)-1-naphthamide (47), 2-hydroxy-6-(3-hydroxyphenyl)-N-(5-methyl-1,3,4-thiadiazol-2-yl)-1-naphthamide (48), 2-hydroxy-6-(3-hydroxyphenyl)-N-(pyridin-2-yl)-1-naphthamide (49), 2-hydroxy-6-(3-hydroxyphenyl)-N-(pyrimidin-2-yl)-1-naphthamide (50), [2-hydroxy-6-(3-hydroxyphenyl)-1-naphthyl](piperidin-1-yl)methanone (51), 1-bromo-6-(3-hydroxyphenyl)-2-naphthol (52), 7-hydroxy-3-(3-hydroxyphenyl)-1-naphthonitrile (53), 3-hydroxy-7-(3-hydroxyphenyl)-1-naphthonitrile (54), 3-[2-hydroxy-6-(3-hydroxyphenyl)-1-naphthyl]-N-methylpropanamide (55), 6-(3-hydroxyphenyl)-1-phenyl-2-naphthol (56), 1,6-bis(3-hydroxyphenyl)-2-naphthol (57), 1-(3-furyl)-6-(3-hydroxyphenyl)-2-naphthol (58), 6-(3-hydroxyphenyl)-1-(pyridin-3-yl)-2-naphthol (59), 6-(3-hydroxyphenyl)-1-(4-pyridyl)-2-naphthol (60), 6-(3-hydroxyphenyl)-1-(pyrimidin-5-yl)-2-naphthol (61), 6-(3-hydroxyphenyl)-1-(6-methoxy-3-pyridyl)-2-naphthol (62), 3-[2-hydroxy-6-(3-hydroxyphenyl)-1-naphthyl]benzoic acid (63), N-{3-[2-hydroxy-6-(3-hydroxyphenyl)-1-naphthyl]phenyl}methanesulfonamide (64), 6-(3-hydroxyphenyl)-1-(4-morpholinphenyl)-2-naphthol (65), N-{3-[2-hydroxy-6-(3-hydroxyphenyl)-1-naphthyl]phenyl}-acetamide (66), 4-[4-(2-hydroxy-6-(3-hydroxyphenyl)-1-naphthyl]phenylamino)-4-oxobutanoic acid (67), 1-(3-aminophenyl)-6-(3-hydroxyphenyl)-2-naphthol (68), 3-[2-hydroxy-6-(3-hydroxyphenyl)-1-naphthyl]-N-(thiazol-2-yl)benzenesulfonamide (69), 3-[2-hydroxy-6-(3-hydroxyphenyl)-1-naphthyl]-N-(5-methyl-1,3,4-thiadiazol-2-yl)benzenesulfonamide (70), 3-[2-hydroxy-6-(3-hydroxyphenyl)-1-naphthyl]-N-(1,3-thiazol-2-yl)benzamide (71), 3-[2-hydroxy-6-(3-hydroxyphenyl)-1-naphthyl]-N-(5-methyl-1,3,4-thiadiazol-2-yl)benzamide (72), N-{3-[2-hydroxy-6-(3-hydroxyphenyl)-1-naphthyl]phenyl}quinoline-8-sulfonamide (73), 5-chloro-N-{3-[2-hydroxy-6-(3-hydroxyphenyl)-1-naphthyl]-phenyl}thiophene-2-sulfonamide (74), N-{3-[2-hydroxy-6-(3-hydroxyphenyl)-1-naphthyl]phenyl-3-nitrobenzenesulfonamide (75), 2-cyano-N-{3-[2-hydroxy-6-(3-hydroxyphenyl)-1-naphthyl]phenyl}benzenesulfonamide (76), 4-chloro-N-{3-[2-hydroxy-6-(3-hydroxyphenyl)-1-naphthyl]phenyl}-3-nitrobenzenesulfonamide (77), methyl 5-{3-[2-hydroxy-6-(3-hydroxyphenyl)-1-naphthyl]phenylsulfamoyl}-4-methoxythiophene-3-carboxylate (78), N-(4-{3-[2-hydroxy-6-(3-hydroxyphenyl)-1-naphthyl]phenylsulfamoyl}phenyl)acetamide (79), N-{3-[2-hydroxy-6-(3-hydroxyphenyl)-1-naphthyl]phenyl}-5-[2-(methylsulfanyl)pyrimidin-4-yl]thiophene-2-sulfonamide (80), N-{3-[2-hydroxy-6-(3-hydroxyphenyl)-1-naphthyl]phenyl}-4-nitrobenzenesulfonamide (81), 4-bromo-N-{3-[2-hydroxy-6-(3-hydroxyphenyl)-1-naphthyl]phenyl}-2-(trifluoromethoxy)benzenesulfonamide (82), 2-nitro-N-{3-[2-hydroxy-6-(3-hydroxyphenyl)-1-naphthyl]phenyl}-4-(trifluoromethyl)benzenesulfonamide (83), N-{3-[2-hydroxy-6-(3-hydroxyphenyl)-1-naphthyl]phenyl}imidazo[2,1-b][1,3]thiazole-5-sulfonamide (84), 4,5-dibromo-N-{3-[2-hydroxy-6-(3-hydroxyphenyl)-1-naphthyl]phenyl}thiophene-2-sulfonamide (85), N-{3-[2-hydroxy-6-(3-hydroxyphenyl)-1-naphthyl]-phenyl}-1,3-benzothiazole-6-sulfonamide (86), N-{3-[2-hydroxy-6-(3-hydroxyphenyl)-1-naphthyl]phenyl}thiophene-2-sulfonamide (87), 2,2,2-trifluoro-N-[2-(4-{3-[2-hydroxy-6-(3-hydroxyphenyl)-1-naphthyl]phenylsulfamoyl}phenyl)ethyl]acetamide (88), 4-bromo-2,5-difluoro-N-{3-[2-hydroxy-6-(3-hydroxyphenyl)-1-naphthyl]phenyl}benzenesulfonamide (89), 3-[2-hydroxy-6-(3-hydroxyphenyl)-1-naphthyl]-N-(methylsulfonyl)benzamide (90), 6-(3-hydroxyphenyl)-1-(phenylsulfonyl)-2-naphthol (91), 6-(3-hydroxyphenyl)-1-(4-methylphenyl)sulfonyl)-2-naphthol (92) and pharmacologically acceptable salts thereof. Preferably, the compounds are selected from compounds (19), (56), (57), (59), (60), (64), (68) and (69) and pharmacologically acceptable salts thereof.

The process for the preparation of the compound defined in (2) and having the structure (I) according to embodiment (3) of the invention is effected by means of a Suzuki reaction, comprising the reaction of compounds (II) and (III) in the presence of Pd(PPh$_3$)$_4$ or a comparable Pd catalyst. The coupling may be effected according to methods A, B or C as outlined below.

In method A, tetrakis(triphenylphosphine)palladium (0) (0.1 eq) and boric acid (1 eq) are added to an oxygen-free mixture of halogen derivative (1 eq) in toluene/ethanol 2/1 or DME and 2% sodium carbonate solution (2 eq) under a nitrogen atmosphere. The reaction mixture is refluxed at 80° C. for up to 24 h.

In method B, the halogen derivative (0.2 mmol), boric acid (0.4 mmol), K$_2$CO$_3$ (0.6 mmol) and Pd(OAc)$_2$ are suspended in 5 ml of DME/water/ethanol 73/2 and exposed to microwave radiation at 150° C. for 300 s.

In method C, the bromo derivative (1 eq), boric acid (1.3 eq) and Pd(PPh$_3$)$_4$ (0.05 eq) are suspended in 1.5 ml of DMF in a suitable reaction vessel using a magnetic stirrer, NaHCO$_3$ (3 eq) in 1.5 ml of water is added, and the mixture is exposed to 100 W microwave radiation at 140° C. for 15 min.

The above stated amounts, times and temperatures are preferred values that may of course be varied by the skilled person without significant losses of yield.

The preparation of the compounds according to the invention by means of method A is further illustrated in the following Scheme.

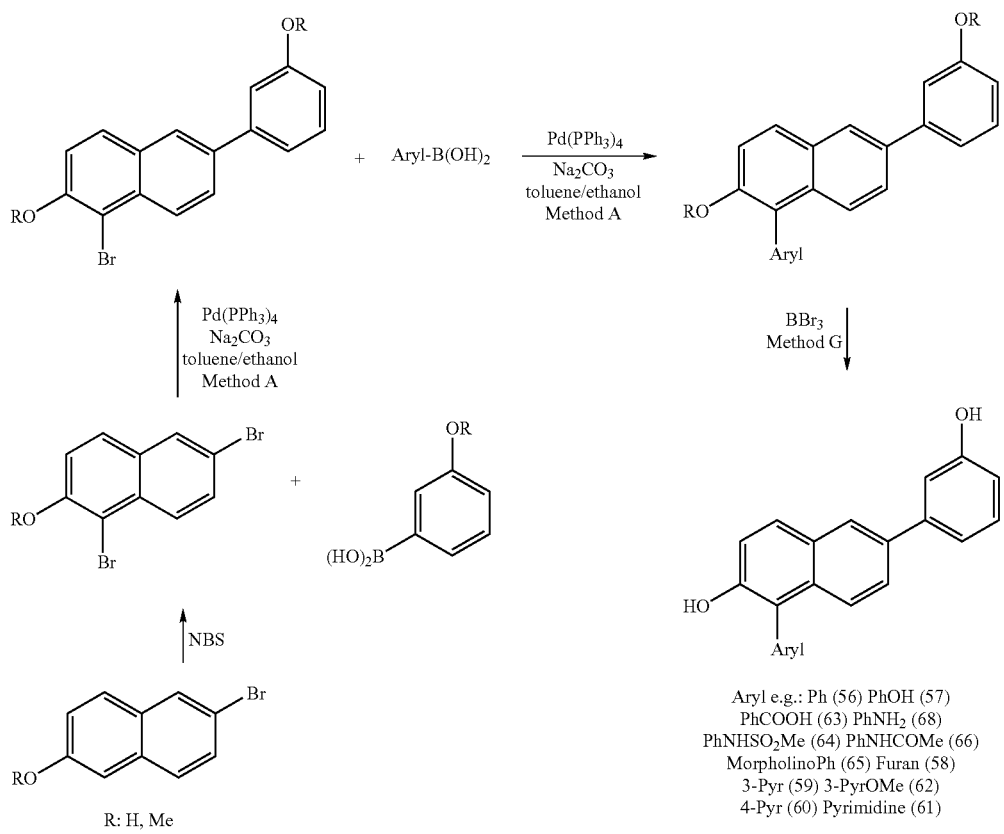

Aryl e.g.: Ph (56) PhOH (57)
PhCOOH (63) PhNH₂ (68)
PhNHSO₂Me (64) PhNHCOMe (66)
MorpholinoPh (65) Furan (58)
3-Pyr (59) 3-PyrOMe (62)
4-Pyr (60) Pyrimidine (61)

For the use according to embodiment (1) or the medicament of pharmaceutical composition according to embodiment (3) and the process according to embodiment (5) of the invention, the compounds of the present invention are processed into a suitable dosage form. Such processing is not subject to any limitations, since the compounds can be administered to the patient in any dosage form familiar to the skilled person, the oral route of administration being preferred, however.

The quantity of active substance administered, i.e., the dose employed, depends on the kind and severity of the disease to be treated, the dosage form and therapy form, the age and constitution of the patient, and is individually adapted to the concrete situation by the attending physician within the scope of its general technical skill.

The invention is now further illustrated by means of the following Examples, which do not however limit the invention.

EXAMPLES

General Information and Methods

Chemical designations: The chemical designations of the compounds are in accordance with IUPAC nomenclature.

Thin-layer chromatography (TLC): For thin-layer chromatography, Alugram® SilG/UV$_{254}$ plates were used, which are plates having a thickness of 0.2 mm coated with silica gel 60 and a fluorescence indicator, supplied by Macherey-Nagel. For preparative TLC, glass plates coated with silica gel 60 and a fluorescence indicator (SilG25/UV$_{254}$) from Macherey-Nagel were used. The layer thickness was 0.25 mm.

Column chromatography (CC): Silica gel $^{35}/_{40}$-$^{63}/_{70}$ µm from Merck served as a packing material for the column chromatography that was performed under pressure, and silica gel 60, 0.05/0.063/0.07-0.2 mm served for the column chromatography that was performed with no pressure.

Reactions in the microwave oven: The microwave oven used for the synthesis was an Emrys Optimizer Workstation.

Infrared spectroscopy (IR): The IR spectra of the neat substances were recorded with a Bruker "Vektor 33", and the wave number ν is stated in 1/cm.

Nuclear resonance spectroscopy (NMR): The NMR spectra were recorded with a Bruker AM 500 at 300 K, $^1$H NMR spectra being measured at 500 MHz, and $^{13}$C NMR spectra being measured at 125 MHz. The measurements were performed in tetradeuteromethanol (CD$_3$OD), deuterochloroform (CDCl$_3$) or deuterated DMSO, and their peaks appearing in the spectrum were at the same time used as references (CDCl$_3$: δ=7.24 ppm in $^1$H NMR and δ=77 ppm in $^{13}$C NMR, CD$_3$OD: δ=3.35 ppm in $^1$H NMR and δ=49.3 ppm in $^{13}$C NMR). The chemical shifts are stated in δ values (ppm), and the coupling constants (J) are stated in Hertz (Hz). The usual abbreviations were used: s=singlet, d=doublet, dd=doublet of doublet, ddd=doublet of doublet of doublet, t=triplet, m=multiplet, bs=broad singlet.

Mass spectroskopy (LC/MS-MS): The mass spectra were measured with a TSQ Quantum (Thermo Finnigen) (ESI=electrospray ionization).

Chemicals: Chemicals for synthesis were purchased from Aldrich, Acros and Fluka and used without any further purification.

Abbreviations: CD$_3$OD=methanol-d$_4$; CDCl$_3$=chloroform-d$_3$; DMSO=Dimethylsulfoxide; RT=room temperature; BTMABr$_3$=benzyltrimethylammonium bromide.

Preparation of Intermediates and Compounds According to the Invention

1.) 3-Bromo-7-methoxyquinoline

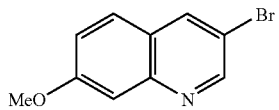

For the synthesis of this starting compound, 1.80 g (12.3 mmol, 1.1 eq) of bromomalondialdehyde was first dissolved in 30 ml of ethanol, and 1.25 ml of m-anisidine was added. This reaction mixture is stirred over night at RT and, after the addition of acetic acid (20 ml), at 100° C. for 10 days. The solvent is subsequently removed in vacuum on a rotary evaporator, and the residual solid is partitioned between a water and an ethyl acetate phase. The aqueous phase is made alkaline with an ammonia solution, and insoluble particles were filtered off. The filtrate is extracted with ethyl acetate, and the organic phase is dried over MgSO$_4$, filtered, and the solvent is removed in vacuum on a rotary evaporator. The product was purified by column chromatography with a mixture of hexane/ethyl acetate 8/2 as the eluent in a yield of 20% (700 mg).

C$_{10}$H$_8$BrNO; MW 237/239; $^1$H-NMR (CDCl$_3$): δ 8.76 (d, J=2.2 Hz, 1H), 8.15 (d, J=2.2 Hz, 1H), 7.55 (d, J=9.1 Hz, 1H), 7.32 (d, J=2.5 Hz, 1H), 7.15 (dd, J=2.5 Hz, J=8.8 Hz, 1H), 3.88 (s, 3H, OMe); $^{13}$C-NMR (CDCl$_3$): δ 159.9, 150.4, 147.1, 135.9, 126.9, 123.4, 119.9, 113.6, 106.3, 54.6; IR: 2961, 1620, 1581, 1491, 1462, 1417, 1261, 1027, 796 1/cm; MS (ESI): 238-240 (M+H)$^+$

2.) 5-Oxo-5,6,7,8-tetrahydronaphthalene-2-yl trifluoromethanesulfonate

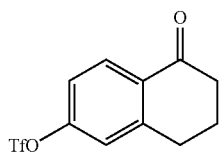 [SMILES: O=C1CCCc2cc(OS(=O)(=O)C(F)(F)F)ccc21]

2 g of 6-hydroxytetralone (12.3 mmol, 1 eq) is suspended under N$_2$ in 90 ml of dichloromethane and cooled to 0° C. To the reaction mixture, dry pyridine (1.4 ml, 17.26 mmol, 1.4 eq) is added, followed by trifluoromethanesulfonic anhydride (2.33 ml, 4.17 g, 14.79 mmol, 1.2 eq). After 30 min at 0° C., the reaction is stopped by adding a saturated sodium carbonate solution, and washed with water. The organic phase is dried over MgSO$_4$, filtered, and the solvent is removed in vacuum on a rotary evaporator. The brown oil obtained was used for further synthesis without further purification (3.7 g, 98% yield).

C$_{11}$H$_9$F$_3$O$_4$S; MW 294; $^1$H-NMR (CDCl$_3$): δ 8.12 (d, J=8.5 Hz, 1H), 7.20-7.17 (d, J=12.0 Hz, 2H); 3.01 (t, J=6.0 Hz, 2H); 2.67 (t, J=6.3 Hz, 2H); 2.19-2.14 (q, J=7.3 Hz, 2H); $^{13}$C-NMR (CDCl$_3$): δ 196.4, 152.4, 147.1, 132.40, 130.0, 121.4, 119.7, 38.8, 29.7, 22.9; IR: 2937, 2851, 1692, 1605, 1425, 1219, 897 1/cm

3.) 2,6-Dibromo-4-methoxyaniline

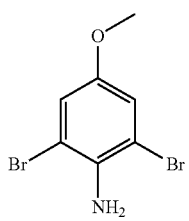

To a solution of p-anisidine (790 mg, 6.42 mmol, 1 eq) in a mixture of 50 ml of dichloromethane and 20 ml of methanol, BTMABr$_3$ (5 g, 12.82 mmol, 2 eq) and 2 g of calcium carbonate are added. The reaction mixture is stirred at RT for 1 h, and then the calcium carbonate is filtered off, and water is added. The aqueous phase is extracted with diethyl ether, and the combined organic phases are dried over magnesium sulfate, filtered and evaporated to dryness in vacuum on a rotary evaporator. Purification by column chromatography with hexane/ethyl acetate 95/5 as the eluent yielded the desired product in a yield of 50% (890 mg).

C$_7$H$_7$Br$_2$NO; MW 279/281/283; $^1$H-NMR (CDCl$_3$): δ 7.06 (s, 2H), 4.18 (bs, 1H), 3.71 (s, 3H); $^{13}$C-NMR (CDCl$_3$): δ 151.1, 135.2, 117.0, 108.1, 55.1; IR: 3402, 3294, 1593, 1552, 1480 1/cm

4.) 1,3-Dibromo-5-methoxybenzene

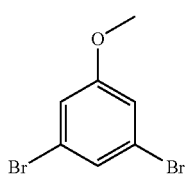

To a solution of 2,6-dibromo-4-methoxyphenylamine (3 g, 10.67 mmol, 1 eq) in 10 ml of toluene cooled at 0° C. are added 6.6 ml of concentrated sulfuric acid and 17.5 ml of H$_3$PO$_2$ 50% (15 eq). To the reaction mixture, sodium nitrite (1.47 mg, 21.35 mmol, 2 eq) is added, and all is stirred at 0° C. for 4.5 h. After neutralization with a sodium hydroxide solution, extraction with diethyl ether is performed. The organic phase is dried over magnesium sulfate, filtered and evaporated to dryness on a rotary evaporator. Purification of the raw product was not necessary (yield 96%, 2.7 g).

C$_7$H$_6$Br$_2$O; MW 264/266/268; $^1$H-NMR (CDCl$_3$): δ 7.23-7.22 (m, 1H), 6.97 (s, 1H), 6.96 (s, 1H), 3.75 (s, 3H); $^{13}$C-NMR: δ 160.8, 126.4, 123.1, 116.5, 55.7; IR: 2925, 1599, 1569, 1464 1/cm

5.) (E)-3-(3-Bromo-5-methoxyphenyl)acrylic acid

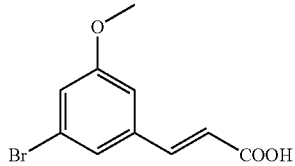

To a solution of 1,3-dibromo-5-methoxybenzene (9.18 mmol, 1 eq) in 2 ml of xylene under a nitrogen atmosphere, acrylic acid (0.63 ml, 9.18 mmol, 1 eq), Pd(OAc)$_2$ (1 mole %, 20.66 mg), triphenylphosphine (4 mole %, 69.2 mg) and triethylamine (19.278 ml, 2.7, 2.1 eq) are added. The reaction mixture is stirred at 100° C. for 11 h. Thereafter, 20 ml of water and 2 g of sodium carbonate were added, and the mixture was stirred at 100° C. for some minutes. The aqueous phase was subsequently separated and acidified. The precipitate that formed was dried and purified by means of column chromatography (eluent hexane/ethyl acetate 1/1) to obtain the desired product in a yield of 32% (751 mg).

C$_{10}$H$_9$Br$_3$O; MW 256/258; $^1$H-NMR (CD$_3$OD): δ 7.61 (d, J=16.1 Hz, 1H), 7.38-7.37 (m, 1H), 7.17-7.16 (m, 2H), 6.53 (d, J=16.1 Hz, 1H), 3.87 (s, 3H); $^{13}$C-NMR (CD$_3$OD): δ 169.8, 162.3, 144.5, 138.9, 124.2, 121.4, 120.0, 113.4, 56.2

6.) 4-Bromo-2-methoxy-6-methylaniline

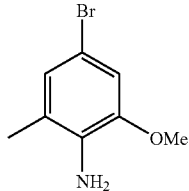

2-Methoxy-6-methylaniline (100 mg, 0.73 mmol, 1 eq) is dissolved in a mixture of 10 ml of dichloromethane and 4 ml of methanol. After the addition of 284.7 mg (0.73 mmol, 1 eq) of BTMBr$_3$ and 292 mg (292 mmol) of calcium carbonate, the mixture is stirred at room temperature for one hour.

The calcium carbonate is subsequently filtered off, and 10 ml of water is added. The hydrophilic and lipophilic phases are separated, and the water phase is extracted four times with ether. The combined organic extracts are dried over magnesium sulfate, filtered, and the solvent is removed in vacuum on a rotary evaporator. Purification of the product was not necessary (quantitative yield, 157 mg).

C$_8$H$_{10}$BrNO; MW 215/217; $^1$H-NMR (CDCl$_3$): δ 6.83-6.82 (m, 1H), 6.77 (d, J=1.9 Hz, 1H), 3.81 (s, 3H), 2.12 (s, 3H); $^{13}$C-NMR (CDCl$_3$): δ 147.5, 133.4, 125.1, 123.8, 111.5, 109.0, 55.8, 17.0; IR: 3463, 3373, 2973, 1594, 1486, 1409 1/cm; MS (ESI): 216-218 (M+H)$^+$

7.) 1-Bromo-3-methoxy-5-methylbenzene

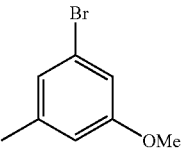

The reaction is performed in a water/ice bath. 500 mg (2.31 mmol, 1 eq) of 4-bromo-2-methoxy-6-methylaniline is dissolved in a mixture of 7 ml of acetic acid and 3 ml of water, followed by adding 0.8 ml of concentrated hydrochloric acid (37%) and 207 mg (3.00 mmol, 1.5 eq) of sodium nitrite dissolved in 1 ml of water. The mixture is stirred for 30 min and subsequently added to 8 ml of ice-cooled 50% by weight hypophosphoric acid. The reaction is stirred at 0° C. for 8 hours and allowed to stand at RT over night.

For the processing, the mixture is extracted with ethyl acetate, dried over magnesium sulfate, filtered, and the solvent is removed in vacuum on a rotary evaporator. The raw product was not further purified (yield 90%, 418 mg).

C$_8$H$_9$BrO; MW 200/202; $^1$H-NMR (CDCl$_3$): δ 6.45 (s, 1H), 6.39 (s, 1H), 6.18 (s, 1H), 3.30 (s, 3H), 1.83 (s, 3H); $^{13}$C-NMR (CDCl$_3$): δ 160.2, 141.0, 124.5, 122.4, 114.1, 113.9, 55.4, 21.2; IR: 2925, 1599, 1569, 1464 1/cm

8.) 4-Bromo-2-methoxyaniline

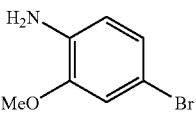

o-Anisidine (0.18 ml, 20 mg, 1.63 mmol, 1 eq) is dissolved in a mixture of 10 ml of dichloromethane and 4 ml of methanol. Subsequently, TBMABr$_3$ (761 mg, 1.95 mmol, 1.2 eq) and calcium carbonate (650 mg, 6.50 mmol, 4 eq) are added, and the mixture is stirred at RT for 2 h. The calcium carbonate is filtered off, and water is added. The aqueous phase is extracted with dichloromethane, and the combined organic phases are dried over magnesium sulfate, filtered and evaporated to dryness on a rotary evaporator. Purification by column chromatography with dichloromethane/hexane 7/3 as the eluent yielded the desired product in a yield of 75%, 247 mg.

C$_7$H$_8$BrNO; MW 202; $^1$H-NMR (CDCl$_3$): δ 6.89 (m, 2H), 6.58 (d, J=7.9 Hz, 1H), 3.92 (bs, 1H), 3.82 (s, 3H); $^{13}$C-NMR (CDCl$_3$): δ 148.0, 134.9, 123.7, 115.9, 113.8, 109.9, 56.7; IR: 3470, 3375 (amine), 1616, 1503, 1409 (phenyl) 1/cm

9.) 7-Methoxy-1-naphthonitrile

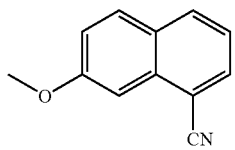

7-Methoxy-1-tetralone (8.16 g, 46 mmol, 1 eq) and ZnI$_2$ (0.365 g, 1 mmol, 0.025 eq) were dissolved in 25 ml of toluene and heated at 45° C. Trimethylsilylcyanide (TMSCN) (5.0 g, 50 mmol, 1.1 eq) is added over a period of 20 min, and all is refluxed for 3 h. After cooling the mixture at about 35° C., pyridine (5.5 ml, 69 mmol, 1.5 eq) and POCl$_3$ (6.4 ml, 69 mmol, 1.5 eq) are added, and the mixture is boiled under reflux for another 6 h. Thereafter, 80 ml of a 3 N NaOH cooled at 3° C. is added over a period of 15 min. The aqueous phase is extracted with 48 ml of toluene, and the organic phase is washed twice with 40 ml of 1 N NaOH, once with 40 ml of water, three times with 40 ml of 3 N HCl, once with 40 ml of water, once with 40 ml of a saturated NaHCO$_3$ solution and once with a saturated sodium chloride solution. After the addition of 2,3-dichloro-5,6-dicyano-1,4-benzoquinone (DDQ) (8.41 g, 37 mmol, 0.8 eq) over 20 min, the organic phase is boiled under reflux for 2 h. After cooling, the precipitate was filtered off and washed twice with 32 ml of 1 N NaOH and once with 32 ml of a saturated sodium chloride solution. Drying of the precipitate yielded the desired product in a yield of 78%, 6.6 g.

C$_{12}$H$_9$NO; MW 183; R$_f$ value (hexane/ethyl acetate 8/2): 0.7; $^1$H-NMR (CDCl$_3$): δ 7.97 (d, J=8.2 Hz, 1H), 7.85 (dd, J=0.9 Hz, J=6.9 Hz, 1H), 7.79 (d, J=9.1 Hz, 1H), 7.45 (d, J=2.2 Hz, 1H), 7.36 (dd, J=8.2 Hz, J=7.3 Hz, 1H), 7.24 (dd, J=2.5 Hz, J=8.8 Hz, 1H), 3.98 (s, 3H); IR: 3003, 2943, 2839, 2218, 1505, 1259, 1243, 1025 1/cm

10.) 3-Bromo-7-methoxy-1-naphthonitrile

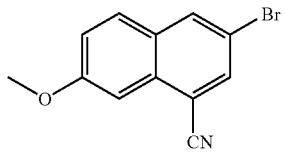

7-Methoxy-1-naphthonitrile (6.6 g, 36 mmol, 1 eq) is dissolved in 66 ml of acetic acid and heated at 45° C. Over a period of 15 min, bromine (34 g, 10.9 ml, 213 mmol, 5.9 eq) is slowly added in such a way that the temperature does not exceed 55° C., and the mixture is boiled under reflux for 3 h. After cooling, an NaHSO$_3$ solution (17.16 g in 40 ml of water) is added in such a way that the temperature does not exceed 40° C. The precipitate is filtered off, washed with water, dried and dissolved in 60 ml of acetic acid. Tin chloride dihydrate (13.7 g, 72 mmol, 2 eq) is added, and 28 ml of conc. HCl is added dropwise over a period of 90 min at 100° C. The reaction mixture is stirred over night, the resulting precipitate is filtered off and washed twice each with 11 ml of 1% HCl and water (yield 70%, 6.6 g).

C$_{12}$H$_8$BrNO; MW: 261/263; R$_f$ value (hexane/ethyl acetate 8/2): 0.8; $^1$H-NMR (CDCl$_3$): δ 8.12 (d, J=1.9 Hz, 1H), 7.92 (d, J=1.9 Hz, 1H), 7.71 (d, J=8.8 Hz, 1H), 7.40 (d, J=2.5 Hz, 1H), 7.26 (dd, J=2.5 Hz, J=9.1 Hz, 1H), 3.97 (s, 3H); IR: 3355, 2835, 2221 1/cm

11.) 8-Cyano-6-methoxynaphthalene-2-yl trifluoromethanesulfonate

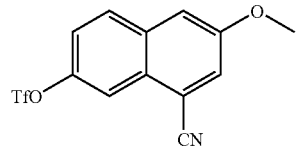 [SMILES: COc1cc(C#N)c2cc(OS(=O)(=O)C(F)(F)F)ccc2c1]

The compound was prepared according to the protocol in J. Med. Chem., 2005, 48, 3953-3979.

12.) 6-Bromo-2-methoxy-1-naphthaldehyde

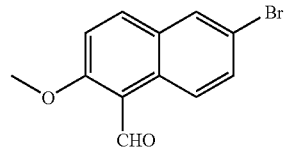

9.7 ml of TiCl$_4$ (2.1 eq) and 4.2 ml of dichloromethyl methyl ether (1.1 eq) are dissolved in 20 ml of dichloromethane at 0° C. A solution of 10 g of 2-bromo-6-methoxynapthalene (1 eq) is added dropwise in such a way that the temperature does not exceed 5° C. The reaction mixture is stirred at RT over night, followed by the addition of 300 ml of 1% HCl. The organic and aqueous phases are separated, and the aqueous phase is extracted with dichloromethane. The combined organic phases are washed with saturated sodium chloride solution, dried over magnesium sulfate and evaporated to dryness on a rotary evaporator to obtain the desired product in quantitative yield (11 g).

C$_{12}$H$_9$BrO$_2$; MW 264/266; $^1$H-NMR (CDCl$_3$): δ 10.80 (s, 1H), 9.16 (d, J=9.1 Hz, 1H), 7.94 (d, J=9.1 Hz, 1H), 7.90 (d, J=9.1 Hz, 1H), 7.66 (dd, J=2.2 Hz, J=9.4 Hz, 1H), 7.30 (d, J=9.1 Hz, 1H), 4.05 (s, 3H); $^{13}$C-NMR (CDCl$_3$): δ 191.6, 163.8, 136.3, 132.8, 130.0, 129.7, 126.8, 118.5, 116.6, 113.7, 56.6; IR: 2973, 2887, 2807, 1661 1/cm

13.) 1,6-Dibromo-2-naphthol

6-Bromo-2-naphthol (500 mg, 2.242 mmol, 1 eq) and NBS (558.7 mg, 3.319 mmol, 1.4 eq) are stirred at RT in 4.4 ml of acetone and 22 µl of 1 N HCl for 15 min. Ethyl acetate is added, and this organic phase is washed three times with 1 N HCl. After drying over magnesium sulfate, filtering and concentrating in vacuum on a rotary evaporator, the desired product is obtained in quantitative yield (677 mg).

$C_{10}H_6Br_2O$; MW 300/302/304; $^1$H-NMR (CDCl$_3$): δ 7.90 (d, J=1.8 Hz, 1H), 7.87 (d, J=8.8 Hz, 1H), 7.61 (d, J=8.8 Hz, 1H), 7.59 (dd, J=2.1 Hz, J=9.1 Hz, 1H), 7.24 (d, J=8.8 Hz, 1H); $^{13}$C-NMR (CDCl$_3$): δ 177.5, 151.0, 131.0, 130.6, 130.1, 128.4, 128.3, 127.2, 118.0, 106.1; IR: 3443, 1688, 1617, 1586, 1382, 1209, 1183, 1130 1/cm

14.) 1,6-Dibromo-2-methoxynaphthalene

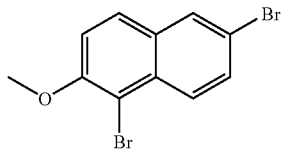

6-Bromo-2-methoxynaphthalene (5.9 g, 24.81 mmol, 1 eq) and NBS (4.41, 24.81 mmol, 1 eq) are boiled in 50 ml of THF under reflux for 2 h. After washing with 1 N HCl, the organic phase is dried over magnesium sulfate, filtered and concentrated in vacuum on a rotary evaporator. The compound is obtained in quantitative yield (7.8 g).

$C_{11}H_8Br_2O$; MW 314/316/318; $^1$H-NMR (CDCl$_3$): δ 7.98 (d, J=8.8 Hz, 1H), 7.84 (d, J=2.1 Hz, 1H), 7.63 (d, J=9.1 Hz, 1H), 7.50 (dd, J=2.1 Hz, J=9.1 Hz, 1H), 7.20 (d, J=9.1 Hz, 1H), 3.93 (s, 3H); $^{13}$C-NMR (CDCl$_3$): δ 182.9, 157.9, 135.6, 134.8, 134.5, 133.7, 132.0, 131.9, 118.4, 60.9; IR: 2964, 1708, 1587, 1490, 1344, 1272, 1070 1/cm

15.) 3-[3-Methoxy-5-(6-methoxynaphthalene-2-yl)phenyl]propionic acid

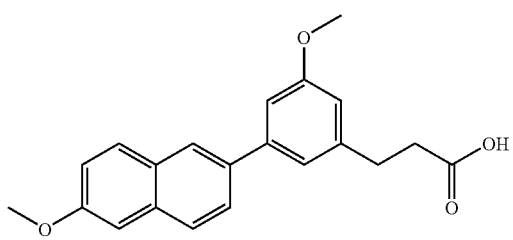 [SMILES: COc1cc(CCC(=O)O)cc(-c2ccc3cc(OC)ccc3c2)c1]

A suspension of (E)-3-[3-methoxy-5-(6-methoxynaphthalene-2-yl)phenyl]acrylic acid (100 mg, 0.30 mmol, 1 eq) and Pd(OH)$_2$ (2.82 mg) in ethanol (1 ml) and THF (0.4 ml) is stirred at RT under a hydrogen atmosphere for 23 h. The reaction mixture is filtered and concentrated in vacuum on a rotary evaporator to obtain the compound in quantitative yield (100 mg).

$C_{21}H_{20}O_4$; MW 336; $^1$H-NMR (DMSO): δ 8.16 (d, J=1.6 Hz, 1H), 7.90 (d, J=8.8 Hz, 1H), 7.88 (d, J=8.5 Hz, 1H), 7.79 (dd, J=1.9 Hz, J=8.5 Hz, 1H), 7.35 (d, J=2.5 Hz, 1H), 7.23 (m, 1H), 7.19 (dd, J=2.5 Hz, J=8.8 Hz, 1H), 7.14-7.13 (m, 1H), 6.82 (m, 1H), 3.89 (s, 3H), 3.83 (s, 3H), 2.90-2.87 (m, 2H), 2.63-2.60 (m, 2H); $^{13}$C-NMR (DMSO): δ 163.1, 157.4, 150.3, 143.0, 135.1, 129.7, 128.7, 126.7, 119.2, 55.2, 55.1, 34.3, 30.4; IR: 2956, 1702, 1594, 1198, 1152 1/cm

16.) 3-Methoxy-5-(6-methoxynaphthalene-2-yl)benzoic acid

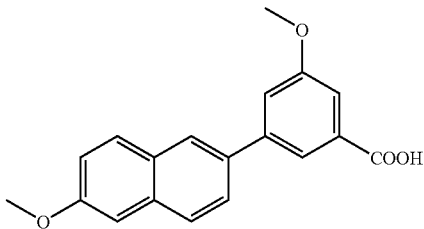 [SMILES: COc1cc(C(=O)O)cc(-c2ccc3cc(OC)ccc3c2)c1]

To a mixture of 2-methoxy-6-(3-methoxy-5-methylphenyl)naphthalene (1.3 g, 4.7 mmol, 1 eq) in 3.3 ml of pyridine and 10 ml of water is added potassium permanganate (3.2 eq) at 75° C. in small portions. The reaction mixture is stirred at 75° C. for 42 h and subsequently filtered while still hot. By acidifying the aqueous phase and drying the precipitate formed, the desired compound could be obtained in a yield of 50%, 724 mg.

$C_{19}H_{16}O_4$; MW 308; $^1$H-NMR (CD$_3$OD): δ 8.08 (d, J=1.6 Hz, 1H), 8.01 (m, 1H), 7.90 (d, J=9.1, 1H), 7.88 (d, J=9.1, 1H), 7.77 (dd, J=1.9 Hz, J=8.5 Hz, 1H), 7.58 (dd, J=1.3 Hz, J=2.5 Hz, 1H), 7.52 (dd, J=1.6 Hz, J=2.5 Hz, 1H), 7.30 (d, J=2.2 Hz, 1H), 7.20 (dd, J=2.5 Hz, J=9.1 Hz, 1H), 3.97 (s, 3H), 3.70 (s, 3H); IR: 2936, 1690, 1591, 1489, 1459 1/cm

17.) 3-Methoxy-7-(3-methoxyphenyl)-2-naphthoic acid

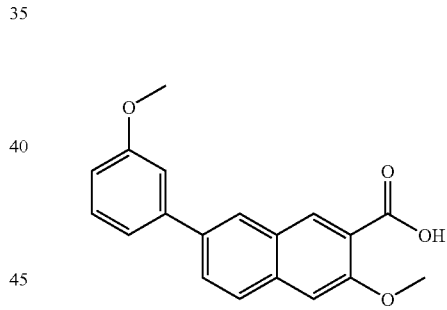

Lithium hydroxide (477 mg, 11.37 mmol, 3.5 eq) is added to a solution, cooled at 0° C., of 3-methoxy-7-(3-methoxyphenyl)-2-naphthoic acid methyl ester (1.05 g, 3.25 mmol, 1 eq) in a mixture of THF/water 1/1 (40 ml), and the reaction mixture was boiled under reflux for 1.5 h. The solvent is removed in vacuum on a rotary evaporator, and 2 N HCl is added to the residue. This phase is extracted with dichloromethane. The combined organic phases are dried over magnesium sulfate, filtered and concentrated in vacuum on a rotary evaporator.

The residual solid is the desired product (quantitative yield, 1 g).

$C_{20}H_{18}NO_4$; MW 322; $^1$H-NMR (CDCl$_3$): δ 8.83 (s, 1H), 8.08 (s, 1H), 7.84 (m, 2H), 7.39 (t, J=7.9 Hz, 1H), 7.32 (s, 1H), 7.24 (d, J=7.6 Hz, 1H), 7.20 (t, J=2.2 Hz, 1H), 6.93 (dd, J=2.5 Hz, J=8.2 Hz, 1H), 4.18 (s, 3H), 3.88 (s, 3H); $^{13}$C-NMR (CDCl$_3$): 165.2, 160.2, 154.4, 136.6, 135.8, 130.0, 129.3, 127.2, 127.1, 119.7, 118.3, 113.1, 113.0, 107.0, 56.8, 55.4; IR: 3262, 2942, 2837, 1733, 1600, 1490, 1200 1/cm

18.) 2-Methoxy-6-(3-methoxyphenyl)-1-naphthoic acid

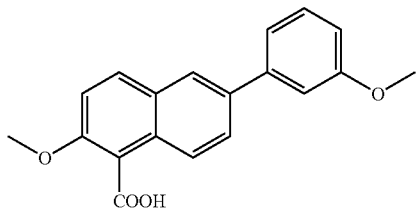

200 mg of the compound 2-methoxy-6-(3-methoxyphenyl)-1-naphthaldehyde (0.68 mmol, 1 eq) is dissolved in a mixture of 8 ml of water and 17 ml of acetone. To the cooled reaction mixture, amidosulfonic acid ($H_2NSO_3H$) (1.51 mmol, 2.21 eq) and sodium hypochlorite (0.78 mmol, 1.14 eq) are added. After stirring for 30 min, the acetone is removed in vacuum on a rotary evaporator, and dichloromethane is added. The organic and aqueous phases are separated, and the organic phase is washed three times with saturated sodium chloride solution. After drying and concentrating the organic phase on a rotary evaporator, the desired product was obtained as a yellow solid in quantitative yield (209 mg).

$C_{19}H_{16}O_4$; MW 308; $^1$H-NMR ($CDCl_3$): δ 8.54 (d, J=9.1 Hz, 1H), 8.04 (d, J=9.1 Hz, 1H), 7.98 (d, J=1.9 Hz, 1H), 7.83 (dd, J=1.9, Hz, J=8.8 Hz, 1H), 7.40 (t, J=7.9 Hz, 1H), 7.35 (d, J=8.8 Hz, 1H), 7.29 (m, 1H), 7.23 (m, 1H), 6.94 (ddd, J=0.9 Hz, J=2.8 Hz, J=8.2 Hz, 1H), 4.13 (s, 3H), 3.90 (s, 3H); IR: 3061, 2993, 2938, 1729, 1672, 1597, 1576, 1493, 1282, 1256, 1210, 1073 1/cm

19.) (E)-3-(2-Methoxy-6-(3-methoxyphenyl)naphthalene-1-yl)acrylic acid ethyl ester

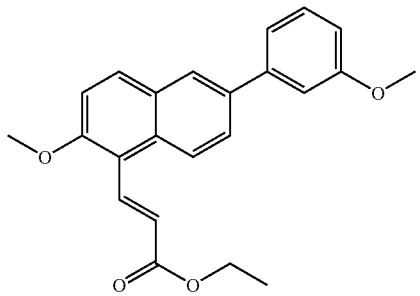

NaH (55-65%) (9.9 mg, 0.21 mmol, 1.2 eq) is suspended under a nitrogen atmosphere in 5 ml of dry DME. Phosphonoacetate (46.0 mg, 0.21 mmol, 1.2 eq) is added, and after stirring for 15 min, 2-methoxy-6-(3-methoxyphenyl)-1-naphthaldehyde (50 mg, 0.17 mmol, 1 eq) is added. The reaction mixture is stirred at RT for 1 h, water is then added, the phases are separated, and the aqueous phase is extracted with ethyl acetate. The combined organic phases are dried over magnesium sulfate, filtered and concentrated in vacuum on a rotary evaporator. The resulting solid is the desired product (quantitative yield, 61.5 mg).

$C_{23}H_{22}O_4$; MW 362; $R_f$ value (hexane/ethyl acetate 2/1): 0.5; $^1$H-NMR ($CDCl_3$): δ 8.36 (d, J=16.1 Hz, 1H), 8.24 (d, J=8.8 Hz, 1H), 7.97 (d, J=1.8 Hz, 1H), 7.89 (d, J=9.1 Hz, 1H), 7.77 (dd, J=2.1 Hz, J=8.8 Hz, 1H), 7.38 (t, J=7.9 Hz, 1H), 7.30 (d, J=8.5 Hz, 1H), 7.29-7.27 (m, 1H), 7.22-7.22 (m, 1H), 6.91 (ddd, J=0.9 Hz, J=2.4 Hz, J=8.2 Hz, 1H), 6.78 (d, J=16.1 Hz, 1H), 4.31 (q, J=7.0 Hz, 2H), 4.00 (s, 3H), 3.88 (s, 3H), 1.37 (t, J=7.0 Hz, 3H); $^{13}$C-NMR ($CDCl_3$): δ 167.9, 160.1, 156.8, 142.1, 137.5, 136.3, 132.0, 131.8, 129.9, 129.2, 127.0, 126.3, 123.9, 123.4, 119.7, 116.6, 113.1, 112.9, 112.7, 60.4, 56.2, 55.3, 14.4; IR: 2937, 2839, 1712, 1705, 1273, 1170 1/cm

20.) (E)-3-(2-Methoxy-6-(3-methoxyphenyl)naphthalene-1-yl)acrylic acid

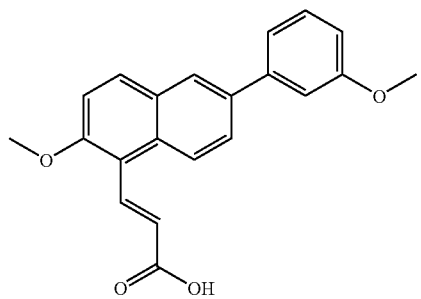

Lithium hydroxide (407.7 mg, 9.94 mmol, 6 eq) is added to a solution, cooled at 0° C., of (E)-3-(2-methoxy-6-(3-methoxyphenyl)naphthalene-1-yl)acrylic acid ethyl ester (600 mg, 1.66 mmol, 1 eq) in a mixture of THF/water 3/1 (20 ml), and the reaction mixture is boiled under reflux over night. The solvent is removed in vacuum on a rotary evaporator, and 2 N HCl is added to the residue. This phase is extracted with dichloromethane. The combined organic phases are dried over magnesium sulfate, filtered and concentrated in vacuum on a rotary evaporator. The residual solid is the desired product (quantitative yield, 554 mg).

$C_{21}H_8O_4$; MW 334; $R_f$ value (hexane/ethyl acetate 1/1): 0.5; $^1$H-NMR (d-acetone and 3 drops of $CD_3OD$): δ 8.30 (d, J=16.1 Hz, 1H), 8.26 (d, J=8.8 Hz, 1H), 8.15 (d, J=1.9 Hz, 1H), 8.06 (d, J=9.1 Hz, 1H), 7.89 (dd, J=2.2 Hz, J=8.8 Hz, 1H), 7.52 (d, J=9.1 Hz, 1H), 7.39 (t, J=7.9 Hz, 1H), 7.35-7.34 (m, 1H), 7.32 (t, J=2.2 Hz, 1H), 6.95-6.92 (m, 1H), 6.74 (d, J=16.1 Hz, 1H), 4.06 (s, 3H), 3.87 (s, 3H); IR: 3382, 2946, 2837, 1678 1/cm

21.) 5-Methoxy-2-(3-methoxyphenyl)-1H-indole

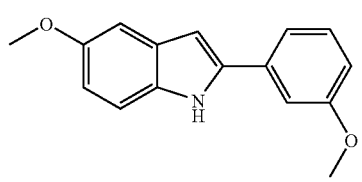 [SMILES: COc1cccc(-c2cc3cc(OC)ccc3[nH]2)c1]

To a boiling mixture of p-anisidine (2.46 g, 20 mmol, 6.66 eq) and N,N-dimethylaniline (3.5 ml) is slowly added dropwise 2-bromo-4-methoxyacetophenone (0.7 g, 3 mmol, 1 eq) dissolved in ethyl acetate (12 ml). After the addition is complete, the reaction mixture is stirred at 180° C. for 2 h. To the cooled mixture are added ethyl acetate and 2 M HCl. The aqueous phase is extracted with ethyl acetate several times, and the combined organic phases are washed with a saturated NaCl solution, dried over $MgSO_4$, filtered and evaporated to dryness on a rotary evaporator. Purification by column chromatography (eluent dichloromethane/hexane 7/3) yields the desired product in a yield of 15% (760 mg).

C$_{16}$H$_{15}$NO$_2$; MW 253; $^1$H-NMR (CDCl$_3$): δ 8.22 (bs, 1H), 7.33 (t, J=7.9 Hz, 1H), 7.25 (d, J=8.8 Hz, 1H), 7.21 (d, J=7.6 Hz, 1H), 7.16 (t, J=2.5 Hz, 1H), 7.07 (d, J=2.2 Hz, 1H), 6.84 (dt, J=2.5 Hz, J=8.8 Hz, 2H), 6.74 (d, J=2.2 Hz, 1H), 3.86 (s, 3H), 3.85 (s, 3H); $^{13}$C-NMR (CDCl$_3$): δ 160.1, 154.5, 138.5, 133.9, 132.0, 130.1, 129.6, 117.6, 113.0, 112.7, 110.9, 102.3, 100.1, 55.9, 55.4; IR: 3364 (NH), 2998, 2835, 1610, 1581, 1483 1/cm; MS (ESI): 254 (M+H)$^+$

22.) 6-Methoxy-2-(3-methoxyphenyl)quinoline

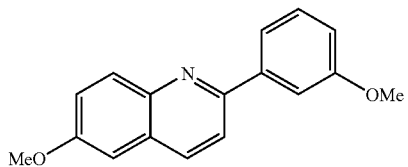 [SMILES: COc1cccc(-c2ccc3cc(OC)ccc3n2)c1]

Two Step Reaction:

Grignard: To 231 mg (9.63 mmol, 6 eq) of purified magnesium in 10 ml of dry ether are added two crystals of iodine and 1.5 g (8.02 mmol, 5 eq) of bromoanisole dissolved in 10 ml of dry ether. The reaction mixture is boiled under reflux and under nitrogen atmosphere at 30° C. for 2 h.

Coupling: 281 mg (1.60 mmol, 1 eq) of 6-methoxyquinoline-N-oxide dissolved in 80 ml of toluene is added to the Grignard mixture, and the mixture is heated at 90° C. for 2 h. After cooling the round-bottom flask, the reaction mixture is added on ice, and after the ice is molten, 2 N hydrochloric acid and water are added until the precipitate formed has dissolved. The water phase is washed with ether and made alkaline with KOH. After extraction with chloroform, the combined organic phases are dried over magnesium sulfate, filtered, and the solvent is removed in vacuum on a rotary evaporator. Purification was performed by means of column chromatography with hexane/ethyl acetate 95/5 as the eluent to obtain the desired product in a yield of 47% (199 mg).

C$_{17}$H$_{15}$NO$_2$; MW 265; $^1$H-NMR (CDCl$_3$): δ 7.91 (d, J=1.5 Hz, 1H), 7.89 (s, 1H), 7.62 (d, J=8.8 Hz, 1H); 7.57 (t, J=2.4 Hz, 1H), 7.50 (d, J=7.9 Hz, 1H), 7.24 (t, J=7.9 Hz, 1H), 7.20 (dd, J=2.7 Hz, J=9.1 Hz, 1H), 6.89 (d, J=2.7 Hz, 1H), 6.82 (dd, J=2.7 Hz, J=8.2 Hz, 1H), 3.75 (s, 3H), 3.74 (s, 3H); $^{13}$C-NMR (CDCl$_3$): δ 160.1, 157.7, 154.8, 144.3, 141.3, 135.5, 131.1, 129.8, 128.3, 122.4, 119.8, 119.4, 115.0, 112.5, 105.0, 55.5, 55.4; IR: 2964, 2839, 1621, 1600, 1583, 1559, 1478, 1455, 1430 1/cm; MS (ESI): 266 (M+H)$^+$

23.) 7-Methoxy-3-(4-methoxyphenyl)quinoline

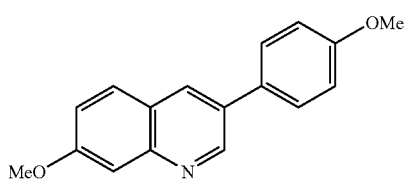 [SMILES: COc1ccc(-c2cnc3cc(OC)ccc3c2)cc1]

To a solution of 2-(4-methoxyphenyl)malondialdehyde (797 mg, 4.48 mmol, 1 eq) in 20 ml of ethanol are added m-anisidine (551 mg, 4.48 mmol, 1 eq) and 10 ml of conc. HCl. The reaction mixture is stirred at 80° C. for 3 days, and after cooling to RT, the reaction is stopped by adding a 10% sodium carbonate solution. The mixture is extracted with dichloromethane, and the organic phase is dried over MgSO$_4$, filtered, and the solvent is removed in vacuum on a rotary evaporator. After purification by column chromatography with hexane/ethyl acetate as the eluent, the product was obtained in a yield of 19% (221 mg).

C$_{17}$H$_{15}$NO$_2$; MW 265; $^1$H-NMR (CDCl$_3$): δ 8.98 (d, J=2.2 Hz, 1H), 8.07 (d, J=2.2 Hz, 1H), 7.63 (d, J=9.1 Hz, 1H), 7.53 (d, J=8.8 Hz, 2H), 7.35 (d, J=2.5 Hz, 1H), 7.13 (dd, J=2.5 Hz, J=9.1 Hz, 1H), 6.95 (d, J=8.8 Hz, 2H), 3.88 (s, 3H), 3.78 (s, 3H); $^{13}$C-NMR (CDCl$_3$): δ 160.5, 159.6, 145.9, 148.7, 132.3, 131.6, 130.5, 128.9, 128.3, 123.3, 120.1, 114.6, 107.2, 55.5, 55.4; IR: 2928, 1613, 1514, 1491, 1461.1237, 1025 1/cm; MS (ESI): 266 (M+H)$^+$

Coupling Reactions:

Suzuki Reaction

Method A:

To an oxygen-free mixture of halogen derivative (1 eq) in toluene/ethanol 2/1 or DME and 2% sodium carbonate solution (2 eq) are added tetrakis(triphenylphosphine)palladium (0) (0.1 eq) and boric acid (1 eq) under a nitrogen atmosphere. The reaction mixture is boiled under reflux at 80° C. over up to 24 h. For processing the reaction, the hydrophilic and lipophilic phases are separated, and the hydrophilic phase is extracted with dichloromethane or ethyl acetate. The combined organic phases are subsequently washed with a 2% hydrochloric acid solution to remove any boric acid present, and made alkaline with 2% sodium carbonate solution. After further washing with water and subsequent drying over magnesium sulfate, the solvent is removed in vacuum. The purification of the desired product was mostly performed by means of column chromatography.

Method B:

In a dry reaction vessel, the halogen derivative (0.2 mmol), boric acid (0.4 mmol), K$_2$CO$_3$ (0.6 mmol) and Pd(OAc)$_2$ are suspended in 5 ml of DME/water/ethanol 7/3/2 and subjected to microwave irradiation at 150° C. for 300 s. The reaction mixture is subsequently filtered and concentrated in vacuum on a rotary evaporator. The purification was performed by means of preparative HPLC (Waters Fraktion Lynx Autopurification System, Varian Inertsil C18 column 50×21 mm, particle size 3 μm, gradient with isocratic end period, solvent: acetonitrile, water, formic acid (0.01%) 0-100%).

Method C:

The bromo derivative (1 eq), boric acid (1.3 eq) and Pd(PPh$_3$)$_4$ (0.05 eq) are suspended in 1.5 ml of DMF in a 10 ml reaction vessel using a magnetic stirrer. NaHCO$_3$ (3 eq) in 1.5 ml of water is added, and the mixture is subjected to 100 W microwave irradiation at 140° C. for 15 min. Thereafter, the reaction mixture is taken up in 20 ml of ethyl acetate and 20 ml of water, and the aqueous phase obtained is extracted with ethyl acetate. The combined organic extracts are dried over magnesium sulfate, filtered and concentrated in vacuum on a rotary evaporator. Purification was performed by means of column chromatography with silica gel as the stationary phase.

24.) 3-(4-Methoxyphenyl)quinoline

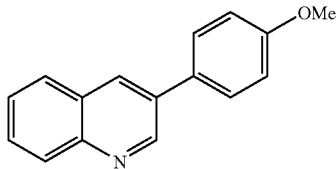 [SMILES: COc1ccc(-c2cnc3ccccc3c2)cc1]

The compound is prepared by the reaction of 3-bromoquinoline (500 mg, 2.40 mmol, 1 eq) with 4-methoxyphenylboric acid (365 mg, 2.40 mmol, 1 eq) according to method A in 18 h. Purification by column chromatography with a mixture of hexane/ethyl acetate 9/1 yielded the desired product as a white solid in a yield of 89% (504 mg).

$C_{16}H_{13}NO$; MW 235; $^1$H-NMR (CDCl$_3$): δ 9.09 (d, J=2.2 Hz, 1H), 8.18 (d, J=2.2 Hz, 1H), 8.05 (d, J=8.5 Hz, 1H), 7.80 (d, J=8.5 Hz, 1H), 7.60 (d, J=1.3 Hz, 3H), 7.50 (t, J=8.2 Hz, 1H), 6.98 (d, J=8.8 Hz, 2H), 3.82 (s, 3H); $^{13}$C-NMR (CDCl$_3$): δ 159.8, 149.9, 147.1, 132.4, 130.3, 129.2, 129.1, 128.5, 127.9, 127.0, 114.7, 55.4; IR: 3062; 2930; 2833; 1602; 1517; 1460; 1254 1/cm; MS (ESI): 236 (M+H)$^+$

25.) 3-(3-Methoxyphenyl)quinoline

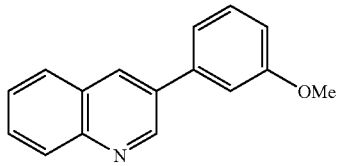 [SMILES: COc1cccc(-c2cnc3ccccc3c2)c1]

The compound is prepared by the reaction of 3-bromoquinoline (200 mg, 0.96 mmol, 1.06 eq) and 3-methoxyphenylboric acid (138 mg, 0.91 mmol, 1 eq) according to method A in 19 h. Purification by column chromatography with a mixture of hexane/ethyl acetate 3/1 yields the desired product in a yield of 70% (147 mg).

$C_{16}H_{13}NO$; MW 235; $^1$H-NMR (CDCl$_3$): δ 9.09 (d, J=2.2 Hz, 1H), 8.05 (d, J=8.51 Hz, 1H), 8.19 (d, J=2.2 Hz, 1H), 7.78 (d, J=8.5 Hz, 1H), 7.62 (dt, J=1.6, J=8.5 Hz, 1H), 7.49 (dt, J=1.3 Hz, J=8.2 Hz, 1H), 7.34 (t, J=7.9 Hz, 1H), 7.20 (d, J=7.5 Hz, 1H), 7.14 (t, J=2.5 Hz, 1H), 6.89 (dd, J=2.5 Hz, J=8.2 Hz, 1H), 3.80 (s, 3H); $^{13}$C-NMR (CDCl$_3$): δ 160.2, 149.9, 147.5, 139.4, 133.7, 133.3, 130.2, 129.4, 129.3, 128.0, 127.0, 119.9, 113.4, 113.3, 55.4; IR: 1600, 1581, 1492, 1465, 1276, 1260 1/cm; MS (ESI): 236 (M+H)$^+$

26.) 7-Methoxy-3-(3-methoxyphenyl)quinoline

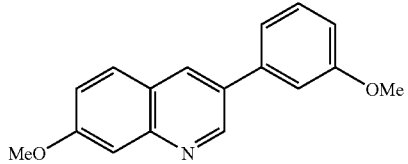 [SMILES: COc1cccc(-c2cnc3cc(OC)ccc3c2)c1]

The compound is prepared by the reaction of 3-bromo-7-methoxyquinoline (255 mg, 1.07 mmol, 1.06 eq) and 3-methoxyphenylboric acid (154 mg, 1.01 mmol, 1 eq) according to method A in 4.5 h. Purification by column chromatography with a mixture of hexane/ethyl acetate 9/1 yields the desired product in a yield of 76% (215 mg).

$C_{17}H_{15}NO_2$; MW 265; $^1$H-NMR (CDCl$_3$): δ 9.02 (d, J=2.2 Hz, 1H), 8.15 (d, J=2.2 Hz, 1H), 7.68 (d, J=8.3 Hz, 1H), 7.39 (d, J=2.5 Hz, 1H), 7.36 (t, J=7.9 Hz, 1H), 7.20 (d, J=7.6 Hz, 1H), 7.18 (d, J=2.5 Hz, 1H), 7.16 (m, 1H), 6.89 (dd, J=2.5 Hz, J=8.2 Hz, 1H), 3.91 (s, 3H), 3.83 (s, 3H); $^{13}$C-NMR (CDCl$_3$): δ 160.8, 160.2, 150.0, 149.15, 139.6, 133.1, 131.8, 130.2, 129.0, 123.2, 120.3, 119.7, 113.1, 107.2, 55.6, 55.4; IR: 1621, 1600, 1581, 1497, 1456, 1435, 1260 1/cm; MS (ESI): 266 (M+H)$^+$

27.) 3-Methoxy-5-(6-methoxynaphthalene-2-yl)pyridine

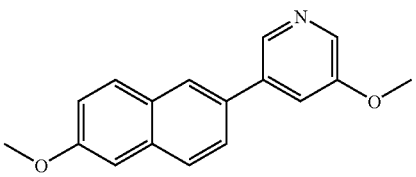

The compound is prepared by the reaction of 6-methoxynaphthaleneboric acid (258 mg, 1.28 mmol, 1.2 eq) with 3-bromo-5-methoxypyridine (200 mg, 1.06 mmol, 1 eq) according to method A in 24 h. Purification by column chromatography with a mixture of hexane/ethyl acetate 2/1 yields the desired product in a yield of 84% (237 mg).

$C_{17}H_{15}NO_2$; MW 265; $^1$H-NMR (d-acetone): δ 8.58 (d, J=1.9 Hz, 1H), 8.28 (d, J=2.8 Hz, 1H), 8.18 (d, J=1.3 Hz, 1H), 7.94-7.90 (m, 2H), 7.81 (dd, J=1.9 Hz, J=8.5 Hz, 1H), 7.67 (dd, J=1.9 Hz, J=2.5 Hz, 1H), 7.36 (d, J=2.2 Hz, 1H), 7.21 (dd, J=2.5 Hz, J=8.8 Hz, 1H), 3.98 (s, 3H), 3.95 (s, 3H); $^{13}$C-NMR (d-acetone): 159.2, 157.0, 141.1, 137.9, 137.2, 135.4, 133.6, 130.6, 130.1, 128.5, 126.8, 126.4, 120.2, 118.9, 106.5, 56.0, 55.7; IR: 3359, 1586, 1444, 1268 1/cm

28.) 2-Methoxy-6-(4-methoxyphenyl)naphthalene

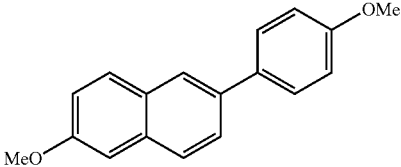 [SMILES: COc1ccc(-c2ccc3cc(OC)ccc3c2)cc1]

The compound is prepared by the reaction of 2-bromo-6-methoxynaphthalene (500 mg, 2.11 mmol, 1 eq) with 4-methoxyphenylboric acid (313 mg, 2.12 mmol, 1 eq) according to method A in 5 h. The desired product was precipitated from hexane in a yield of 56% (311 mg).

$C_{18}H_{16}O_2$; MW 264; $^1$H-NMR: (CDCl$_3$): δ 7.85 (d, J=1.2 Hz, 1H), 7.7 (dd, J=5.6, J=8.5 Hz, 2H), 7.62 (dd, J=1.9 Hz, J=8.5 Hz, 1H), 7.56 (dd, J=1.9 Hz, J=8.8 Hz, 2H), 7.10 (m, 2H), 6.94 (d, J=8.5 Hz, 2H), 3.87 (s, 3H), 3.80 (s, 3H); $^{13}$C-NMR (CDCl$_3$): δ 159.1, 157.6, 136.1, 133.8, 133.4, 129.6, 129.3, 128.2, 127.2, 125.9, 124.9, 119.0, 114.3, 105.6, 55.4, 55.3; IR: 2924, 2854, 1628, 1598, 1500, 1244 1/cm; MS (APCI): 265 (M+H)$^+$

29.) 2-Methoxy-6-(3-methoxyphenyl)naphthalene

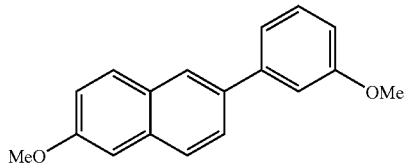 [SMILES: COc1cccc(-c2ccc3cc(OC)ccc3c2)c1]

The compound is prepared by the reaction of 2-bromo-6-methoxynaphthalene (500 mg, 2.11 mmol, 1 eq) with 3-methoxyphenylboric acid (321 mg, 2.11 mmol, 1 eq) according to method A within 22 h. Purification by column chromatography with a mixture of hexane/ethyl acetate 9/1 yields the desired product in a yield of 81% (451 mg).

$C_{18}H_{16}O_2$; MW 264; $^1$H-NMR (CDCl$_3$): δ 7.95 (s, 1H), 7.78 (dd, J=4.4 Hz, J=8.3 Hz, 2H), 7.69 (dd, J=1.7 Hz, J=8.3 Hz, 1H), 7.37 (t, J=7.8 Hz, 1H), 7.26 (d, J=7.8 Hz, 1H), 7.21 (t, J=2.2 Hz, 1H), 7.16 (d, J=2.5 Hz, 1H), 7.15 (s, 1H), 6.89 (dd, J=2.4 Hz, J=8.1 Hz, 1H), 3.93 (s, 3H), 3.88 (s, 3H); $^{13}$C-NMR (CDCl$_3$): δ 128.65, 127.50, 127.15, 121.20, 120.65, 114.40, 113.95, 56.80; IR: 2963; 2838; 1594; 1493; 1455; 1389; 1254 1/cm; MS (ESI): 265 (M+H)$^+$

30.) 2-Methoxy-6-(2-methoxyphenyl)naphthalene

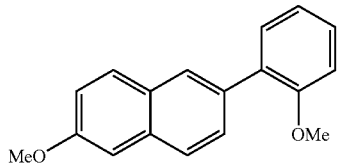 [SMILES: COc1ccc2cc(-c3ccccc3OC)ccc2c1]

The compound is prepared by the reaction of 2-bromo-6-methoxynaphthalene (300 mg, 1.26 mmol, 1 eq) with 2-methoxyphenylboric acid (192 mg, 1.26 mmol, 1 eq) according to method A within 18 h. Purification by column chromatography was not performed, but the raw product was used for further syntheses.

31.) 2-Methoxy-6-(3-nitrophenyl)naphthalene

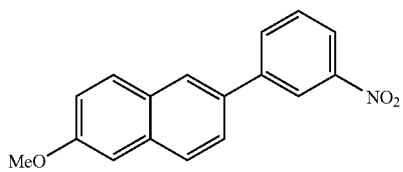 [SMILES: COc1ccc2cc(-c3cccc([N+](=O)[O-])c3)ccc2c1]

The compound is prepared by the reaction of 3-bromonitrobenzene (1 g, 4.95 mmol, 1 eq) with 6-methoxynaphthaleneboric acid (1 g, 4.95 mmol, 1 eq) according to method A within 20 h. Purification by column chromatography with hexane as the eluent yields the desired product in a yield of 40%, 557 mg.

$C_{18}H_{17}NO_3$; MW 295; $^1$H-NMR (CDCl$_3$): δ 8.54 (t, J=1.9 Hz, 1H), 8.18 (ddd, J=0.9 Hz, J=2.2 Hz, J=8.2 Hz, 1H), 8.01-7.99 (m, 2H), 7.84 (d, J=8.5 Hz, 1H), 7.80 (d, J=8.8 Hz, 1H), 7.70 (dd, J=1.9 Hz, J=8.5 Hz, 1H), 7.63-7.59 (m, 1H), 7.20 (dd, J=2.8 Hz, J=9.1 Hz, 1H), 7.16 (d, J=2.5 Hz, 1H), 3.94 (s, 3H); $^{13}$C-NMR (CDCl$_3$): δ 158.3, 148.8, 142.9, 134.4, 133.7, 133.0, 129.8, 129.7, 129.0, 127.8, 126.1, 125.3, 121.9, 121.7, 119.7, 105.6, 55.4; IR: 1602, 1528, 1351 1/cm

32.) 3-(6-Methoxynaphthalene-2-yl)-phenylamine

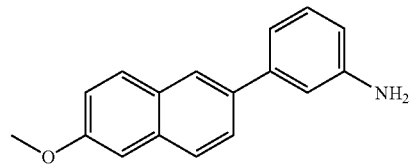 [SMILES: COc1ccc2cc(-c3cccc(N)c3)ccc2c1]

To a solution of 2-methoxy-6-(3-nitrophenyl)naphthalene (200 mg, 0.71 mmol, 1 eq) in 100 ml of dry THF, Pd/C is added, and the mixture is stirred over night at RT under a hydrogen atmosphere. After filtration over Celite and purification by means of preparative thin-layer chromatograph, the product is obtained in a yield of 20% (36 mg).

$C_{17}H_{15}NO$; MW 249; $^1$H-NMR (CD$_3$OD+3 drops of CDCl$_3$): δ 8.06 (d, J=1.3 Hz, 1H), 7.89 (d, J=8.8 Hz, 1H), 7.85 (d, J=9.1 Hz, 1H), 7.75 (dd, J=1.9 Hz, J=8.5 Hz, 1H), 7.59 (d, J=7.9 Hz, 1H), 7.55-7.52 (m, 2H), 7.28 (d, J=2.5 Hz, 1H), 7.20 (dd, J=2.5 Hz, J=8.8 Hz, 1H), 7.18-7.16 (m, 1H), 3.97 (s, 3H); $^{13}$C-NMR (CD$_3$OD+3 drops of CDCl$_3$): δ 159.9, 145.2, 136.0, 132.1, 131.9, 130.9, 130.8, 130.5, 128.9, 127.0, 126.9, 126.2, 122.4, 122.0, 120.6, 106.6, 55.8; IR: 2923, 2854, 1461, 1377 1/cm

33.) 6-Phenylnaphthalene-2-ol (2)

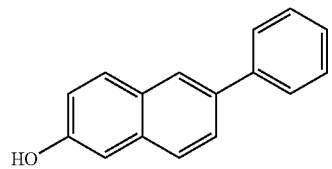 [SMILES: Oc1ccc2cc(-c3ccccc3)ccc2c1]

The compound is prepared by the reaction of 6-bromo-2-naphthol (500 mg, 2.24 mmol, 1 eq) with phenylboric acid (1 eq) according to method A within 20 h. Purification by column chromatography with hexane/ethyl acetate 7/3 as the eluent yields the desired product in a yield of 87%, 429 mg.

$C_{16}H_{12}O$; MW 220; $^1$H-NMR (CD$_3$OD): δ 8.00 (bs. 1H), 7.82 (d, J=8.7 Hz, 1H), 7.76-7.73 (m, 3H), 7.71 (dd, J=1.7 Hz, J=8.4 Hz, 1H), 7.50-7.47 (m, 2H), 7.37-7.34 (m, 1H), 7.17 (d, J=2.3 Hz, 1H), 7.13 (dd, J=2.3 Hz, J=8.7 Hz, 1H); $^{13}$C-NMR (CD$_3$OD): δ 155.3, 141.2, 135.5, 134.3, 129.4, 128.4, 126.5, 126.4, 125.2, 125.0, 118.3, 108.3; IR: 3335 1/cm

34.) 3-Naphthalene-2-ylphenol (3)

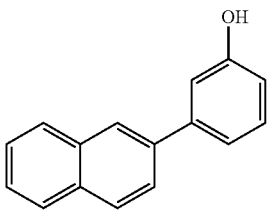 [SMILES: Oc1cccc(-c2ccc3ccccc3c2)c1]

The compound is prepared by the reaction of 2-bromonaphthalene (303 mg, 1.46 mmol, 1 eq) with 3-hydroxyphenylboric acid (242 mg, 1.76 mmol, 1.2 eq) according to method A within 18 h. Purification by column chromatography with dichloromethane as the eluent yields the desired product in a yield of 47%, 152 mg.

$C_{16}H_{12}O$; MW 220; $^1$H-NMR (CD$_3$OD): δ 8.06 (m, 1H); 7.92 (d, J=8.2 Hz, 2H); 7.88 (dd, J=7.5 Hz, J=1.5 Hz, 1H); 7.76 (dd, J=8.5 Hz, J=1.8 Hz, 1H); 7.52-7.49 (m, 2H); 7.34 (t, J=7.5 Hz, 1H); 7.25-7.23 (m, 1H); 7.20 (t, J=1.8 Hz, 1H); 6.85 (m, 1H); $^{13}$C-NMR (CD$_3$OD): δ 159.0, 143.8, 139.9, 135.2, 134.2, 131.0, 129.4, 129.2, 128.6, 127.3, 126.9, 126.5, 126.4, 119.6, 115.4, 115.1; IR: 3380, 3055, 1599, 1184 1/cm; MS (ESI): 221 (M+H)$^+$

35.) 6-(3-Hydroxyphenyl)-3,4-dihydronaphthalene-1(2H)-one

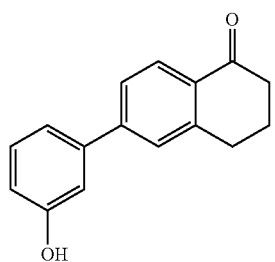 [SMILES: O=C1CCCc2cc(-c3cccc(O)c3)ccc21]

The compound is prepared by the reaction of 5-oxo-5,6,7,8-tetrahydronaphthalene-2-yl trifluoromethanesulfonate (1.78 g, 6.04 mmol, 1 eq) with 3-hydroxyphenylboric acid (1 g, 7.25 mmol, 1.2 eq) according to method A within 4 h. Purification by column chromatography with dichloromethane as the eluent yields the desired product in a yield of 29%, 900 mg.

$C_{16}H_{14}O_2$; MW 238; $^1$H-NMR (CD$_3$OD): δ 8.04-8.02 (d, J=8.8 Hz, 1H), 7.56 (m, J=6.0 Hz, 2H), 7.31-7.27 (t, J=7.9 Hz, 1H), 7.16 (d, J=6.6 Hz, 1H), 7.10-7.09 (t, J=2.2 Hz, 1H), 6.85-6.84 (d, J=7.9 Hz, 1H), 3.09-3.07 (t, J=6.0 Hz, 2H), 2.71-2.68 (t, J=6.3 Hz, 2H); 2.20-2.18 (m, J=6.3 Hz, 2H); $^{13}$C-NMR (CD$_3$OD): δ 200.7, 159.20, 147.9, 147.1, 142.7, 132.6, 131.2, 128.6, 128.4, 126.5, 119.6, 116.5, 115.1, 40.2, 30.9, 24.7; IR: 3410, 3059, 2940, 2557, 1714, 1600, 1259, 1209 1/cm; MS (ESI): 239 (M+H)$^+$

36.) 6-(4-Methoxyphenyl)-3,4-dihydronaphthalene-1(2H)-one

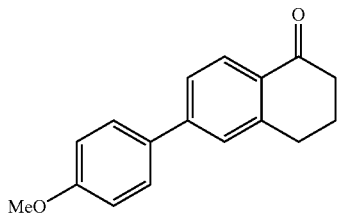 [SMILES: COc1ccc(-c2ccc3c(c2)CCCC3=O)cc1]

The compound is prepared by the reaction of 5-oxo-5,6,7,8-tetrahydronaphthalene-2-yl trifluoromethanesulfonate (1.61 g, 5.48 mmol, 1 eq) with 4-hydroxyphenylboric acid (1 g, 6.58 mmol, 1.2 eq) according to method A within 4 h. Purification by column chromatography with dichloromethane/hexane 7/3 as the eluent yields the desired product in a yield of 72%, 1.2 g.

$C_{17}H_{16}O_2$; MW 252; $^1$H-NMR (CD$_3$OD): δ 8.04 (d, J=8.8 Hz, 1H), 7.65 (d, J=8.9 Hz, 2H), 7.57 (d, J=7.6 Hz, 2H), 7.04 (d, J=8.8 Hz, 2H), 3.87 (s, 3H), 3.07 (t, J=6.0 Hz, 2H), 2.68 (t, J=6.0 Hz, 2H), 2.19 (m, 2H); $^{13}$C-NMR (CD$_3$OD): 198.1, 159.9, 145.6, 144.9, 132.7, 131.0, 128.4, 127.8, 126.6, 125.0, 114.4, 55.4, 39.2, 30.0, 23.3; IR: 2938, 1717, 1599, 1210 1/cm

37.) 7-(3-Hydroxyphenyl)-1-naphthol

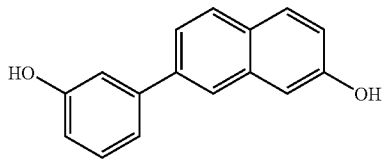 [SMILES: Oc1cccc(-c2ccc3ccc(O)cc3c2)c1]

The compound is prepared by the reaction of 2-hydroxy-7-triflatenaphthalene (292 mg, 1 mmol, 1 eq) with 3-hydroxyphenylboric acid (166 mg, 1.2 mmol, 1.2 eq) according to method A within 5 h. Purification by column chromatography with hexane/ethyl acetate 8/2 as the eluent yields the desired product in a yield of 26%, 61 mg.

$C_{16}H_{12}O_2$; MW 236; $^1$H-NMR (CD$_3$OD): δ 7.84 (s, 1H), 7.80 (d, J=8.5 Hz, 1H), 7.74 (d, J=8.8 Hz, 1H), 7.50 (dd, J=8.5 Hz, J=1.8 Hz, 1H), 7.29 (t, J=7.9 Hz, 1H), 7.20 (m, 2H), 7.15 (t, J=2.1 Hz, 1H), 7.07 (dd, J=2.4 Hz, J=8.8 Hz, 1H), 6.80 (m, 1H); IR: 3354, 2933, 1643, 1604, 1514, 1493, 1454, 1441, 1212 1/cm; MS (ESI): 234 (M−2H)

Compounds 4-11 were prepared according to method B.

| Compound | Structure | MW | Area ELSD (%) | MS retention time |
|---|---|---|---|---|
| 4 | 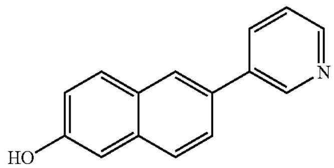 [SMILES: Oc1ccc2cc(-c3cccnc3)ccc2c1] | 221 | 100 | 4.95 |
| 5 | 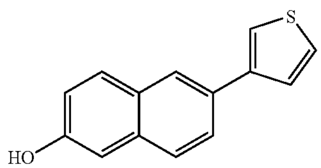 [SMILES: Oc1ccc2cc(-c3ccsc3)ccc2c1] | 226 | 100 | 6.03 |
| 6 | 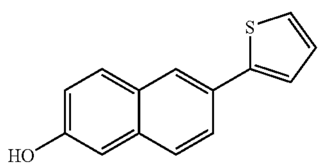 [SMILES: Oc1ccc2cc(-c3cccs3)ccc2c1] | 226 | 100 | 6.11 |
| 7 | 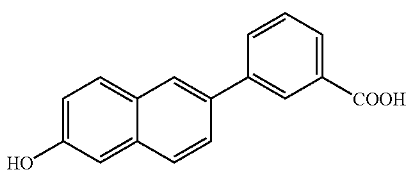 [SMILES: O=C(O)c1cccc(-c2ccc3cc(O)ccc3c2)c1] | 264 | 100 | 4.54 |
| 8 | 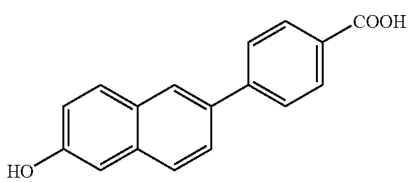 [SMILES: O=C(O)c1ccc(-c2ccc3cc(O)ccc3c2)cc1] | 264 | 100 | 4.46 |
| 9 | 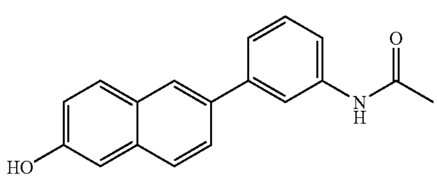 [SMILES: CC(=O)Nc1cccc(-c2ccc3cc(O)ccc3c2)c1] | 277 | 100 | 5.05 |
| 10 | 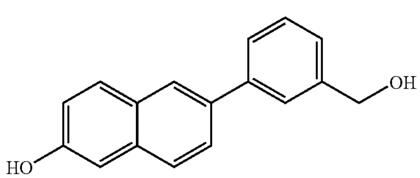 [SMILES: OCc1cccc(-c2ccc3cc(O)ccc3c2)c1] | 250 | 100 | 5.00 |
| 11 | 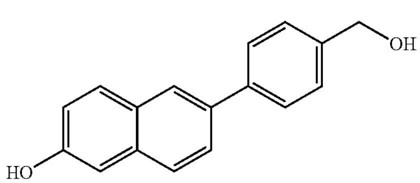 [SMILES: OCc1ccc(-c2ccc3cc(O)ccc3c2)cc1] | 250 | 100 | 5.12 |

38.) (E)-3-[3-Methoxy-5-(6-methoxynaphthalene-2-yl)phenyl]acrylic acid

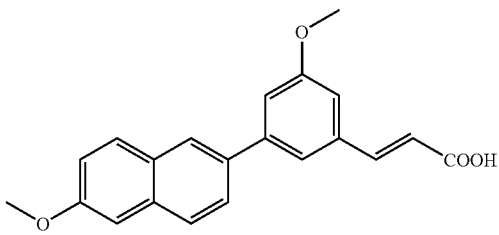 [SMILES: COc1cc(/C=C/C(=O)O)cc(-c2ccc3cc(OC)ccc3c2)c1]

The compound is prepared by the reaction of (E)-3-(3-bromo-5-methoxyphenyl)acrylic acid (751 mg, 2.92 mmol, 1 eq) with 6-methoxynaphthaleneboric acid (1 eq) according to method A in 26 h. Acidifying the aqueous phase with conc. HCl yielded the desired compound as a precipitate in a yield of 64%, 624 mg.

$C_{21}H_8O_4$; MW 334; $^1$H-NMR (DMSO): δ 8.24 (d, J=1.6 Hz, 1H), 7.91 (d, J=8.8 Hz, 1H), 7.90 (d, J=8.5 Hz, 1H), 7.87 (dd, J=1.6 Hz, J=8.5 Hz, 1H), 7.67-7.66 (m, 1H), 7.61 (d, J=16.1 Hz, 1H), 7.57 (bs, 1H), 7.36-7.35 (m, 2H), 7.20 (dd, J=2.5 Hz, J=8.8 Hz, 1H), 6.17 (d, J=16.1 Hz, 1H), 3.89 (s, 3H), 3.88 (s, 3H); $^{13}$C-NMR (DMSO): δ 172.1, 168.0, 160.2, 159.9, 157.6, 142.2, 136.5, 134.4, 129.8, 128.7, 127.3, 125.5, 125.4, 121.8, 119.2, 119.0, 114.7, 111.7, 105.7, 55.4, 55.2; IR: 3622, 2958, 2923, 2871, 1732, 1433, 1261, 1232 1/cm

39.) 2-Methoxy-4-(6-methoxy-2-naphthyl)aniline hydrochloride

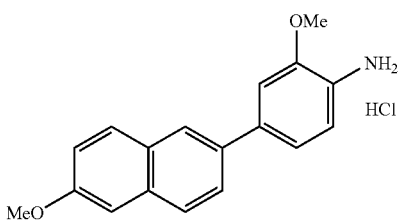 [SMILES: COc1ccc2cc(-c3ccc(N)c(OC)c3)ccc2c1 ; Cl]

The compound is prepared by the reaction of 4-bromo-2-methoxyaniline (400 mg, 1.98 mmol, 1 eq) with 6-methoxynaphthaleneboric acid (600 mg, 2.97 mmol, 1.5 eq) according to method A in 2.5 h. Acidifying the organic phase with a solution of 2 M HCl in diethyl ether yielded the desired compound as a precipitate in a yield of 50%, 312 mg.

$C_{18}H_{17}NO_2$, HCl; MW 315; $^1$H-NMR (CD$_3$OD): δ 8.10 (s, 1H), 7.89 (m, 2H), 7.78 (dd, J=1.9 Hz, J=8.5 Hz, 1H), 7.55 (s, 1H), 7.47 (m, 2H), 7.30 (d, J=2.2 Hz, 1H), 7.20 (dd, J=2.5 Hz, J=8.8 Hz, 1H), 4.10 (s, 3H), 3.96 (s, 3H); $^{13}$C-NMR (CD$_3$OD): δ 154.6, 136.0, 131.0, 128.9, 127.1, 126.7, 125.3, 120.9, 120.6, 119.6, 112.1, 106.7, 57.2, 56.0; IR: 2844, 1627, 1602, 1512, 1435 1/cm

40.) 2-Methoxy-6-(3-methoxy-5-methylphenyl)naphthalene

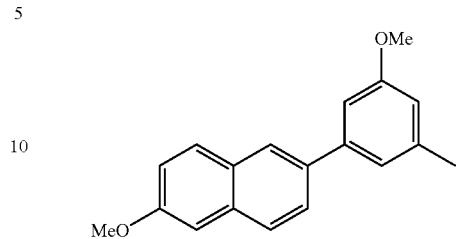

The compound is prepared by the reaction of 1-bromo-3-methoxy-5-methylbenzene (200 mg, 1.00 mmol, 1 eq) with 6-methoxynaphthaleneboric acid (201 mg, 1.00 mmol, 1 eq) according to method A in 22 h. Purification by column chromatography with hexane/ethyl acetate 9/1 as the eluent yielded the desired compound in a yield of 60%, 167 mg.

$C_{19}H_{18}O_2$; MW 278; $^1$H-NMR (CDCl$_3$): δ 7.94 (d, J=1.6 Hz, 1H), 7.78 (s, 1H), 7.76 (s, 1H), 7.68 (dd, J=1.9 Hz, J=8.5 Hz, 1H), 7.16-7.14 (m, 2H), 7.10 (s, 1H), 7.02 (s, 1H), 6.72 (s, 1H), 3.92 (s, 3H), 3.86 (s, 3H), 2.41 (s, 3H); $^{13}$C-NMR (CDCl$_3$): δ 160.1, 157.7, 142.5, 139.8, 136.4, 133.9, 129.7, 129.1, 127.1, 126.1, 125.6, 120.7, 119.1, 113.4, 110.0, 105.6, 55.3, 21.7; IR: 2994, 2939, 2834, 1590, 1453 1/cm; MS (ESI): 279 (M+H)$^+$

41.) 2-(4',5-Dimethoxy-1,1'-biphenyl-3-yl)-6-methoxynaphthalene

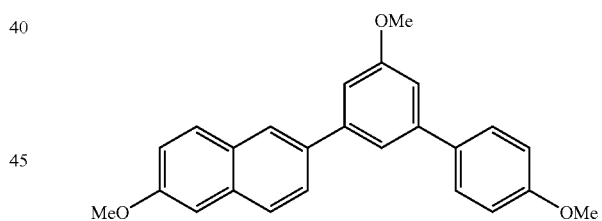

The compound is obtained in two steps. In the first step, 1,3-dibromo-5-methoxybenzene (290 mg, 1.09 mmol, 1 eq) reacts with 6-methoxynaphthaleneboric acid (331 mg, 1.64 mmol, 1.5 eq) according to method A for 18 h. Purification by column chromatography with hexane as the eluent yielded the intermediate compound (yield 32%), which is subjected to another Suzuki reaction. The intermediate compound (182 mg, 0.53 mmol, 1 eq) is subjected to reaction with 4-methoxybenzeneboric acid (121 mg, 0.79 mmol, 1.5 eq) for another 18 h according to method A. Purification by column chromatography with hexane as the eluent yields the desired compound in a yield of 42%, 78 mg.

$C_{25}H_{22}O_3$; MW 370; $^1$H-NMR (CDCl$_3$): δ 8.04 (d, J=1.5 Hz, 1H), 7.82-7.83 (m, 2H), 7.77 (dd, J=1.5 Hz, J=8.5 Hz, 1H), 7.62-7.64 (m, 2H), 7.50 (t, J=1.5 Hz, 1H), 7.18-7.21 (m, 2H), 7.18 (d, J=2.5 Hz, 1H), 7.12 (m, 1H), 7.01-7.03 (m, 2H), 3.95 (s, 3H), 3.94 (s, 3H), 3.87 (s, 3H); $^{13}$C-NMR (CDCl$_3$): δ 160.4, 157.9, 143.1, 142.8, 136.4, 134.0, 129.8, 128.4, 127.3, 126.1, 125.8, 119.2, 118.7, 114.3, 111.3, 105.6, 55.5, 55.4; IR: 2959, 1588, 1490, 1243 1/cm

42.) 2-Methoxy-6-[3-methoxy-5-(6-methoxy-2-naphthyl)phenyl]naphthalene

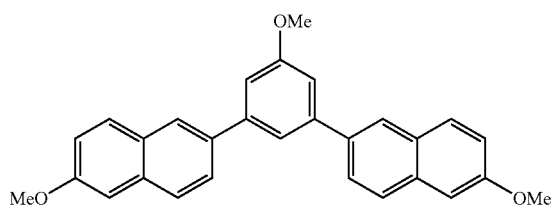 [SMILES: COc1cc(-c2ccc3cc(OC)ccc3c2)cc(-c2ccc3cc(OC)ccc3c2)c1]

The compound is prepared by the reaction of 1,3-dibromo-5-methoxybenzene (250 mg, 0.93 mmol, 1 eq) with 6-methoxy-2-naphthaleneboric acid (472 mg, 2.34 mmol, 2.5 eq) according to method A. Purification by column chromatography with hexane/dichloromethane 8/2 as the eluent yielded the desired compound in a yield of 49%, 192 mg.

$C_{29}H_{24}O_3$; MW 420; $^1$H-NMR (DMSO): δ 7.45 (s, 2H), 7.10 (m, 6H), 6.89 (s, 1H), 6.52 (d, J=2.5 Hz, 2H); 6.47 (d, J=1.6 Hz, 2H), 6.36 (d, J=2.5 Hz, 1H), 6.35 (d, J=2.5 Hz, 1H), 3.10 (s, 3H), 3.00 (s, 6H); $^{13}$C-NMR (DMSO): δ 161.8, 159.0, 143.9, 136.9, 135.2, 130.7, 130.2, 128.3, 126.8, 126.6, 120.0, 119.2, 112.3, 106.5, 55.9, 55.7; IR: 2930, 1588, 1268, 1199 1/cm; MS (ESI): 421 (M+H)$^+$

43.) 3-Methoxy-7-(3-methoxyphenyl)-2-naphthoic acid methyl ester

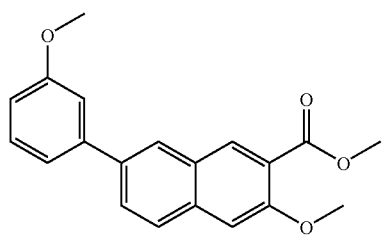 [SMILES: COC(=O)c1cc2cc(-c3cccc(OC)c3)ccc2cc1OC]

The compound is prepared by the reaction of 7-bromo-3-methoxy-2-naphthoic acid methyl ester (2.2 g, 7.45 mmol, 1 eq) with 3-methoxyphenylboric acid (1.37 g, 8.95 mmol, 1.5 eq) according to method A. Purification by column chromatography with a gradient of hexane/dichloromethane 1/1 to 3/7 and dichloromethane/methanol 95/5 as the eluent yielded the desired compound in a yield of 66%, 1.58 g.

$C_{20}H_{18}NO_4$; MW 322; $^1$H-NMR (CDCl$_3$): δ 8.34 (s, 1H), 7.99 (s, 1H), 7.79-7.74 (m, 2H), 7.38 (t, J=8.2 Hz, 1H), 7.25 (d, J=7.9 Hz, 1H), 7.20 (m, 2H), 6.91 (dd, J=2.5 Hz, J=8.2 Hz, 1H), 4.00 (s, 3H), 3.95 (s, 3H), 3.87 (s, 3H); $^{13}$C-NMR (CDCl$_3$): δ 166.7, 160.1, 155.9, 142.2, 137.1, 135.4, 133.1, 129.9, 128.1, 127.7, 127.0, 126.5, 122.2, 119.7, 113.0, 112.8, 106.6, 56.0, 55.4, 52.3; IR: 2950, 2836, 1729, 1599, 1490, 1463 1/cm

44.) 7-Methoxy-3-(3-methoxyphenyl)-1-naphthonitrile

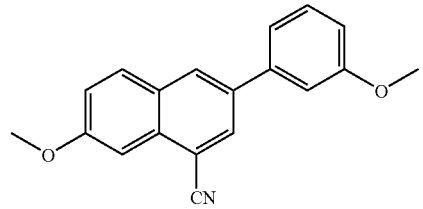

The compound is prepared by the reaction of 3-bromo-7-methoxy-1-naphthonitrile (1.4 g, 1.76 mmol, 1 eq) with 3-methoxyphenylboric acid (320 mg, 2.11 mmol, 1.2 eq) according to method A in 24 h. Purification by column chromatography with hexane/ethyl acetate 9/1 as the eluent yielded the desired compound in a yield of 53%, 300 mg.

$C_{20}H_{18}NO_4$; MW 322; $R_f$ value (hexane/ethyl acetate 7/3): 0.5; $^1$H-NMR (CDCl$_3$): δ 8.10 (d, J=1.6 Hz, 1H), 8.05 (d, J=1.9 Hz, 1H), 7.79 (d, J=9.1 Hz, 1H), 7.41 (m, 1H), 7.35 (t, J=7.9 Hz, 1H), 7.21 (dd, J=2.5 Hz, J=8.8 Hz, 1H), 7.18-7.16 (m, 1H), 7.11-7.10 (m, 1H), 6.88 (ddd, J=0.6 Hz, J=2.5 Hz, J=8.2 Hz, 1H), 3.94 (s, 3H), 3.83 (s, 3H); IR: 2950, 2836, 1729, 1599, 1490, 1463 1/cm 45.) 3-Methoxy-7-(3-methoxyphenyl)-1-naphthonitrile

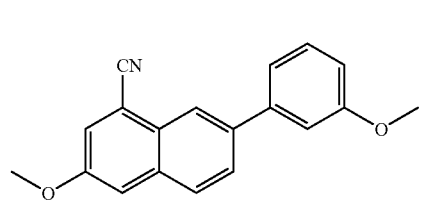

The compound is prepared by the reaction of 8-cyano-6-methoxynaphthalene-2-yl trifluoromethanesulfonate (466 mg, 1.4 mmol, 1 eq) with 3-methoxyphenylboric acid (260 mg, 1.7 mmol, 1.2 eq) according to method A over night. Purification by column chromatography with hexane/ethyl acetate 7/3 as the eluent yielded the desired compound in a yield of 25%, 113 mg.

$C_{20}H_{18}NO_4$; MW 322; $R_f$ value (hexane/ethyl acetate 7/3): 0.5; $^1$H-NMR (CD$_3$OD): δ 8.24 (m, 1H), 7.79 (d, J=8.5 Hz, 1H), 7.74 (dd, J=1.9 Hz, J=8.5 Hz, 1H), 7.52 (d, J=2.5 Hz, 1H), 7.34 (t, J=7.9 Hz, 1H), 7.32 (d, J=2.2 Hz, 1H), 7.24 (m, 1H), 7.18 (m, 1H), 6.88 (m, 1H), 3.89 (s, 3H), 3.83 (s, 3H); IR: 2362, 2225 1/cm

46.) 2-Methoxy-6-(3-methoxyphenyl)-1-naphthaldehyde

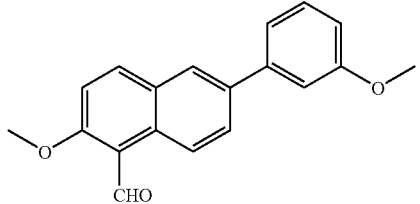

The compound is prepared by the reaction of 6-bromo-2-methoxy-1-naphthaldehyde (2 g, 7.55 mmol, 1 eq) with 3-methoxyphenylboric acid (1.3 g, 8.30 mmol, 1.1 eq) according to method A. Purification by column chromatography with hexane/ethyl acetate 1/1 as the eluent yielded the desired compound in a yield of 86%, 1.9 g.

$C_{19}H_{16}O_3$; MW 292; $^1$H-NMR (CDCl$_3$): δ 10.89 (s, 1H), 9.32 (d, J=9.1 Hz, 1H), 8.10 (d, J=9.1 Hz, 1H), 7.94 (d, J=1.8 Hz, 1H), 7.87 (dd, J=2.1 Hz, J=8.8 Hz, 1H), 7.38 (t, J=7.9 Hz, 1H), 7.31 (d, J=9.1 Hz, 1H), 7.28-7.27 (m, 1H), 7.22-7.21 (m, 1H), 6.91 (ddd, J=0.9 Hz, J=2.1 Hz, J=8.8 Hz, 1H), 4.05 (s, 3H), 3.88 (s, 3H); $^{13}$C-NMR (CDCl$_3$): δ 163.9, 160.1, 142.0, 137.8, 137.2, 130.8, 130.0, 129.9, 129.4, 125.9, 125.5, 119.7, 113.0, 112.8, 56.6, 55.4; IR: 2946, 2882, 2844, 2806, 1662 1/cm

47.) 1-Bromo-2-methoxy-6-(3-methoxyphenyl)naphthalene

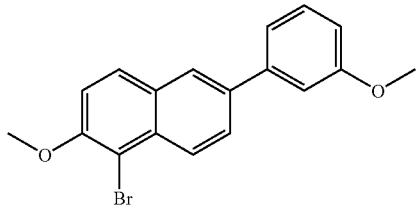

The compound is prepared by the reaction of 1,6-dibromo-2-methoxy-naphthalene (5.75 g, 18.20 mmol, 1 eq) with 3-methoxyphenylboric acid (2.77 g, 18.20 mmol, 1 eq) according to method A. Purification by column chromatography with hexane as the eluent yielded the desired compound in a yield of 81%, 5.1 g.

$C_{18}H_{15}BrO_2$; MW 343; $^1$H-NMR (CD$_3$OD): δ 8.22 (d, J=8.8 Hz, 1H), 7.92 (d, J=1.9 Hz, 1H), 7.80 (d, J=9.1 Hz, 1H), 7.77 (dd, J=1.9 Hz, J=8.8 Hz, 1H), 7.35 (t, J=7.9 Hz, 1H), 7.25-7.23 (m, 1H), 7.23 (d, J=9.1 Hz, 1H), 7.20-7.19 (m, 1H), 6.88 (ddd, J=0.9 Hz, J=2.5 Hz, J=8.2 Hz, 1H), 3.98 (s, 3H), 3.84 (s, 3H); $^{13}$C-NMR (CD$_3$OD): δ 160.1, 153.9, 142.0, 136.9, 132.5, 130.0, 129.9, 129.2, 127.4, 126.7, 125.8, 119.8, 114.0, 113.1, 112.8, 57.1, 55.4; IR: 2939, 1596, 1493, 1268, 1221, 1063, 1034 1/cm

48.) 6-(3-Hydroxyphenyl)-1-phenyl-2-naphthol (56)

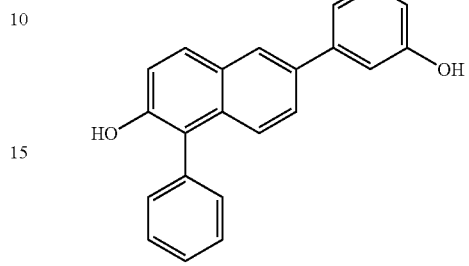

The compound is prepared by the reaction of 1-bromo-6-(3-hydroxyphenyl)-2-naphthol (50 mg, 0.16 mmol, 1 eq) with phenylboric acid (19.4 mg, 0.16 mmol, 1 eq) according to method A. Purification by column chromatography with hexane/ethyl acetate 7/3 as the eluent yielded the desired compound in a yield of 30%, 15 mg.

$C_{22}H_{16}O_2$; MW 312; $^1$H-NMR (CD$_3$OD): δ 8.01 (d, J=1.9 Hz, 1H), 7.84 (d, J=8.8 Hz, 1H), 7.58 (dd, J=1.9 Hz, J=8.8 Hz, 1H), 7.56-7.53 (m, 2H), 7.48-7.45 (m, 2H), 7.42-7.40 (m, 2H), 7.30-7.27 (m, 1H), 7.26 (d, J=8.8 Hz, 1H), 7.21-7.19 (m, 1H), 7.17 (t, J=1.9 Hz, 1H), 6.80 (ddd, J=0.9 Hz, J=2.2 Hz, J=7.9 Hz, 1H); $^{13}$C-NMR (CD$_3$OD): δ 161.4, 155.2, 146.3, 140.3, 139.2, 137.1, 134.8, 133.4, 132.8, 131.9, 130.7, 129.1, 129.0, 128.7, 125.7, 122.0, 121.9, 117.5, 117.3; IR: 3421, 1597, 1494, 1271, 1170 1/cm

49.) 1,6-Bis(3-hydroxyphenyl)naphthalene-2-ol (57)

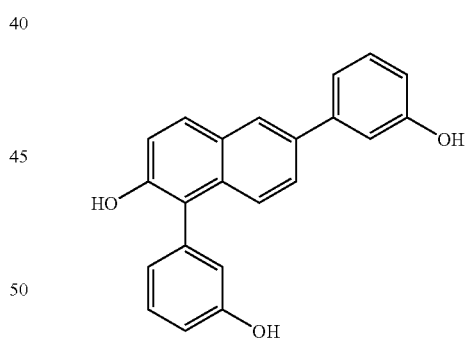

The compound is prepared by the reaction of 1,6-dibromonaphthalene-2-ol (200 mg, 0.66 mmol, 1 eq) with 3-hydroxybenzeneboric acid (182.8 mg, 1.32 mmol, 2 eq) according to method A in 21 h. Purification by column chromatography with dichloromethane/methanol 99/1 yields the desired compound in a yield of 5%, 11 mg.

$C_{22}H_{16}O_3$; MW 328; $R_f$ value (dichloromethane/methanol 98/2): 0.2; $^1$H-NMR (CDCl$_3$+3 drops of CD$_3$OD): δ 7.92 (d, J=1.6 Hz, 1H), 7.76 (d, J=8.8 Hz, 1H), 7.53 (dd, J=1.9 Hz, J=8.8 Hz, 1H), 7.48 (d, J=8.8 Hz, 1H), 7.39-7.36 (m, 1H), 7.26-7.23 (m, 1H), 7.20 (d, J=8.8 Hz, 1H), 7.16-7.14 (m, 1H), 7.11-7.10 (m, 1H), 6.92 (ddd, J=0.9 Hz, J=2.5 Hz, J=8.2 Hz, 1H), 6.89-6.87 (m, 1H), 6.85-6.84 (m, 1H), 6.78 (ddd, J=0.9 Hz, J=2.5 Hz, J=7.9 Hz, 1H); $^{13}$C-NMR (CDCl$_3$+3 drops of CD$_3$OD): 157.5, 156.9, 150.3, 142.6, 135.9, 135.8, 132.5, 130.5, 129.8, 129.5, 125.7, 125.2, 122.4, 121.0, 118.9, 117.9, 117.8, 115.3, 114.0; IR: 3355, 1702, 1581, 1494, 1447, 1203, 1154 1/cm; MS (ESI): 327 (M–H)$^-$

50.) 1-(Furan-3-yl)-6-(3-hydroxyphenyl)naphthalene-2-ol (58)

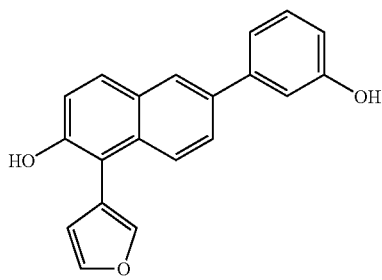 [SMILES: Oc1cccc(-c2ccc3c(-c4ccoc4)c(O)ccc3c2)c1]

The compound is prepared by the reaction of 1-bromo-6-(3-hydroxyphenyl)-naphthalene-2-ol (80 mg, 0.25 mmol, 1 eq) with 3-furaneboric acid (28.4 mg, 0.25 mmol, 1 eq) according to method A in 21 h. Purification by column chromatography with dichloromethane/methanol 98/2 yields the desired compound in a yield of 46%, 35 mg.

C$_{20}$H$_{14}$O$_3$; MW 302; R$_f$ value (dichloromethane/methanol 95/5): 0.8; $^1$H-NMR (CD$_3$OD+3 drops of CDCl$_3$): δ 7.98 (d, J=1.9 Hz, 1H), 7.86 (d, J=8.8 Hz, 1H), 7.79 (d, J=8.8 Hz, 1H), 7.70 (m, 1H), 7.68 (m, 1H), 7.64 (dd, J=2.2 Hz, J=8.8 Hz, 1H), 7.31-7.28 (m, 1H), 7.23 (d, J=8.8 Hz, 1H), 7.20 (m, 1H), 7.18-7.17 (m, 1H), 6.81 (ddd, J=0.9 Hz, J=2.5 Hz, J=7.9 Hz, 1H), 6.65 (dd, J=0.9 Hz, J=1.9 Hz, 1H); $^{13}$C-NMR (CD$_3$OD+3 drops of CDCl$_3$): δ 161.3, 156.1, 146.6, 146.3, 145.8, 139.4, 137.2, 133.5, 133.0, 132.8, 129.4, 128.7, 122.5, 122.1, 121.9, 117.7, 117.5, 116.9, 116.1; IR: 3340, 1601, 1493 1/cm; MS (ESI): 301 (M–H)$^-$

51.) 6-(3-Hydroxyphenyl)-1-(pyridin-3-yl)naphthalene-2-ol (59)

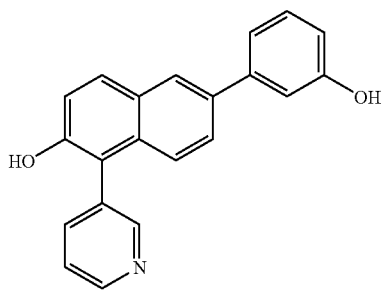 [SMILES: Oc1cccc(-c2ccc3c(-c4cccnc4)c(O)ccc3c2)c1]

The compound is prepared by the reaction of 1-bromo-6-(3-hydroxyphenyl)-naphthalene-2-ol (100 mg, 0.32 mmol, 1 eq) with 3-pyridineboric acid (39 mg, 0.32 mmol, 1 eq) according to method A in 21 h. Purification by column chromatography with hexane/ethyl acetate 7/3 yields the desired compound in a yield of 59%, 59 mg.

C$_{21}$H$_{15}$NO$_2$; MW 313; R$_f$ value (dichloromethane/methanol 90/10): 0.5; $^1$H-NMR (CD$_3$OD): δ 9.03 (m, 1H), 8.95 (d, J=5.7 Hz, 1H), 8.81-8.79 (m, 1H), 8.30 (dd, J=5.7 Hz, J=7.9 Hz, 1H), 8.12 (d, J=1.9 Hz, 1H), 8.04 (d, J=8.8 Hz, 1H), 7.75 (dd, J=1.9 Hz, J=8.8 Hz, 1H), 7.55 (d, J=8.5 Hz, 1H), 7.35 (d, J=9.1 Hz, 1H), 7.32 (t, J=7.9 Hz, 1H), 7.23-7.21 (m, 1H), 7.18-7.17 (m, 1H), 6.83 (ddd, J=0.9 Hz, J=2.5 Hz, J=7.9 Hz, 1H); $^{13}$C-NMR (CD$_3$OD): δ 159.1, 154.1, 151.0, 144.8, 143.2, 140.8, 133.3, 133.1, 131.0, 130.3, 128.4, 128.2, 127.2, 124.1, 119.3, 119.1, 115.4, 114.8; IR: 3091, 1581, 1493, 1276, 1209, 1180 1/cm; MS (ESI): 314 (M+H)$^+$

52.) 6-(3-Hydroxyphenyl)-1-(pyridin-4-yl)naphthalene-2-ol (60)

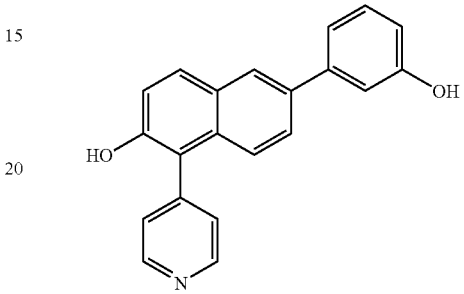

The compound is prepared by the reaction of 1-bromo-6-(3-hydroxyphenyl)-naphthalene-2-ol (100 mg, 0.32 mmol, 1 eq) with 4-pyridineboric acid (39 mg, 0.32 mmol, 1 eq) according to method A in 1 h. Purification by column chromatography with hexane/ethyl acetate 8/2 yields the desired compound in a yield of 44%, 44 mg.

C$_{21}$H$_{18}$ClNO$_2$; MW 313; R$_f$ value (dichloromethane/methanol 95/5): 0.1; $^1$H-NMR (CD$_3$OD): δ 8.95 (d, J=6.9 Hz, 2H), 8.26 (d, J=2.6 Hz, 2H), 8.13 (d, J=1.9 Hz, 1H), 8.06 (d, J=8.8 Hz, 1H), 7.77 (dd, J=1.9 Hz, J=8.8 Hz, 1H), 7.65 (d, J=8.8 Hz, 1H), 7.34 (d, J=8.8 Hz, 1H), 7.34-7.31 (m, 1H), 7.24-7.22 (m, 1H), 7.18-7.17 (m, 1H), 6.84 (ddd, J=0.9 Hz, J=2.2 Hz, J=7.9 Hz, 1H); $^{13}$C-NMR (CD$_3$OD): δ 159.0, 153.0, 149.9, 148.1, 143.5, 137.1, 133.8, 133.1, 133.0, 131.6, 130.9, 130.0, 129.9, 128.4, 127.2, 126.8, 125.2, 119.4, 119.3, 115.2, 114.8; IR: 3080, 1631, 1596, 1580, 1359, 1276, 1201, 1179 1/cm, MS (ESI): 314 (M+H)$^+$

53.) 6-(3-Hydroxyphenyl)-1-(pyrimidin-5-yl)naphthalene-2-ol (61)

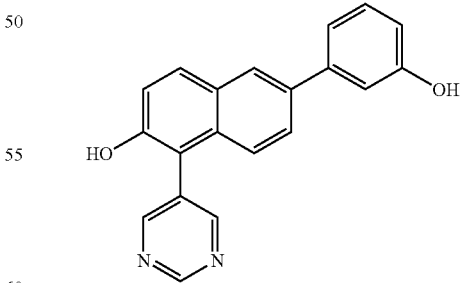

The compound is prepared by the reaction of 1-bromo-6-(3-hydroxyphenyl)-naphthalene-2-ol (150 mg, 0.48 mmol, 1 eq) with 3-pyrimidineboric acid (59.0 mg, 0.48 mmol, 1 eq) according to method A in 15 h. Purification by column chromatography with dichloromethane/methanol 99/1 yields the desired compound in a yield of 9%, 14 mg.

$C_{20}H_{14}N_2O_2$; MW 314; $R_f$ value (dichloromethane/methanol 95/5): 0.4; $^1$H-NMR (CD$_3$OD): δ 9.29 (s, 1H), 9.22 (s, 2H), 8.09 (d, J=1.9 Hz, 1H), 7.99 (d, J=8.8 Hz, 1H), 7.51 (dd, J=2.2 Hz, J=8.8 Hz, 1H), 7.37 (d, J=8.8 Hz, 1H), 7.28 (t, J=7.9 Hz, 1H), 7.20 (ddd, J=1.3 Hz, J=1.9 Hz, J=7.9 Hz, 1H), 7.18-7.15 (m, 2H), 6.87 (ddd, J=0.9 Hz, J=2.5 Hz, J=7.9 Hz, 1H); $^{13}$C-NMR (CD$_3$OD): δ 159.4, 156.5, 154.5, 144.0, 142.1 130.3, 126.7, 126.6, 126.4, 119.7, 119.4, 119.3, 116.1, 114.9, 114.8; IR: 3202, 2922, 1728, 1596, 1580, 1274 1/cm; MS (ESI): 313 (M−H)$^−$ 54.) 6-(3-Hydroxyphenyl)-1-(6-methoxypyridin-3-yl)naphthalene-2-ol (62)

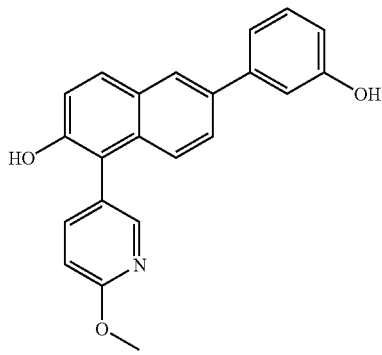 [SMILES: COc1ccc(-c2c(O)ccc3cc(-c4cccc(O)c4)ccc23)cn1]

The compound is prepared by the reaction of 1-bromo-6-(3-hydroxyphenyl)-naphthalene-2-ol (100 mg, 0.32 mmol, 1 eq) with 6-methoxypyridin-3-ylboric acid (48.6 mg, 0.32 mmol, 1 eq) according to method A in 3 h. Purification by column chromatography with hexane/ethyl acetate 8/2 yields the desired compound in a yield of 84%, 92 mg.

$C_{22}H_{17}NO_3$; MW 343; $R_f$ value (hexane/ethyl acetate 1/1): 0.6; $^1$H-NMR (CD$_3$OD): δ 8.15 (d, J=2.5 Hz, 1H), 8.01 (d, J=1.9 Hz, 1H), 7.84 (d, J=8.8 Hz, 1H), 7.72 (dd, J=2.5 Hz, J=8.5 Hz, 1H), 7.61 (dd, J=1.9 Hz, J=8.8 Hz, 1H), 7.49 (d, J=8.8 Hz, 1H), 7.29-7.26 (m, 1H), 7.26 (d, J=8.8 Hz, 1H), 7.20 (m, 1H), 7.18-7.17 (m, 1H), 6.98 (dd, J=0.6 Hz, J=8.5 Hz, 1H), 6.81 (ddd, J=0.9 Hz, J=2.5 Hz, J=8.2 Hz, 1H), 4.02 (s, 3H); $^{13}$C-NMR (CD$_3$OD): δ 164.8, 158.9, 153.6, 149.5, 143.7, 143.5, 136.8, 134.7, 130.9, 130.3, 126.9, 126.8, 125.5, 119.4, 118.9, 115.1, 114.8, 111.2, 54.2; IR: 3357, 2917, 2849, 1586, 1493 1/cm; MS (ESI): 344 (M+H)$^+$ 55.) 3-(2-Hydroxy-6-(3-hydroxyphenyl)naphthalene-1-yl)benzoic acid (63)

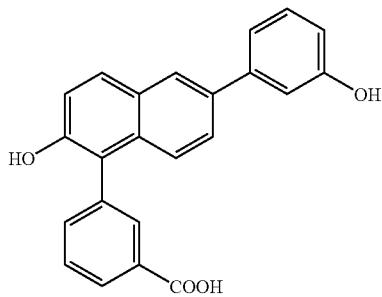 [SMILES: O=C(O)c1cccc(-c2c(O)ccc3cc(-c4cccc(O)c4)ccc23)c1]

The compound is prepared by the reaction of 1-bromo-6-(3-hydroxyphenyl)-naphthalene-2-ol (100 mg, 0.32 mmol, 1 eq) with 3-carboxybenzeneboric acid (52.7 mg, 0.32 mmol, 1 eq) according to method A over night. Purification by column chromatography with hexane/ethyl acetate 3/2 yields the desired compound in a yield of 15%, 17 mg.

$C_{23}H_{16}O_4$; MW 356; $R_f$ value (dichloromethane/methanol 90/10): 0.2; $^1$H-NMR (CD$_3$OD): δ 8.14-8.12 (m, 1H), 8.08 (m, 1H), 8.04 (d, J=1.9 Hz, 1H), 7.89 (d, J=8.5 Hz, 1H), 7.66-7.65 (m, 2H), 7.62 (dd, J=1.9 Hz, J=8.8 Hz, 1H), 7.45 (d, J=8.8 Hz, 1H), 7.33-7.28 (m, 1H), 7.28 (d, J=8.8 Hz, 1H), 7.23-7.21 (m, 1H), 7.18-7.17 (m, 1H), 6.80 (ddd, J=0.9 Hz, J=2.5 Hz, J=7.9 Hz, 1H); $^{13}$C-NMR (CD$_3$OD): 158.9, 143.7, 138.3, 137.0, 136.8, 134.3, 133.6, 130.8, 130.7, 129.5, 126.8, 126.7, 125.8, 119.5, 119.3, 115.0, 114.8; IR: 2967, 1676, 1595, 1282 1/cm; MS (ESI): 355 (M−H)$^−$ 56.) N-(3-(2-Hydroxy-6-(3-hydroxyphenyl)naphthalene-1-yl)phenyl)methanesulfonamide (64)

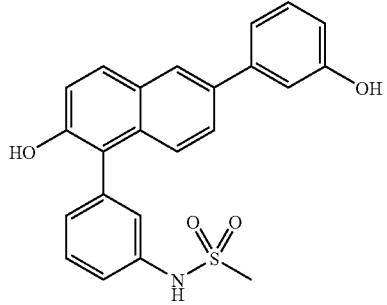 [SMILES: CS(=O)(=O)Nc1cccc(-c2c(O)ccc3cc(-c4cccc(O)c4)ccc23)c1]

The compound is prepared by the reaction of 1-bromo-6-(3-hydroxyphenyl)-naphthalene-2-ol (100 mg, 0.32 mmol, 1 eq) with N-(3-(4,4,5,5-tetramethyl-1,3,2-dioxaborolan-2-yl)phenyl)methanesulfonamide (94.3 mg, 0.32 mmol, 1 eq) according to method A in 2 h. Purification by column chromatography with hexane/ethyl acetate 3/2 yields the desired compound in a yield of 64%, 83 mg.

$C_{23}H_{19}NO_4S$; MW 405; $R_f$ value (hexane/ethyl acetate 1/1): 0.3; $^1$H-NMR (CD$_3$OD+3 drops of CDCl$_3$): δ 8.01 (d, J=1.6 Hz, 1H), 7.85 (d, J=9.1 Hz, 1H), 7.60 (dd, J=1.9 Hz, J=8.8 Hz, 1H), 7.53-7.50 (m, 2H), 7.39-7.37 (m, 1H), 7.32 (m, 1H), 7.29 (t, J=7.9 Hz, 1H), 7.26 (d, J=8.8 Hz, 1H), 7.23-7.20 (m, 2H), 7.17-7.16 (m, 1H), 6.82-6.80 (m, 1H), 3.07 (s, 3H); $^{13}$C-NMR (CD$_3$OD+3 drops of CDCl$_3$): 161.4, 155.3, 146.3, 142.1, 141.7, 139.3, 136.8, 133.4, 133.1, 133.0, 132.8, 131.2, 129.3, 129.2, 128.6, 127.0, 124.9, 123.0, 122.0, 121.9, 117.6, 117.4, 64.1; IR: 3406, 1704, 1600, 1585, 1323, 1268 1/cm; MS (ESI): 404 (M−H)⁻

57.) 6-(3-Hydroxyphenyl)-1-(4-morpholinophenyl)naphthalene-2-ol (65)

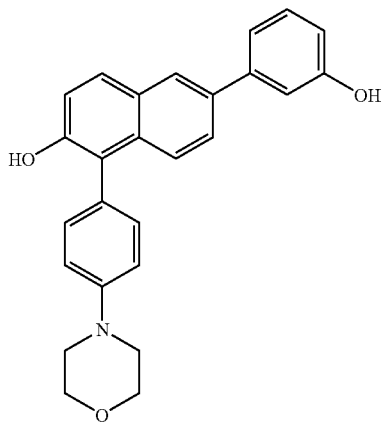 [SMILES: Oc1cccc(-c2ccc3c(-c4ccc(N5CCOCC5)cc4)c(O)ccc3c2)c1]

The compound is prepared by the reaction of 1-bromo-6-(3-hydroxyphenyl)-naphthalene-2-ol (150 mg, 0.48 mmol, 1 eq) with 4-morpholinophenylboric acid (98.6 mg, 0.48 mmol, 1 eq) according to method A in 21 h. Purification by column chromatography with dichloromethane/methanol 99/1 yields the desired compound in a yield of 7%, 13 mg.

$C_{26}H_{13}NO_3$; MW 397; $R_f$ value (dichloromethane/methanol 95/5): 0.4; ¹H-NMR (CD₃OD): δ 8.01 (d, J=1.9 Hz, 1H), 7.82 (d, J=8.8 Hz, 1H), 7.59 (dd, J=1.9 Hz, J=8.8 Hz, 1H), 7.53 (d, J=8.8 Hz, 1H), 7.33-7.31 (m, 2H), 7.28 (d, J=8.2 Hz, 1H), 7.24 (d, J=8.8 Hz, 1H), 7.22-7.20 (m, 1H), 7.18-7.16 (m, 3H), 6.80 (ddd, J=0.9 Hz, J=2.5 Hz, J=7.9 Hz, 1H), 3.94-3.92 (m, 4H), 3.29-3.27 (m, 4H); IR: 3367, 2924, 1731, 1598, 1448, 1237 1/cm, MS (ESI): 398 (M+H)⁺

58.) N-(3-(2-Hydroxy-6-(3-hydroxyphenyl)naphthalene-1-yl)phenyl)acetamide (66)

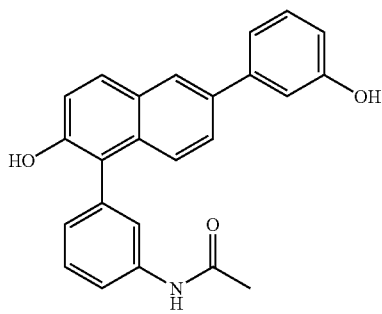 [SMILES: CC(=O)Nc1cccc(-c2c(O)ccc3cc(-c4cccc(O)c4)ccc23)c1]

The compound is prepared by the reaction of 1-bromo-6-(3-hydroxyphenyl)naphthalene-2-ol (150 mg, 0.48 mmol, 1 eq) with N-(3-(4,4,5,5-tetramethyl-1,3,2-dioxaborolan-2-yl)phenyl)acetamide (124.3 mg, 0.48 mmol, 1 eq) according to method A in 2 h. Purification by column chromatography with hexane/ethyl acetate 8/2 yields the desired compound in a yield of 77%, 136 mg.

$C_{24}H_{19}NO_3$; MW 369; $R_f$ value (dichloromethane/methanol 95/5): 0.2; ¹H-NMR (CD₃OD): δ 8.02 (d, J=1.9 Hz, 1H), 7.85 (d, J=8.8 Hz, 1H), 7.72 (ddd, J=0.9 Hz, J=2.2 Hz, J=8.2 Hz, 1H), 7.59 (dd, J=2.2 Hz, J=9.1 Hz, 1H), 7.56-7.55 (m, 1H), 7.51 (d, J=8.8 Hz, 1H), 7.49 (t, J=7.9 Hz, 1H), 7.29 (t, J=7.9 Hz, 1H), 7.27 (d, J=8.8 Hz, 1H), 7.21-7.19 (m, 1H), 7.17-7.15 (m, 2H), 6.80 (ddd, J=0.9 Hz, J=2.5 Hz, J=8.2 Hz, 1H), 2.18 (s, 3H); ¹³C-NMR (CD₃OD): δ 175.5, 174.3, 161.4, 155.2, 146.3, 142.5, 141.0, 139.2, 137.0, 133.4, 132.9, 132.8, 132.3, 130.7, 129.1, 128.7, 126.7, 125.2, 122.8, 122.0, 121.9, 117.5, 117.3, 17.0; IR: 3329, 1706, 1665, 1600, 1585, 1489, 1241 1/cm; MS (ESI): 370 (M+H)⁺

59.) 4-(4-(2-Hydroxy-6-(3-hydroxyphenyl)naphthalene-1-yl)phenylamino)-4-oxobutanoic acid (67)

The compound is prepared by the reaction of 1-bromo-6-(3-hydroxyphenyl)-naphthalene-2-ol (100 mg, 0.32 mmol, 1 eq) with 4-oxo-4-(4-(4,4,5,5-tetramethyl-1,3,2-dioxaborolan-2-yl)phenylamino)butanoic acid (101.3 mg, 0.32 mmol, 1 eq) according to method A in 10 min. Purification by column chromatography with dichloromethane/methanol 90/10 yields the desired compound in a yield of 12%, 16 mg.

$C_{26}H_{21}NO_5$; MW 427; $R_f$ value (dichloromethane/methanol 95/5): 0.5; ¹H-NMR (CD₃OD): δ 8.02 (d, J=1.8 Hz, 1H), 7.84 (d, J=8.8 Hz, 1H), 7.74-7.72 (m, 2H), 7.60 (dd, J=1.8 Hz, J=8.8 Hz, 1H), 7.52 (d, J=8.8 Hz, 1H), 7.38-7.36 (m, 2H), 7.30 (t, J=7.9 Hz, 1H), 7.25 (d, J=8.8 Hz, 1H), 7.22-7.20 (m, 1H), 7.17-7.16 (m, 1H), 6.80 (ddd, J=0.9 Hz, J=2.4 Hz, J=7.9 Hz, 1H), 2.81-2.75 (m, 4H); ¹³C-NMR (CD₃OD): δ 171.3, 142.4, 132.0, 131.3, 129.4, 128.9, 125.1, 124.7, 121.2, 119.8, 118.1, 117.9, 113.3, 30.8, 28.5; IR: 3322, 2923, 1711, 1665, 1595, 1521, 1260 1/cm; MS (ESI): 445 (M+H$_2$O)$^+$

60.) 3-(2-Methoxy-6-(3-methoxyphenyl)naphthalene-1-yl)-N-(thiazol-2-yl)benzenesulfonamide

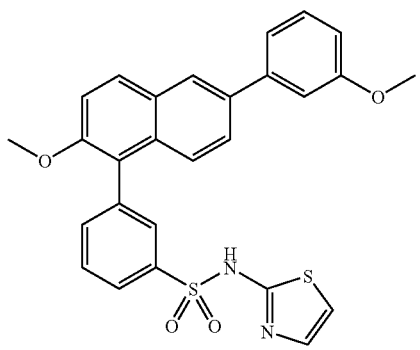

The compound is prepared by the reaction of 3-bromo-N-(thiazol-2-yl)benzenesulfonamide (88.8 mg, 0.28 mmol, 1 eq) with 2-methoxy-6-(3-methoxyphenyl)-naphthalene-1-ylboric acid (100 mg, 0.36 mmol, 1.3 eq) according to method C. Purification by column chromatography with dichloromethane/methanol 95/5 yields the desired compound in a yield of 14%, 19 mg.

C$_{24}$H$_{18}$N$_2$O$_4$S$_2$; MW 474; R$_f$ value (dichloromethane/methanol 95/5): 0.6; $^1$H-NMR (CD$_3$OD): δ 7.99 (d, J=1.9 Hz, 1H), 7.96-7.95 (m, 1H), 7.94-7.93 (m, 1H), 7.92 (d, J=8.8 Hz, 1H), 7.56-7.52 (m, 3H), 7.36 (d, J=8.8 Hz, 1H), 7.33 (m, 2H), 7.24-7.22 (m, 1H), 7.18-7.17 (m, 1H), 6.97 (d, J=4.7 Hz, 1H), 6.98-6.87 (m, 1H), 6.43 (d, J=4.4 Hz, 1H), 3.85 (s, 3H), 3.76 (s, 3H); IR: 3054, 1535, 1255, 1148, 1130 1/cm

61.) 3-(2-Methoxy-6-(3-methoxyphenyl)naphthalene-1-yl)-N-(5-methyl-1,3,4-thiadiazol-2-yl)benzenesulfonamide

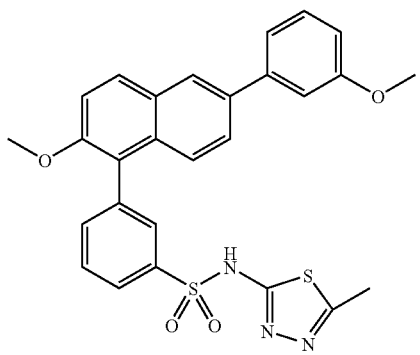

The compound is prepared by the reaction of 3-bromo-N-(5-methyl-1,3,4-thiadiazol-2-yl)benzenesulfonamide (92.4 mg, 0.28 mmol, 1 eq) with 2-methoxy-6-(3-methoxyphenyl) naphthalene-1-ylboric acid (100 mg, 0.36 mmol, 1.3 eq) according to method C. The raw product was not characterized, but directly subjected to ether cleavage.

Formation of Amides

62.) 3-[3-Methoxy-5-(6-methoxynaphthalene-2-yl)phenyl]-N-methylpropionic amide

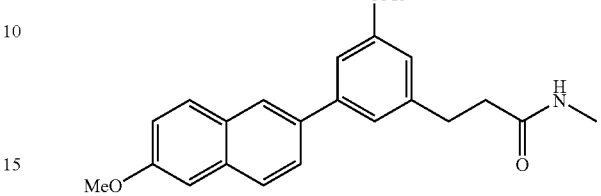

A suspension of (E)-3-[3-methoxy-5-(6-methoxynaphthalene-2-yl)phenyl]-N-methylacrylic amide (100 mg, 0.30 mmol, 1 eq) and Pd(OH)$_2$ (2.82 mg) in ethanol (1 ml) and THF (0.4 ml) is stirred for 19 h at RT under a hydrogen atmosphere. Filtration and concentration of the reaction mixture on a rotary evaporator yields the desired product in quantitative yield.

C$_{22}$H$_{23}$NO$_3$; MW 349; $^1$H-NMR (DMSO): δ 8.12 (d, J=1.6 Hz, 1H), 7.90 (d, J=8.8 Hz, 1H), 7.89 (d, J=8.2 Hz, 1H), 7.78 (dd, J=1.9 Hz, J=8.5 Hz, 1H), 7.34 (d, J=2.5 Hz, 1H), 7.20-7.18 (m, 2H), 7.13-7.12 (m, 1H), 6.78 (m, 1H), 3.89 (s, 3H), 3.83 (s, 3H), 2.89-2.86 (m, 2H), 2.57 (s, 3H), 2.44-2.41 (m, 2H); $^{13}$C-NMR (CD$_3$OD): δ 160.4, 157.9, 142.8, 142.6, 129.3, 128.4, 126.9, 125.4, 125.0, 124.7, 119.3, 118.7, 112.3, 110.2, 106.6, 105.2, 54.4, 38.8, 37.4, 29.5; IR: 3326, 2935, 1561 1/cm

63.) 3-[3-Methoxy-5-(6-methoxynaphthalene-2-yl)phenyl]-N-phenylpropionic amide

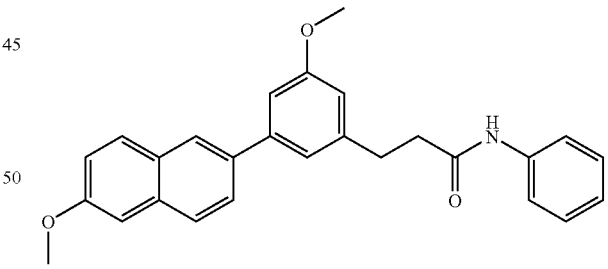

A suspension of (E)-3-[3-methoxy-5-(6-methoxynaphthalene-2-yl)phenyl]-N-phenylacrylic acid amide (70 mg, 0.17 mmol, 1 eq) and Pd(OH)$_2$ (2.5 mg) in ethanol (1 ml) and THF (0.4 ml) is stirred for 20 h at RT under a hydrogen atmosphere. Filtration and concentration of the reaction mixture on a rotary evaporator yields the desired product in quantitative yield (70 mg).

C$_{27}$H$_{25}$NO$_3$; MW 411; $^1$H-NMR (CDCl$_3$): δ 7.90 (d, J=1.6 Hz, 1H), 7.76 (d, J=8.8 Hz, 1H), 7.73 (d, J=8.8 Hz, 1H), 7.65 (dd, J=1.9 Hz, J=8.5 Hz, 1H), 7.44-7.42 (m, 2H), 7.29-7.26 (m, 2H), 7.16-7.14 (m, 3H), 7.09-7.06 (m, 2H), 6.78 (m, 1H), 3.92 (s, 3H), 3.84 (s, 3H), 3.12-3.09 (m, 2H), 2.72-2.69 (m,

2H); $^{13}$C-NMR (CDCl$_3$): δ 136.1, 129.0, 126.0, 125.7, 125.6, 119.9, 119.2, 105.6, 55.4, 55.3, 38.9, 37.5; IR: 3313, 2958, 1593 1/cm

64.) N-[2-Methoxy-4-(6-methoxy-2-naphthyl)phenyl]acetamide

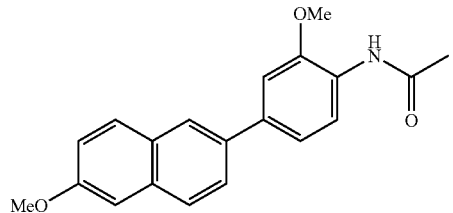 [SMILES: COc1ccc2cc(-c3ccc(NC(C)=O)c(OC)c3)ccc2c1]

To a solution of 2-methoxy-4-(6-methoxy-2-naphthyl) aniline (140 mg, 0.50 mmol, 1 eq) in 20 ml of dry dichloromethane are added acetyl chloride (64 μl, 71 mg, 0.91 mmol, 1.8 eq) and trace amounts of DMAP (dimethylaminopyridine). After stirring for 18 h at RT, the reaction mixture is stopped by adding a 2% sodium carbonate solution, the phases are separated, and the aqueous phase is extracted with dichloromethane. The combined organic phases are dried over magnesium sulfate, filtered and concentrated in vacuum on a rotary evaporator. Purification by column chromatography with a gradient of dichloromethane/methanol 10/0 to 9.8/0.2 yielded the desired product in a yield of 66%, 108 mg.

C$_{20}$H$_{19}$NO$_3$; MW 321; $^1$H-NMR (CDCl$_3$): δ 8.45 (d, J=8.5 Hz, 1H), 7.92 (s, 1H), 7.78 (dd, J=3.1 Hz, J=8.5 Hz, 3H), 7.67 (dd, J=1.9 Hz, J=8.5 Hz, 1H), 7.29 (dd, J=1.9 Hz, J=8.2 Hz, 1H), 7.19-7.15 (m, 3H), 3.98 (s, 3H), 3.94 (s, 3H), 2.23 (s, 3H); $^{13}$C-NMR (CDCl$_3$): δ 168.1, 157.7, 148.0, 136.8, 136.1, 133.7, 129.6, 129.2, 127.3, 126.9, 125.9, 125.2, 120.0, 119.9, 119.2, 108.8, 106.0, 55.8, 55.4, 24.9; IR: 3419, 2936, 2840, 1682, 1605, 1528, 1501 1/cm

65.) N-[2-Methoxy-4-(6-methoxy-2-naphthyl)phenyl]benzamide

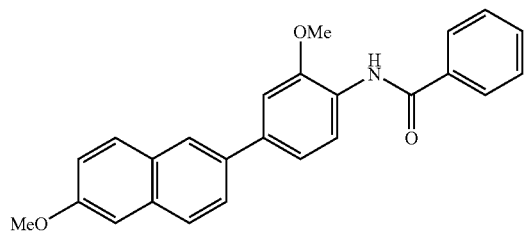 [SMILES: COc1ccc2cc(-c3ccc(NC(=O)c4ccccc4)c(OC)c3)ccc2c1]

To a solution of 2-methoxy-4-(6-methoxy-2-naphthyl) aniline (82 mg, 0.29 mmol, 1 eq) in 10 ml of dry dichloromethane are added benzoyl chloride (0.1 ml, 123 mg, 0.88 mmol, 3 eq) and trace amounts of DMAP. After stirring for 18 h at RT, the reaction mixture is stopped by adding a 2% sodium carbonate solution, the phases are separated, and the aqueous phase is extracted with dichloromethane. The combined organic phases are dried over magnesium sulfate, filtered and concentrated in vacuum on a rotary evaporator. Purification by column chromatography with a gradient of hexane/ethyl acetate 9/1 to 1/1 yielded the desired product in a yield of 90% (101 mg).

C$_{25}$H$_{21}$NO$_3$; MW 383; $^1$H-NMR (CDCl$_3$): δ 8.63 (d, J=8.5 Hz, 1H), 8.60 (s, 1H), 7.96-7.91 (m, 3H), 7.81-7.78 (m, 2H), 7.71 (dd, J=1.9 Hz, J=8.5 Hz, 1H), 7.56-7.50 (m, 3H), 7.36 (dd, J=1.9 Hz, J=8.2 Hz, 1H), 7.24 (d, J=1.9 Hz, 1H), 7.17 (m, 2H), 4.03 (s, 3H), 3.94 (s, 3H); $^{13}$C-NMR (CDCl$_3$): δ 165.2, 157.8, 148.5, 137.1, 136.1, 135.3, 133.8, 131.8, 129.7, 129.2, 128.8, 127.3, 127.1, 127.0, 125.9, 125.3, 120.1, 120.0, 119.2, 108.9, 105.6, 56.0, 55.4; IR: 3430, 2939, 2839, 1672, 1605, 1528, 1502 1/cm

66.) 3-Methoxy-7-(3-methoxyphenyl)-N-methyl-2-naphthamide

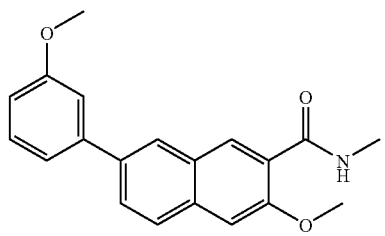 [SMILES: CNC(=O)c1cc2cc(-c3cccc(OC)c3)ccc2cc1OC]

3-Methoxy-7-(3-methoxyphenyl)-2-naphthoic acid (323 mg, 1.05 mmol, 1 eq), EDCI (1 eq) and hydroxybenzotriazole (1 eq) are dissolved in 50 ml of dichloromethane. To this solution, cooled at 0° C., are added dropwise methylamine (1 eq) and triethylamine (1 eq) in 40 ml of dry dichloromethane. The reaction mixture is boiled under reflux for 1.5 h, and after cooling, the reaction is stopped by adding 20 ml of 0.1 M HCl. The organic phase is separated, washed with saturated sodium carbonate and chloride solutions, dried over magnesium sulfate, filtered and concentrated in vacuum on a rotary evaporator. Purification by column chromatography with hexane/ethyl acetate 8/2 as the eluent yielded the desired product in a yield of 74%, 250 mg.

C$_{20}$H$_{18}$NO$_4$; MW 321; $^1$H-NMR (CDCl$_3$): δ 8.80 (s, 1H), 8.07 (s, 1H), 7.93 (bs, 1H), 7.79-7.74 (m, 2H), 7.38 (t, J=7.6 Hz, 1H), 7.26 (d, J=7.6 Hz, 1H), 7.20 (m, 2H), 6.92-6.90 (dd, J=2.7 Hz, J=8.2 Hz, 1H), 4.05 (s, 3H), 3.87 (s, 3H), 3.06 (s, 1.5H), 3.05 (s, 1.5H); $^{13}$C-NMR (CDCl$_3$): δ 165.8, 160.1, 155.0, 142.2, 137.2, 134.9, 134.1, 129.9, 128.5, 127.9, 127.0, 126.7, 122.8, 119.8, 112.9, 112.8, 106.3, 56.0, 55.4, 26.8; IR: 3402, 2944, 2837, 1652, 1599, 1542, 1488, 1203 1/cm; MS (ESI): 322 (M+H)$^+$

67.) 3-Methoxy-7-(3-methoxyphenyl)-N-phenyl-2-naphthamide

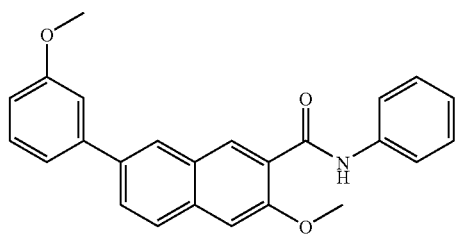 [SMILES: COc1cccc(-c2ccc3cc(OC)c(C(=O)Nc4ccccc4)cc3c2)c1]

3-Methoxy-7-(3-methoxyphenyl)-2-naphthoic acid (323 mg, 1.05 mmol, 1 eq), EDCI (1 eq) and hydroxybenzotriazole (1 eq) are dissolved in 50 ml of dry dichloromethane. To this solution, cooled at 0° C., are added dropwise aniline (1 eq) and triethylamine (1 eq) in 40 ml of dry dichloromethane. The reaction mixture is boiled under reflux for 1.5 h, and after cooling, the reaction is stopped by adding 20 ml of 0.1 M HCl. The organic phase is separated, washed with saturated sodium carbonate and chloride solutions, dried over magnesium sulfate, filtered and concentrated in vacuum on a rotary evaporator. Purification by column chromatography with hexane/ethyl acetate 8/2 and 6/4 as the eluent yielded the desired product in a yield of 70%, 282 mg.

$C_{25}H_{21}NO_3$; MW 383; $^1$H-NMR (CDCl$_3$): δ 9.89 (bs, 1H), 8.89 (s, 1H), 8.10 (s, 1H), 7.83-7.78 (m, 2H), 7.71 (d, J=7.6 Hz, 2H), 7.41-7.36 (m, 3H), 7.28 (m, 2H), 7.21 (m, 1H), 7.14 (t, J=7.2 Hz, 1H), 6.92 (dd, J=1.9 Hz, J=7.6 Hz, 1H); $^{13}$C-NMR (CDCl$_3$): δ 163.0, 160.1, 154.6, 142.2, 138.4, 137.5, 135.1, 134.7, 130.7, 130.0, 129.1, 128.7, 128.3, 127.1, 126.8, 124.3, 123.1, 120.6, 119.8, 113.0, 112.9, 106.7, 56.3, 55.4; IR: 3352, 2940, 2836, 1670, 1597, 1544, 1290, 1199 1/cm; MS (ESI): 384 (M+H)$^+$

Method D: Amide Formation

A solution of the corresponding acid (1 eq) and amine (1 eq) in 20 ml of dichloromethane is added dropwise to a mixture, cooled at 0° C., of EDCI (1 eq) and hydroxybenzotriazole (1 eq) in 150 ml of dichloromethane. The reaction mixture is stirred at RT for 1 to 4 days. After the solvent has been removed in vacuum on a rotary evaporator, the raw product is dissolved in ethyl acetate and washed with saturated sodium carbonate solution and sodium chlorid solution. The organic phase is separated, dried over magnesium sulfate, filtered and concentrated in vacuum on a rotary evaporator. Purification was performed by column chromatography with silica gel as a stationary phase.

68.) 3-Methoxy-5-(6-methoxynaphthalene-2-yl)-N-methylbenzamide

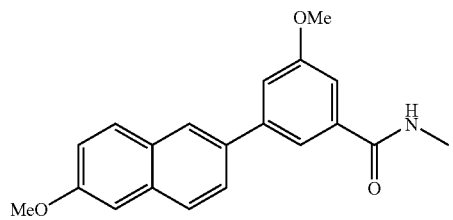 [SMILES: CNC(=O)c1cc(OC)cc(-c2ccc3cc(OC)ccc3c2)c1]

The compound was prepared by reaction of 3-methoxy-5-(6-methoxy-naphthalene-2-yl)benzoic acid (500 mg, 1.62 mmol, 1 eq) with 33% methylamine solution (1 eq) according to method D. Purification by column chromatography with hexane/ethyl acetate 1/1 as the eluent yielded the desired product in a yield of 28%, 148 mg.

$C_{20}H_{19}NO_3$; MW 321; $^1$H-NMR (CDCl$_3$): δ 7.96 (d, J=1.3 Hz, 1H), 7.79 (d, J=9.1 Hz, 1H), 7.78 (d, J=9.1 Hz, 1H), 7.67 (dd, J=1.9 Hz, J=8.2 Hz, 1H), 7.58 (t, J=1.6 Hz, 1H), 7.32 (dd, J=1.6 Hz, J=2.2 Hz, 1H), 7.30 (dd, J=1.6 Hz, J=2.5 Hz, 1H), 7.17 (dd, J=2.5 Hz, J=8.5 Hz, 1H), 7.15 (d, J=2.5 Hz, 1H), 3.93 (s, 3H), 3.91 (s, 3H), 3.03 (s, 3H); $^{13}$C-NMR (CDCl$_3$): δ 158.0, 143.1, 136.7, 135.3, 129.0, 127.4, 125.8, 119.4, 117.8, 116.3, 110.7, 105.6, 55.6, 26.9; IR: 3296, 2996, 2934, 1641, 1595, 1551, 1261 1/cm

69.) 3-Methoxy-5-(6-methoxynaphthalene-2-yl)-N-phenylbenzamide

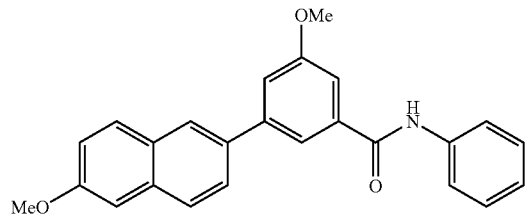 [SMILES: COc1cc(C(=O)Nc2ccccc2)cc(-c2ccc3cc(OC)ccc3c2)c1]

The compound was prepared by reaction of 3-methoxy-5-(6-methoxynaphthalene-2-yl)benzoic acid (500 mg, 1.62 mmol, 1 eq) with aniline (1 eq) according to method D. Purification by column chromatography with hexane/dichloromethane 1/1 as the eluent yielded the desired product in a yield of 11%, 68 mg.

$C_{25}H_{21}NO_3$; MW 383; $^1$H-NMR (CDCl$_3$): δ 7.97 (s, 1H), 7.93 (bs, 1H), 7.80 (d, J=8.5 Hz, 1H), 7.77 (d, J=9.1 Hz, 1H), 7.69-7.65 (m, 4H), 7.38-7.35 (m, 4H), 7.18-7.13 (m, 3H), 3.93 (s, 3H), 3.91 (s, 3H); $^{13}$C-NMR (CDCl$_3$): δ 160.4, 158.0, 137.9, 137.0, 134.1, 129.8, 129.1, 127.5, 125.9, 125.7, 124.6, 120.2, 119.4, 117.9, 116.7, 110.9, 105.6, 55.7; IR: 3276, 2996, 2934, 1643, 1593, 1536, 1440, 1256 1/cm

70.) (E)-3-[3-Methoxy-5-(6-methoxynaphthalene-2-yl)phenyl]-N-methylacrylamide

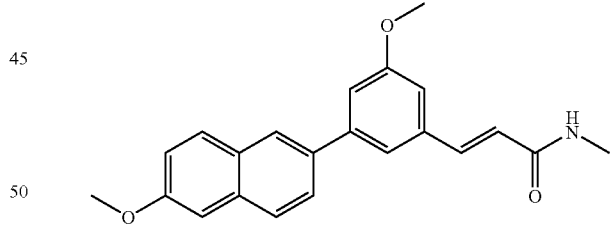

The compound was prepared by reaction of (E)-3-[3-methoxy-5-(6-methoxynaphthalene-2-yl)phenyl]acrylic acid (300 mg, 0.89 mmol, 1 eq) with 33% methylamine (1 eq) according to method D. Purification by column chromatography with hexane/ethyl acetate 2/1 as the eluent yielded the desired product in a yield of 53%, 200 mg.

$C_{22}H_{21}NO_3$; MW 347; $^1$H-NMR (DMSO): δ 8.21 (d, J=1.6 Hz, 1H), 7.91 (d, J=8.8 Hz, 2H), 7.84 (dd, J=1.9 Hz, J=8.5 Hz, 1H), 7.56 (t, J=1.3 Hz, 1H), 7.48 (d, J=15.8 Hz, 1H), 7.36 (m, 1H), 7.33 (dd, J=1.9 Hz, J=2.5 Hz, 1H), 7.21 (dd, J=2.5 Hz, J=8.8 Hz, 1H), 7.13 (dd, J=1.6 Hz, J=1.9 Hz, 1H), 6.73 (d,

J=15.8 Hz, 1H), 3.90 (s, 3H), 3.89 (s, 3H), 2.72 (s, 3H); IR: 3279, 2931, 1734, 1656, 1579, 1260, 1219, 1199 1/cm

71.) (E)-3-[3-Methoxy-5-(6-methoxynaphthalene-2-yl)phenyl]-N-phenylacrylamide

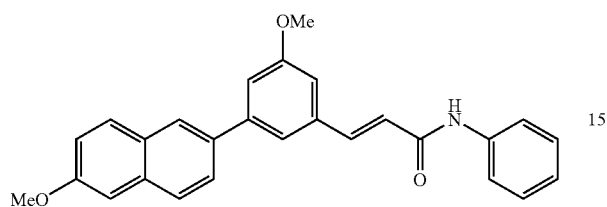

The compound was prepared by reaction of (E)-3-[3-methoxy-5-(6-methoxy-naphthalene-2-yl)phenyl]acrylic acid (300 mg, 0.89 mmol, 1 eq) with aniline (1 eq) according to method D. Purification by column chromatography with hexane/ethyl acetate 2/1 as the eluent yielded the desired product in a yield of 62%, 227 mg.

$C_{27}H_{23}NO_3$; MW 409; $^1$H-NMR (CDCl$_3$): δ 7.90 (d, J=1.6 Hz, 1H), 7.78 (d, J=15.4 Hz, 1H), 7.76 (d, J=8.5 Hz, 1H), 7.75 (d, J=8.8 Hz, 1H), 7.71-7.69 (m, 1H), 7.62 (dd, J=1.9 Hz, J=8.5 Hz, 2H), 7.39 (m, 1H), 7.33-7.30 (m, 2H), 7.19 (dd, J=1.6 Hz, J=2.2 Hz, 1H), 7.16 (dd, J=2.5 Hz, J=8.8 Hz, 1H), 7.13 (d, J=2.5 Hz, 1H), 7.12-7.09 (m, 1H), 6.99 (m, 1H), 6.64 (d, J=15.4 Hz, 1H), 3.92 (s, 3H), 3.85 (s, 3H); $^{13}$C-NMR (CDCl$_3$): δ 171.2, 167.7, 160.3, 157.9, 143.2, 142.3, 136.4, 135.5, 134.0, 130.9, 129.7, 129.1, 127.3, 125.8, 125.7, 119.6, 119.3, 114.7, 111.6, 105.6, 55.4; IR: 3257, 2934, 1725, 1659, 1588 1/cm

72.) (E)-3-(2-Methoxy-6-(3-methoxyphenyl)naphthalene-1-yl)-N-methylacrylamide

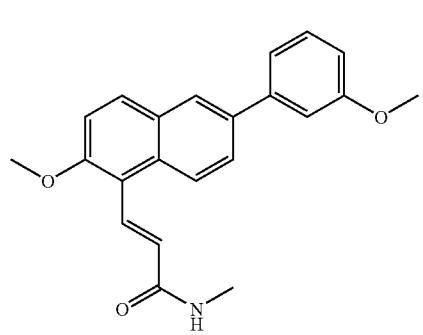

The compound was prepared by reaction of (E)-3-(2-methoxy-6-(3-methoxyphenyl)naphthalene-1-yl)acrylic acid (200 mg, 0.60 mmol, 1 eq) with 33% methylamine (1 eq) according to method D. Purification by column chromatography was not necessary. The desired compound was obtained in quantitative yield.

$C_{21}H_{22}NO_3$; MW 347; R$_f$ value (ethyl acetate): 0.6; $^1$H-NMR (CDCl$_3$): δ 8.25 (d, J=15.6 Hz, 1H), 8.25 (d, J=9.1 Hz, 1H), 7.96 (d, J=1.9 Hz, 1H), 7.87 (d, J=9.1 Hz, 1H), 7.74 (dd, J=1.9 Hz, J=8.8 Hz, 1H), 7.37 (t, J=7.9 Hz, 1H), 7.30 (d, J=9.1 Hz, 1H), 7.29-7.27 (m, 1H), 7.22 (m, 1H), 6.90 (ddd, J=0.9 Hz, J=2.5 Hz, J=8.2 Hz, 1H), 6.69 (d, J=15.8 Hz, 1H), 4.00 (s, 3H), 3.88 (s, 3H), 2.93 (s, 3H); $^{13}$C-NMR (CDCl$_3$): δ 163.7, 160.1, 142.2, 136.3, 133.8, 131.1, 130.0, 129.3, 126.7, 126.2, 126.0, 124.2, 119.7, 117.4, 113.4, 112.9, 112.7, 56.3, 55.4, 26.5; IR: 3278, 2927, 2853, 1643, 1577 1/cm

73.) (E)-3-(2-Methoxy-6-(3-methoxyphenyl)naphthalene-1-yl)-N-phenylacrylamide

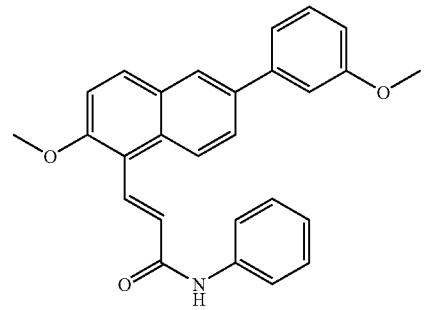

The compound was prepared by reaction of (E)-3-(2-methoxy-6-(3-methoxyphenyl)naphthalene-1-yl)acrylic acid (200 mg, 0.60 mmol, 1 eq) with aniline (1 eq) according to method D. Characterization of this compound was not effected. The raw product was directly employed for ether cleavage.

74.) 2-Methoxy-6-(3-methoxyphenyl)-N-methyl-1-naphthamide

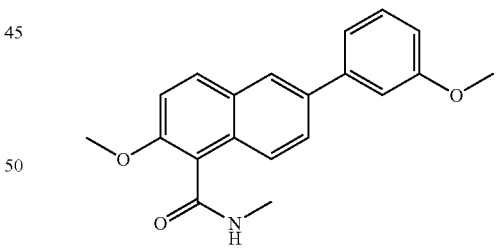

The compound was prepared by reaction of 2-methoxy-6-(3-methoxyphenyl)-1-naphthoic acid (300 mg, 0.97 mmol, 1 eq) with 33% methylamine (1 eq) according to method D. Purification by column chromatography was not necessary. The desired compound was obtained in quantitative yield (311 mg).

$C_{20}H_{19}NO_3$; MW 321; R$_f$ value (ethyl acetate): 0.6; $^1$H-NMR (CDCl$_3$): δ 8.00 (d, J=1.9 Hz, 1H), 7.96 (d, J=1.8 Hz, 1H), 7.92 (d, J=8.8 Hz, 1H), 7.75 (dd, J=1.8 Hz, J=8.8 Hz, 1H), 7.39 (t, J=7.7 Hz, 1H), 7.29 (d, J=8.8 Hz, 1H), 7.28 (m, 1H), 7.22 (m, 1H), 6.94 (ddd, J=0.6 Hz, J=2.7 Hz, J=5.5 Hz, 1H), 3.97 (s, 3H), 3.89 (s, 3H), 3.14 (s, 3H); IR: 2992, 2939, 1637, 1595, 1528 1/cm

75.) 2-Methoxy-6-(3-methoxyphenyl)-N-phenyl-1-naphthamide

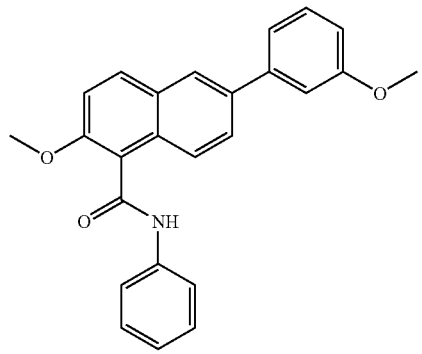

The compound was prepared by reaction of 2-methoxy-6-(3-methoxyphenyl)-1-naphthoic acid (300 mg, 0.97 mmol, 1 eq) with aniline (1 eq) according to method D. Purification by column chromatography with hexane/ethyl acetate 2/1 as the eluent yielded the desired compound in a yield of 85%, 316 mg.

$C_{25}H_{21}NO_3$, MW 383, $R_f$ value (ethyl acetate): 0.9; $^1$H-NMR (CDCl$_3$): 8.15 (d, J=8.8 Hz, 1H), 8.00 (d, J=1.5 Hz, 1H), 7.98 (d, J=9.1 Hz, 1H), 7.77 (dd, J=1.8, J=8.8 Hz, 1H), 7.73 (d, J=7.9 Hz, 2H), 7.40 (q, J=8.2 Hz, 3H), 7.35 (t, J=9.1 Hz, 1H), 7.29 (m, 1H), 7.19 (t, J=2.1 Hz, 1H), 7.16 (m, 1H), 6.93 (dd, J=2.1 Hz, J=8.2 Hz, 1H), 4.02 (s, 3H), 3.89 (s, 3H); IR: 3324, 2944, 2844, 1650, 1597, 1532, 1491, 1438, 1250 1/cm

76.) 2-Methoxy-N,6-bis(3-methoxyphenyl)-1-naphthamide

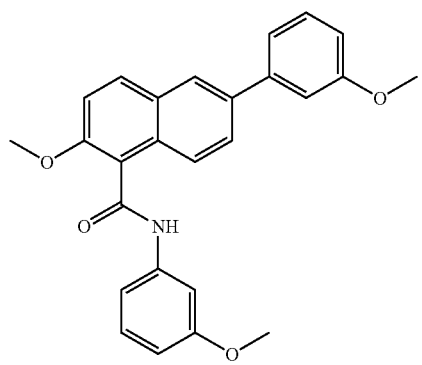

The compound was prepared by reaction of 2-methoxy-6-(3-methoxyphenyl)-1-naphthoic acid (300 mg, 0.97 mmol, 1 eq) with m-anisole (1 eq) according to method D. Purification by column chromatography with hexane/ethyl acetate 2/1 as the eluent yielded the desired compound in a yield of 29%, 116 mg.

$C_{26}H_{23}NO_4$, MW 413, $R_f$ value (hexane/ethyl acetate 1/1): 0.5; $^1$H-NMR (CDCl$_3$): δ 8.14 (d, J=8.8 Hz, 1H), 8.00 (d, J=1.5 Hz, 1H), 7.98 (d, J=9.1 Hz, 1H), 7.77 (dd, J=1.8, J=8.8 Hz, 1H), 7.75 (s, 1H), 7.56 (t, J=2.1 Hz, 1H), 7.40 (t, J=7.9 Hz, 1H), 7.34 (d, J=8.8 Hz, 1H), 7.30 (m, 1H), 7.23 (m, 1H), 7.15 (dd, J=0.9, J=7.9 Hz, 1H), 6.93 (ddd, J=0.6, J=2.4, J=8.2 Hz, 1H), 6.73 (dd, J=2.1, J=8.2 Hz, 1H), 4.01 (s, 3H), 3.89 (s, 3H), 3.87 (s, 3H); IR: 2941, 2842, 1651, 1595, 1537, 1490 1/cm

77.) tert-Butyl 4-(2-methoxy-6-(3-methoxyphenyl)-1-naphthoyl)piperazine-1-carboxylate

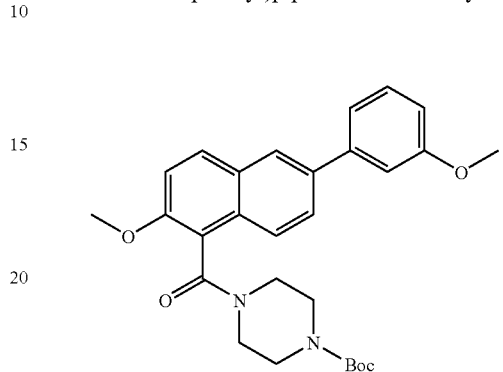

The compound was prepared by reaction of 2-methoxy-6-(3-methoxyphenyl)-1-naphthoic acid (300 mg, 0.97 mmol, 1 eq) with Boc-piperazine (1 eq) according to method D. Characterization of the compound was not effected. The raw product was directly employed for ether cleavage.

Method E: Amide Formation

2-Methoxy-6-(3-methoxyphenyl)-1-naphthoic acid or 2-hydroxy-6-(3-hydroxyphenyl)-1-naphthoic acid (1 eq) are stirred with thionyl chloride (10 eq) under a nitrogen atmosphere. Thereafter, the excess thionyl chloride is removed on a rotary evaporator. The residue is dissolved in dry THF or DME and added to the corresponding amine suspended in dry THF or dichloromethane and cooled at 0° C., followed by stirring at 0° C. for 1 h. The reaction mixture is further stirred over night at RT. After the solvent has been removed on a rotary evaporator, purification by column chromatography is effected.

78.) (2-Methoxy-6-(3-methoxyphenyl)naphthalene-1-yl)(morpholino)methanone

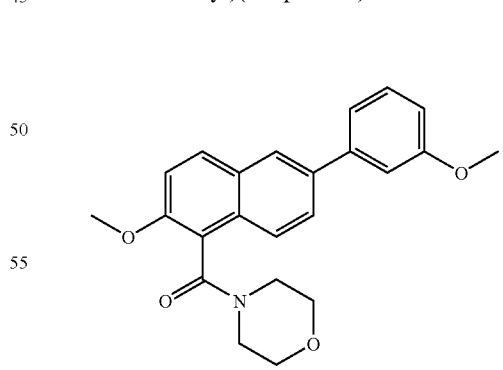

2-Methoxy-6-(3-methoxyphenyl)-1-naphthoic acid (200 mg, 0.65 mmol, 1 eq) is boiled under reflux with 5 ml of thionyl chloride under a nitrogen atmosphere for 30 min according to method E. The residue is dissolved in dry THF and added to 1 ml of morpholine cooled at 0° C. The reaction mixture is boiled under reflux over night. After the solvent has been removed on a rotary evaporator, purification is effected by column chromatography with dichloromethane/methanol 95/5 as the eluent. Characterization of the compound was not effected. The raw product was directly employed for ether cleavage.

79.) (2-Hydroxy-6-(3-hydroxyphenyl)naphthalene-1-yl)(piperidin-1-yl)methanone (51)

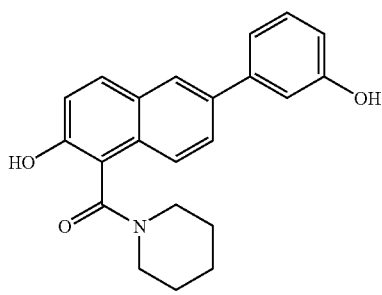

2-Hydroxy-6-(3-hydroxyphenyl)-1-naphthoic acid (160 mg, 0.57 mmol, 1 eq) is stirred with 140 µl of thionyl chloride at 0° C. for 1 h. Thereafter, the excess thionyl chloride is removed on a rotary evaporator. The residue is dissolved in 5 ml of dry DME and added to a mixture, cooled at 0° C., of piperidine in 5 ml of dry dichloromethane. The reaction mixture is stirred at RT over night. Removing the solvent on a rotary evaporator followed by purification by column chromatography with dichloromethane/methanol 95/5 as the eluent yields the desired product in a yield of 8%, 16 mg.

$C_{22}H_{21}N_1O_3$, MW 347; $R_f$ value (dichloromethane/methanol 93/7): 0.4; $^1$H-NMR (CD$_3$OD): 8.04 (d, J=1.9 Hz, 1H), 7.90 (d, J=8.8 Hz, 1H), 7.77 (dd, J=1.9 Hz, J=8.8 Hz, 1H), 7.66 (d, J=8.8 Hz, 1H), 7.30 (t, J=7.9 Hz, 1H), 7.23-7.21 (m, 1H), 7.20 (d, J=8.8 Hz, 1H), 7.17 (m, 1H), 6.82 (ddd, J=0.9 Hz, J=2.5 Hz, J=8.2 Hz, 1H), 3.98 (m, 1H), 3.87-3.83 (m, 1H), 3.69-3.67 (m, 1H), 3.31-3.29 (m, 1H), 1.81-1.79 (m, 3H), 1.75-1.36 (m, 3H)

80.) 2-Methoxy-6-(3-methoxyphenyl)-N-(thiazo-2-yl)-1-naphthamide

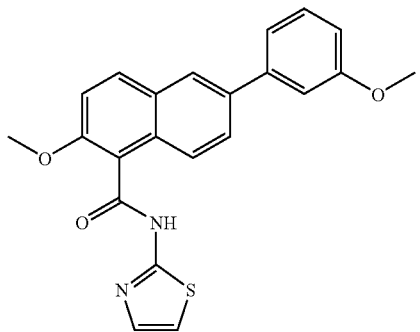

The compound was prepared by reaction of 2-methoxy-6-(3-methoxyphenyl)-1-naphthoic acid (450 mg, 1.46 mmol, 1 eq) with 2-aminothiazole (90 mg, 0.87 mmol, 0.6 eq) according to method E. Characterization of the compound was not effected. The raw product was directly employed for ether cleavage.

$C_{22}H_{18}O_3N_2S$, MW 390

81.) N-(3,4-Dimethylisoxazol-5-yl)-2-methoxy-6-(3-methoxyphenyl)-1-naphthamide

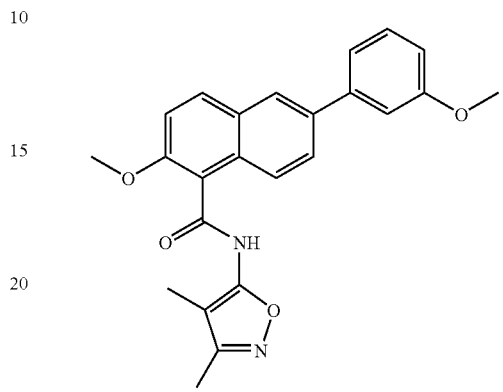

The compound was prepared by reaction of 2-methoxy-6-(3-methoxyphenyl)-1-naphthoic acid (450 mg, 1.46 mmol, 1 eq) with 2-amino-3,4-dimethylisoxazole (0.6 eq) according to method E. Purification by column chromatography with hexane/ethyl acetate 7/3 as the eluent yielded the desired product in a yield of 55%, 323 mg.

$C_{24}H_{22}O_4N_2$, MW 402, melting point: 124.5° C., $^1$H-NMR (DMSO-d$_6$): δ 10.90 (s, 1H), 8.30 (s, 1H), 8.18 (d, J=9.1 Hz, 1H), 7.95 (d, J=8.5 Hz, 1H), 7.79 (d, J=8.8 Hz, 1H), 7.60 (d, J=9.1 Hz, 1H), 7.41 (t, J=7.9 Hz, 1H), 7.32 (m, 2H), 6.98 (dd, J=2.1 Hz, J=7.6 Hz, 1H), 3.99 (s, 3H), 3.81 (s, 3H), 2.20 (s, 3H), 2.04 (s, 3H); MS (ESI): 403 (M+H)$^+$

82.) 2-Methoxy-6-(3-methoxyphenyl)-N-(5-methyl-1,3,4-thiadiazol-2-yl)-1-naphthamide

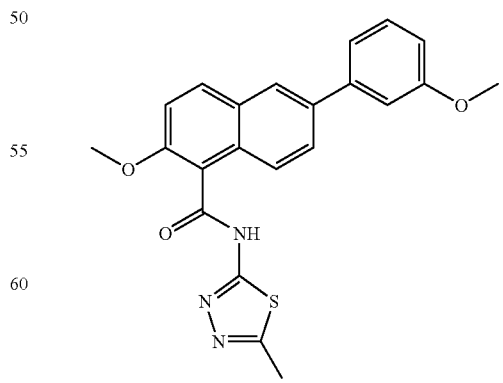

The compound was prepared by reaction of 2-methoxy-6-(3-methoxyphenyl)-1-naphthoic acid (450 mg, 1.46 mmol, 1 eq) with 2-amino-5-methyl-1,3,4-thiadiazole (0.6 eq) according to method E. Characterization of the compound was not effected. The raw product was directly employed for ether cleavage.

$C_{22}H_{19}O_3N_3S$, MW 405

83.) 2-Methoxy-6-(3-methoxyphenyl)-N-(pyridin-3-yl)-1-naphthamide

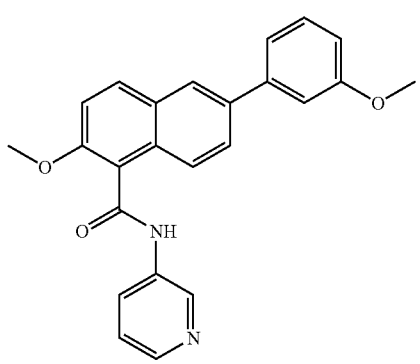

The compound was prepared by reaction of 2-methoxy-6-(3-methoxyphenyl)-1-naphthoic acid (450 mg, 1.46 mmol, 1 eq) with 2-aminopyridine (0.6 eq) according to method E. Purification by column chromatography with hexane/ethyl acetate 7/3 as the eluent yielded the desired product in a yield of 48%, 269 mg.

$C_{24}H_{20}O_3N_2$, MW 384, melting point: 154.5° C.; $^1$H NMR (Acetone-$d_6$): δ 8.55 (d, J=8.1 Hz, 1H), 8.14 (d, J=8.8 Hz, 1H), 7.99 (m, 3H), 7.76 (m, 2H), 7.39 (t, J=7.8 Hz, 1H), 7.29 (m, 2H), 7.22 (m, 1H), 6.99 (m, 1H), 6.93 (dd, J=2.5 Hz, J=8.1 Hz, 1H), 4.72 (bs, 1H), 3.96 (s, 3H), 3.89 (s, 3H); MS (ESI): 385 (M+H)$^+$

84.) 2-Methoxy-6-(methoxyphenyl)-N-(pyrimidin-2-yl)-1-naphthamide

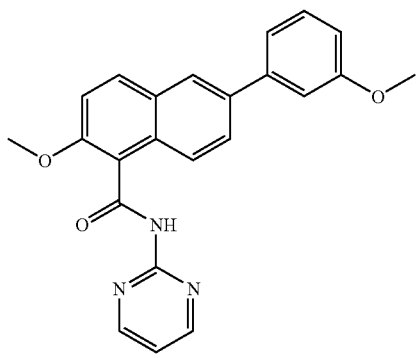

The compound was prepared by reaction of 2-methoxy-6-(3-methoxyphenyl)-1-naphthoic acid (450 mg, 1.46 mmol, 1 eq) with 2-aminopyrimidine (0.6 eq) according to method E. Characterization of the compound was not effected. The raw product was directly employed for ether cleavage.

$C_{23}H_{19}O_3N_3$, MW 385

85.) 3-(2-Methoxy-6-(3-methoxyphenyl)naphthalene-1-yl)-N-(methylsulfonyl)-benzamide

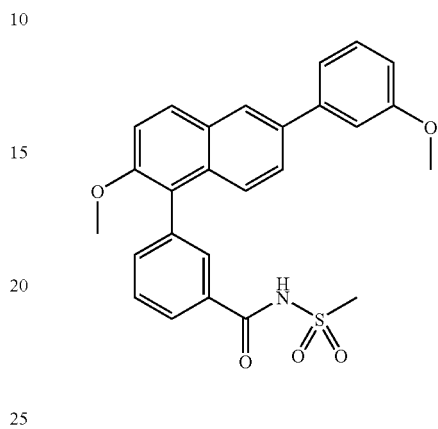

1-(3-Iodophenyl)-2-methoxy-6-(3-methoxyphenyl)naphthalene (150 mg, 0.32 mmol, 1 eq), Mo(C0)$_6$ (85 mg, 0.32 mmol, 1 eq), Pd(OAc)$_2$ (7.2 mg, 0.03 mmol, 0.01 eq), DBU (145 μl, 0.96 mmol, 3 eq), methylsulfonamide (91.7 mg, 0.96 mmol, 3 eq) and 1,4-dioxane (1 ml) are charged into a reaction vessel. The reaction is performed in a microwave oven at 110° C. for 15 min. After cooling, the reaction mixture is dissolved in dichloromethane, and purification by column chromatography with dichloromethane and 2% methanol as eluents was performed. The compound was obtained in quantitative yield.

$^1$H-NMR (CD$_3$OD+3 drops of CDCl$_3$): δ 8.05 (m, 1H), 8.02-7.98 (m, 2H), 7.96 (bs, 1H), 7.63-7.60 (m, 3H), 7.46-7.43 (m, 2H), 7.40-7.36 (m, 1H), 7.29-7.28 (m, 1H), 7.23-7.22 (m, 1H), 6.93-6.91 (m, 1H), 3.89 (s, 3H), 3.85 (s, 3H), 3.05 (s, 3H); $^{13}$C-NMR (CD$_3$OD+3 drops of CDCl$_3$): δ 160.4, 154.2, 142.7, 136.5, 131.3, 130.4, 130.2, 129.6, 126.5, 126.1, 125.6, 120.0, 114.3, 113.2, 112.9, 56.8, 55.5, 41.4; IR (neat): 3328, 3254, 2935, 1693 1/cm Ether Cleavage:

Method F:

The corresponding methoxy compound (1 eq) is dissolved in 15 ml of toluene, and aluminum chloride (5 eq) is added. The mixture is boiled under reflux for 2 hours under a nitrogen atmosphere, and after cooling, 2% Na$_2$CO$_3$ is added. The hydrophilic and lipophilic phases are separated, and the water phase is extracted with ethyl acetate. The combined organic phases are dried over magnesium sulfate. After filtering and removing the solvent in vacuum, purification is effected by column chromatography.

Method G:

A solution of the corresponding methoxy compound in dichloromethane under a nitrogen atmosphere is cooled at −78° C. Boron tribromide solution (1 M in dichloromethane) is slowly added dropwise, and the mixture is stirred at −78° C. for 1 h and at RT over night. Addition of water is followed by extraction with ethyl acetate. The combined organic phases are washed with a saturated sodium chloride solution, dried over magnesium sulfate, filtered and concentrated in vacuum on a rotary evaporator.

86.) 2-(3-Hydroxyphenyl)-1H-indol-5-ol (1)

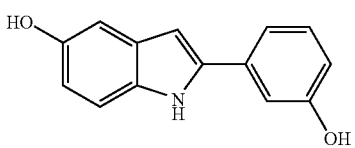 [SMILES: Oc1cccc(-c2cc3cc(O)ccc3[nH]2)c1]

The compound is prepared by reaction of 5-methoxy-2-(3-methoxyphenyl)-1H-indole (89 mg, 0.35 mmol, 1 eq) with boron tribromide (2.1 ml, 2.1 mmol, 6 eq) according to method G. Purification by preparative thin-layer chromatography with hexane/ethyl acetate 4/6 yields the desired product in a yield of 76%, 60 mg.

$C_{14}H_{11}NO_2$; MW 225; $^1$H-NMR (CD$_3$OD): δ 7.24-7.19 (m, 4H), 6.92 (d, J=2.3 Hz, 1H), 6.72 (dt, J=2.4 Hz, J=6.5 Hz, 1H), 6.68 (dd, J=2.4 Hz, J=8.7 Hz, 1H), 6.60 (s, 1H); $^{13}$C-NMR (CD$_3$OD): δ 159.2, 152.0, 140.4, 136.0, 134.1, 131.5, 131.1, 117.8, 115.5, 113.2, 113.0, 112.8, 105.5, 99.4; IR: 3432 (indole), 3289 (OH), 1596, 1486, 1453, 1198 1/cm; MS (ESI): 226 (M+H)$^+$

87.) 2-(3-Hydroxyphenyl)quinolin-6-ol (12)

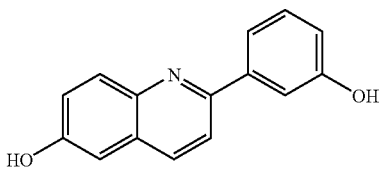

The compound is prepared by reaction of 6-methoxy-2-(3-methoxyphenyl)quinoline (77 mg, 0.29 mmol, 1 eq) with boron tribromide (15 eq) according to method G. Purification by column chromatography with hexane/ethyl acetate 7/3 as the eluent yields the desired product in a yield of 10%, 7 mg.

$C_{15}H_{11}NO_2$, MW 237; $^1$H-NMR (CD$_3$OD): δ 7.20 (ddd, J=1.3 Hz, J=2.5 Hz, J=8.2 Hz, 1H); 7.46 (t, J=2.2 Hz, 1H); 7.52 (ddd, J=1.3 Hz, J=1.9 Hz, J=7.9 Hz, 1H); 7.54 (d, J=2.5 Hz, 1H); 7.57 (t, J=7.9 Hz, 1H); 7.75 (dd, J=2.5 Hz, J=9.1 Hz, 1H); 8.22 (d, J=8.8 Hz, 1H); 8.27 (d, J=9.5 Hz, 1H); 8.95 (d, J=8.8 Hz, 1H); $^{13}$C-NMR (CD$_3$OD): δ 155.3, 154.9, 153.0, 141.3, 138.2, 133.6, 127.6, 127.5, 125.9, 120.2, 117.5, 116.5, 114.1, 111.7, 102.7; IR: 3182, 1625, 1589, 1487 1/cm; MS (ESI): 238 (M+H)$^+$

88.) 3-(Quinolin-3-yl)phenol (13)

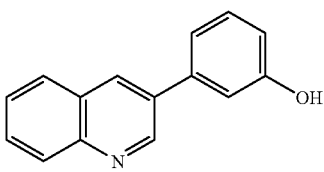 [SMILES: Oc1cccc(-c2cnc3ccccc3c2)c1]

The compound is prepared by reaction of 3-(3-methoxyphenyl)quinoline (101 mg, 0.43 mmol, 1 eq) with aluminum trichloride (341 mg, 2.57 mmol, 6 eq) according to method F. Purification by preparative thin-layer chromatography with dichloromethane/methanol 95/5 (DC plates coated with 1 mm thick coating) yields the desired product in a yield of 85%, 81 mg.

$C_{15}H_{11}NO_2$, MW 221; $^1$H-NMR (CDCl$_3$+3 drops of CD$_3$OD): δ 9.06 (d, J=2.1 Hz, 1H), 8.22 (d, J=1.8 Hz, 1H), 8.03 (d, J=8.5 Hz, 1H), 7.78 (d, J=7.9 Hz, 1H), 7.64 (t, J=8.5 Hz, 1H), 7.50 (t, J=7.0 Hz, 1H), 7.27 (t, J=7.9 Hz, 1H), 7.15 (m, 1H), 7.12 (d, J=7.6 Hz, 1H), 6.87 (dd, J=2.4 Hz, J=8.2 Hz, 1H), 2.49 (bs, 1H); $^{13}$C-NMR (CDCl$_3$+3 drops of CD$_3$OD): δ 157.7, 149.4, 146.6, 138.8, 134.0, 133.8, 130.4, 129.7, 128.3, 128.2, 128.1, 127.2, 118.7, 115.5, 114.3; IR: 3057, 1590, 1494, 1447, 1303, 1250 1/cm; MS (ESI): 222 (M+H)$^+$

89.) 4-(Quinolin-3-yl)phenol (14)

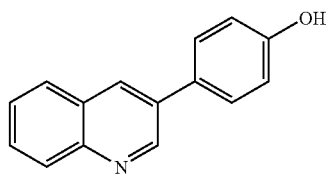 [SMILES: Oc1ccc(-c2cnc3ccccc3c2)cc1]

The compound is prepared by reaction of 3-(4-methoxyphenyl)quinoline with aluminum trichloride (564 mg, 4.23 mmol, 5 eq) according to method F. Purification by column chromatography with dichloromethane/methanol 99/1 as the eluent yields the desired product in a yield of 82%, 156 mg.

$C_{15}H_{11}NO$; MW 221; $^1$H-NMR (CDCl$_3$): δ 9.04 (d, J=2.5 Hz, 1H), 8.19 (d, J=2.2 Hz, 1H), 8.03 (d, J=8.5 Hz, 1H), 7.81 (d, J=7.9 Hz, 1H), 7.52 (d, J=8.8 Hz, 3H); 7.63 (t, 1H), 6.92 (d, J=8.5 Hz, 2H); $^{13}$C-NMR (CDCl$_3$): δ 149.6, 133.8, 133.7, 132.5, 132.4, 129.2, 128.7, 128.6, 127.9, 116.1; IR: 2946, 1608, 1518, 1494, 1449, 1271 1/cm; MS (ESI): 222 (M+H)$^+$

90.) 3-(4-Hydroxyphenyl)quinolin-7-ol (15)

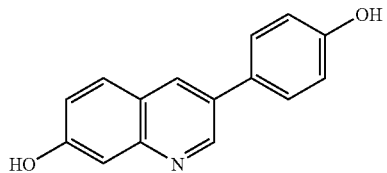 [SMILES: Oc1ccc(-c2cnc3cc(O)ccc3c2)cc1]

The compound is prepared by reaction of 7-methoxy-3-(4-methoxyphenyl)quinoline (96 mg, 0.37 mmol, 1 eq) with aluminum trichloride (392 mg, 2.95 mmol, 6 eq) according to method F. Purification by column chromatography with dichloromethane/methanol 96/4 as the eluent yields the desired product in a yield of 63%, 55 mg.

$C_{15}H_{11}NO_2$; MW 237; $^1$H-NMR (CDCl$_3$): δ 8.91 (d, J=2.2 Hz, 1H), 8.30 (d, J=1.9 Hz, 1H), 7.80 (d, J=8.3 Hz, 1H), 7.56 (d, J=8.3 Hz, 2H), 7.29 (d, J=1.9 Hz, 1H), 7.19 (dd, J=2.5 Hz, J=9.1 Hz, 1H), 6.93 (d, J=8.3 Hz, 2H); $^{13}$C-NMR (CDCl$_3$): 158.8, 157.3, 148.6, 147.5, 132.8, 131.3, 129.1, 128.7, 127.8, 122.9, 119.7, 115.7, 108.3; IR: 3277, 1613, 1580, 1518, 1260 1/cm; MS (ESI): 238 (M+H)$^+$

91.) 3-(3-Hydroxyphenyl)quinolin-7-ol (16)

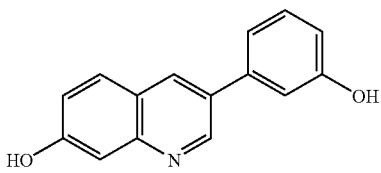 [SMILES: Oc1cccc(-c2cnc3cc(O)ccc3c2)c1]

The compound is prepared by reaction of 7-methoxy-3-(3-methoxyphenyl)-quinoline (108 mg, 0.40 mmol, 1 eq) with aluminum trichloride (433 mg, 3.26 mmol, 8 eq) according to method F. Purification by column chromatography with dichloromethane/methanol 95/5 as the eluent yields the desired product in a yield of 76%, 73 mg.

$C_{15}H_{11}NO_2$; MW 237; $^1$H-NMR (CD$_3$OD): δ 8.82 (d, J=2.5 Hz, 1H), 8.24 (d, J=2.2 Hz, 1H), 7.73 (d, J=8.8 Hz, 1H), 7.20 (m, 2H), 7.10 (dd, J=2.2 Hz, J=8.8 Hz, 1H), 7.07 (d, J=8.8 Hz, 1H), 7.03 (t, J=1.9 Hz, 1H), 6.74 (d, J=8.2 Hz, 1H); $^{13}$C-NMR (CD$_3$OD): δ 160.7, 159.3, 150.1, 149.6, 140.3, 135.1, 132.7, 131.3, 130.8, 124.2, 121.2, 119.3, 116.0, 114.8, 109.8; IR: 3057, 1599, 1586, 1499, 1454, 1266 1/cm; MS (ESI): 238 (M+H)$^+$

92.) 5-(6-Hydroxynaphthalene-2-yl)pyridin-3-ol (17)

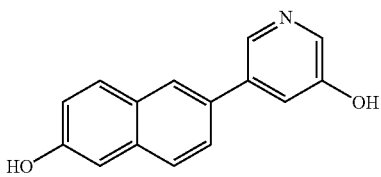 [SMILES: Oc1cncc(-c2ccc3cc(O)ccc3c2)c1]

The compound is prepared by reaction of 3-methoxy-5-(6-methoxynaphthalene-2-yl)pyridine (200 mg, 0.75 mmol, 1 eq) with aluminum trichloride (803 mg, 6.04 mmol, 8 eq) according to method F. Purification by column chromatography with dichloromethane/methanol 95/5 as the eluent yields the desired product in a yield of 7%, 13 mg.

$C_{15}H_{11}NO_2$; MW 237; $^1$H-NMR (d-acetone): δ 8.50 (d, J=1.9 Hz, 1H), 8.21 (d, J=2.5 Hz, 1H), 8.10 (d, J=2.5 Hz, 1H), 7.90 (d, J=9.1 Hz, 1H), 7.82 (d, J=8.5 Hz, 1H), 7.72 (dd, J=1.9 Hz, J=8.8 Hz, 1H), 7.55-7.54 (m, 1H), 7.26 (d, J=2.2 Hz, 1H), 7.21 (dd, J=2.5 Hz, J=8.8 Hz, 1H); IR: 3359, 1586, 1444, 1268 1/cm; MS (ESI): 238 (M+H)$^+$

93.) 6-(2-Hydroxyphenyl)-2-naphthol (18)

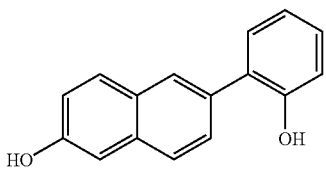 [SMILES: Oc1ccc2cc(-c3ccccc3O)ccc2c1]

The compound is prepared by reaction of 2-methoxy-6-(2-methoxyphenyl)-naphthalene (150 mg, 0.57 mmol, 1 eq) with boron tribromide (8.5 ml, 8.5 mmol, 15 eq) according to method G. Purification by column chromatography with hexane/ethyl acetate as the eluent yields the desired product in a yield of 7%, 9 mg.

$C_{16}H_{12}O_2$; MW 236; $^1$H-NMR (CD$_3$OD): δ 7.93 (s, 1H), 7.77 (d, J=8.8 Hz, 1H), 7.70-7.65 (m, 2H), 7.38-7.36 (m, 1H), 7.21-7.16 (m, 2H), 7.11 (dd, J=2.5 Hz, J=8.8 Hz, 1H), 6.96 (dd, J=0.9 Hz, J=7.0 Hz, 1H), 6.95 (dd, J=0.9 Hz, J=7.9 Hz, 1H); $^{13}$C-NMR (CD$_3$OD): δ 156.3, 155.5, 135.3, 134.9, 131.3, 130.7, 130.1, 129.3, 128.7, 126.6, 121.0, 119.3, 117.0, 109.7; IR: 3490, 3368, 1611, 1496, 1446 1/cm; MS (ESI): 237 (M+H)$^+$

94.) 6-(3-Hydroxyphenyl)-2-naphthol (19)

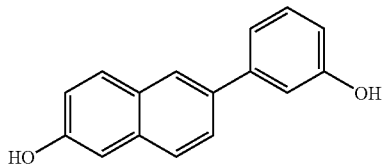 [SMILES: Oc1cccc(-c2ccc3cc(O)ccc3c2)c1]

The compound is prepared by reaction of 2-methoxy-6-(3-methoxyphenyl)-naphthalene (51 mg, 0.19 mmol, 1 eq) with boron tribromide (0.6 ml, 0.60 mmol, 3 eq) according to method G. Purification by column chromatography with dichloromethane/methanol 98/2 as the eluent yields the desired product in a yield of 52%, 23 mg.

$C_{16}H_{12}O_2$; MW 236; $^1$H-NMR (CDCl$_3$+3 drops of CD$_3$OD): δ 7.88 (d, J=1.5 Hz, 1H), 7.71 (d, J=9.1 Hz, 1H), 7.66 (d, J=9.1 Hz, 1H), 7.60 (dd, J=1.6 Hz, J=8.5 Hz, 1H), 7.27 (d, J=7.8 Hz, 1H), 7.16 (ddd, J=0.9 Hz, J=1.6 Hz, J=7.6 Hz, 1H), 7.11 (m, 2H), 7.08 (dd, J=2.2 Hz, J=8.5 Hz, 1H), 6.78 (ddd, J=0.9 Hz, J=2.5 Hz, J=7.8 Hz, 1H); $^{13}$C-NMR (CDCl$_3$+3 drops of CD$_3$OD): δ 142.8, 135.7, 129.9, 126.7, 125.9, 125.6, 118.9; IR: 3198, 1606, 1592, 1573, 1498, 1449, 1366, 1284, 1149, 1083 1/cm; MS (ESI): 237 (M+H)$^+$

95.) 6-(4-Hydroxyphenyl)-2-naphthol (20)

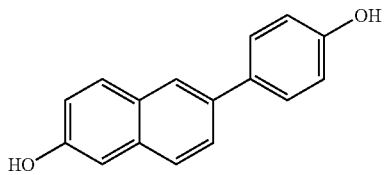 [SMILES: Oc1ccc(-c2ccc3cc(O)ccc3c2)cc1]

The compound is prepared by reaction of 2-methoxy-6-(4-methoxyphenyl)-naphthalene (150 mg, 0.57 mmol, 1 eq) with boron tribromide (3.4 ml, 3.4 mmol, 3 eq) according to method G. Purification by column chromatography with hexane/ethyl acetate 9/1 as the eluent yields the desired product in a yield of 98%, 132 mg.

$C_{16}H_{12}O_2$; MW 236; $^1$H-NMR: (CD$_3$OD): δ 7.91 (d, J=1.3 Hz, 1H), 7.85 (d, J=8.8 Hz, 1H); 7.75 (m, 2H), 7.65 (m, 2H), 7.21 (d, J=2.5 Hz, 1H), 7.17 (dd, J=8.8 Hz, J=2.5 Hz, 1H), 6.98 (m, 2H); $^{13}$C-NMR: (CD$_3$OD): δ 130.6, 130.0, 129.1, 129.0, 127.7, 127.6, 126.9, 126.5, 125.8, 125.4, 119.5, 119.4, 116.7, 116.6, 109.7; IR: 3358, 2930, 1604, 1512, 1248, 1178, 836 1/cm; MS (ESI): 235 (M−H)$^−$

96.) 6-(4-Hydroxyphenyl)-1-naphthol (21)

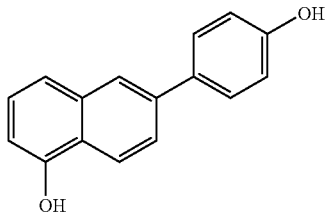 [SMILES: Oc1ccc(-c2ccc3c(O)cccc3c2)cc1]

The compound is prepared by reaction of 6-(4-methoxyphenyl)-1-naphthol (57 mg, 0.23 mol, 1 eq) with boron tribromide (2.3 ml, 2.28 mmol, 10 eq) according to method G. Purification by column chromatography with dichloromethane/2% methanol as the eluent yields the desired product in a yield of 30%, 16 mg.

$C_{16}H_{12}O_2$; MW 236; $^1$H-NMR (CD$_3$OD): δ 8.22 (d, J=8.8 Hz, 1H), 7.91 (d, J=1.9 Hz, 1H), 7.66 (dd, J=1.8 Hz, J=8.5 Hz, 1H), 7.62-7.57 (m, 2H), 7.37 (d, J=8.5 Hz, 1H), 7.28 (t, J=7.5 Hz, 1H), 6.91 (m, 2H), 6.80 (dd, J=0.9 Hz, J=7.2 Hz, 1H), $^{13}$C-NMR (CD$_3$OD): δ 156.8, 153.1, 138.5, 135.3, 132.4, 128.1, 127.9, 126.2, 123.8, 123.7, 123.4, 122.3, 118.9, 118.2, 115.5, 115.3, 107.3; IR: 3354, 2925, 1598, 1519, 1234 1/cm; MS (ESI): 237 (M+H)$^+$

97.) 6-(3-Nitrophenyl)-naphthalene-2-ol (22)

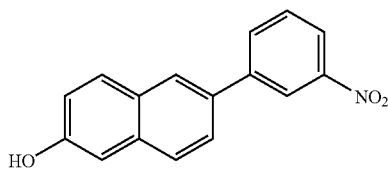 [SMILES: O=[N+]([O-])c1cccc(-c2ccc3cc(O)ccc3c2)c1]

The compound is prepared by reaction of 6-methoxy-6-(3-nitrophenyl)-naphthalene (200 mg, 0.72 mmol, 1 eq) with boron tribromide (5.6 eq) according to method G. Purification by column chromatography with hexane/ethyl acetate 9/1 as the eluent yields the desired product in a yield of 47%, 90 mg.

$C_{16}H_{11}NO_3$; MW 265; $^1$H-NMR (CD$_3$OD): δ 8.55-8.54 (m, 1H), 8.20 (ddd, J=1.3 Hz, J=2.5 Hz, J=8.2 Hz, 1H), 8.11 (ddd, J=1.3 Hz, J=1.9 Hz, J=7.9 Hz, 1H), 8.07 (d, J=1.6 Hz, 1H), 7.84 (d, J=8.5 Hz, 1H), 7.78 (d, J=8.5 Hz, 1H), 7.73-7.68 (m, 2H), 7.18-7.14 (m, 2H); $^{13}$C-NMR (CD$_3$OD): δ 157.1, 150.0, 144.1, 136.0, 134.0, 133.8, 130.9, 129.7, 128.1, 126.8, 125.8, 122.3, 122.1, 119.9, 109.5; IR: 3466, 1526, 1362 1/cm; MS (ESI): 264 (M−H)$^−$ 98.) 6-(3-Aminophenyl)-naphthalen-2-ol (23)

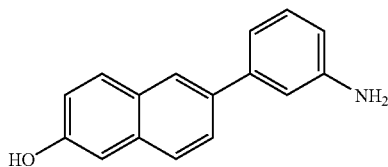

The compound is prepared by reaction of 3-(6-methoxynaphthalene-2-yl)phenylamine (87.9 mg, 0.35 mmol, 1 eq) with boron tribromide (5 eq) according to method G. Purification by column chromatography with hexane/ethyl acetate 9/1 as the eluent yields the desired product in a yield of 14%, 12 mg.

$C_{16}H_{13}NO$; MW 235; $^1$H-NMR (CD$_3$OD): δ 7.96 (d, J=1.3 Hz, 1H), 7.80 (d, J=8.8 Hz, 1H), 7.72 (d, J=8.8 Hz, 1H), 7.68-7.66 (m, 1H), 7.23 (t, J=7.9 Hz, 1H), 7.15 (d, J=2.5 Hz, 1H), 7.13-7.11 (m, 2H), 7.08 (ddd, J=0.9 Hz, J=1.6 Hz, J=7.6 Hz, 1H), 6.75 (ddd, J=0.9 Hz, J=2.2 Hz, J=7.9 Hz, 1H); $^{13}$C-NMR (CD$_3$OD): δ 156.5, 143.5, 130.7, 130.5, 127.6, 126.7, 126.2, 119.6, 118.1, 115.4, 115.2, 109.7; IR: 3369, 2926 1/cm; MS (ESI): 236 (M+H)$^+$ 99.) 6-(3-Hydroxyphenyl)-1-naphthol (24)

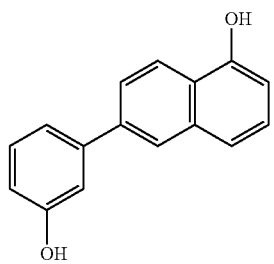 [SMILES: Oc1cccc(-c2ccc3c(O)cccc3c2)c1]

6-(3-Hydroxyphenyl)-3,4-dihydronaphthalene-1(2H)-one (503 mg, 2.11 mmol, 1 eq) and Pd/C (505 mg) are suspended in p-cymene (15 ml). The reaction mixture is refluxed for 6 h, cooled, filtered over Celite and extracted with 1 M NaOH. The aqueous phase is acidified with 1 M HCl and extracted with ether. The combined organic phases are washed with water, dried over magnesium sulfate, filtered and concentrated in vacuum on a rotary evaporator. Purification by column chromatography with dichloromethane/ethyl acetate 9/1 as the eluent yields the desired product in a yield of 16%, 83 mg.

$C_{16}H_{12}O_2$; MW 236; $^1$H-NMR (CD$_3$OD): δ 8.26 (d, J=8.8 Hz, 1H); 7.96 (s, 1H); 7.67 (dd, J=1.8 Hz, J=8.8 Hz, 1H); 7.39 (d, J=8.2 Hz, 1H); 7.29 (t, J=8.2 Hz, 2H); 7.21 (m, 2H); 6.84-6.81 (m, 2H); $^{13}$C-NMR (CD$_3$OD): δ 159.0, 154.5, 144.0, 140.0, 136.6, 130.9, 127.7, 126.2, 125.6, 125.0, 123.8, 120.4, 119.6, 115.3, 115.1, 109.1; IR: 3365, 2953, 2921, 2853, 1599, 1577, 1458, 1277 1/cm; MS (ESI): 237 (M+H)$^+$

100.) 6-(4-Methoxyphenyl)-1-naphthol (25)

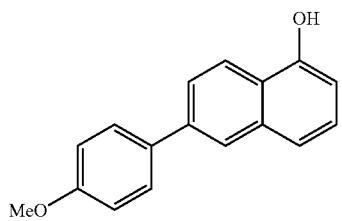 [SMILES: COc1ccc(-c2ccc3c(O)cccc3c2)cc1]

6-(4-Methoxyphenyl)-3,4-dihydronaphthalene-1(2H)-one (510 mg, 2.02 mmol, 1 eq) and Pd/C (528 mg) are suspended in p-cymene (7 ml). The reaction mixture is refluxed for 24 h, cooled, filtered over Celite and extracted with 1 M NaOH.

The aqueous phase is acidified with 1 M HCl and extracted with ether. The combined organic phases are washed with water, dried over magnesium sulfate, filtered and concentrated in vacuum on a rotary evaporator. Purification by column chromatography with dichloromethane/hexane 5/5 as the eluent yields the desired product in a yield of 14%, 69 mg.

$C_{17}H_{14}O_2$; MW 250; $^1$H-NMR (CD$_3$OD): δ 8.24 (d, J=8.8 Hz, 1H); 7.95 (d, J=1.6 Hz, 1H); 7.72-7.69 (m, 3H); 7.38 (d, J=8.5 Hz, 1H); 7.29 (t, J=7.6 Hz, 1H); 7.05 (m, 2H); 6.80 (dd, J=7.6 Hz, J=0.95 Hz, 1H); 3.87 (s, 3H), $^{13}$C-NMR (Aceton-d$_6$): δ 160.4, 139.1, 136.4, 134.1, 129.1, 127.6, 125.2, 124.7, 123.7, 120.3, 115.2, 108.8, 55.6; IR: 3388, 3034, 2959, 2931, 2837, 1581, 1510, 1282, 1236, 1183, 1030 1/cm, MS (ESI): 251 (M+H)$^+$

101.) 6-(3-Hydroxy-5-methylphenyl)-2-naphthol (26)

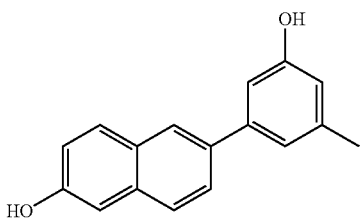 [SMILES: Cc1cc(O)cc(-c2ccc3cc(O)ccc3c2)c1]

The compound is prepared by reaction of 2-methoxy-6-(3-methoxy-5-methylphenyl)naphthalene (26 mg, 0.10 mmol, 1 eq) with boron tribromide solution (1 ml, 1 mmol, 10 eq) according to method G. After the processing, the analytically pure compound was obtained (quantitative yield, 25 mg).

$C_{17}H_{14}O_2$; MW 250; $^1$H-NMR (CDCl$_3$+3 drops of CD$_3$OD): δ 7.84 (d, J=1.6 Hz, 1H), 7.67 (d, J=8.8 Hz, 1H), 7.61 (d, J=8.5 Hz, 1H), 7.56 (dd, J=1.9 Hz, J=8.5 Hz, 1H), 7.07 (d, J=2.2 Hz, 1H), 7.04 (dd, J=2.5 Hz, J=8.8 Hz, 1H), 6.95-6.94 (m, 1H), 6.89-6.88 (m, 1H), 6.58-6.57 (m, 1H), 2.29 (s, 3H); $^{13}$C-NMR (CDCl$_3$+3 drops of CD$_3$OD): δ 156.8, 154.6, 142.5, 139.7, 135.7, 129.7, 128.5, 126.5, 125.8, 125.4, 119.6, 118.4, 114.6, 111.1, 108.8, 61.2; IR: 3253, 2959, 1594, 1493, 1214, 1154 1/cm; MS (ESI): 249 (M−H)$^−$

102.) 5-(6-Hydroxy-2-naphthyl)-1,1'-biphenyl-3,4'-diol (27)

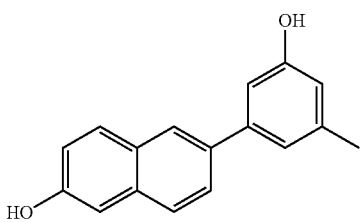 [SMILES: Cc1cc(O)cc(-c2ccc3cc(O)ccc3c2)c1]

The compound is prepared by reaction of 2-(4',5-dimethoxy-1,1'-biphenyl-3-yl)-6-methoxynaphthalene (40 mg, 0.11 mmol, 1 eq) with boron tribromide solution (1.35 ml, 1.35 mmol, 12 eq) according to method G. After the addition of water, the desired product was obtained as a precipitate in a yield of 92%, 34 mg.

$C_{22}H_{16}O_3$; MW 328; $^1$H-NMR (CD$_3$OD): δ 8.02 (s, 1H), 7.82 (d, J=8.8 Hz, 1H), 7.72-7.73 (m, 2H), 7.53-7.55 (m, 2H), 7.38 (t, J=1.5 Hz, 1H), 7.17 (d, J=1.5 Hz, 1H), 7.13 (dd; J=1.5 Hz, J=8.8 Hz, 1H), 7.10 (d, J=1.5 Hz, 1H), 6.90-6.92 (m, 2H), 7.00 (m, 1H); $^{13}$C-NMR (CD$_3$OD): δ 159.2, 158.3, 156.7, 144.4, 137.1; 135.8, 134.0, 130.9, 130.1, 129.2, 127.8, 126.8, 126.5, 119.7, 117.9, 116.6, 113.2, 113.1, 109.8; IR: 3313, 2975, 1599, 1178, 830 1/cm; MS (APCI): 329 (M+H)$^+$

103.) 6-[3-Hydroxy-5-(6-hydroxy-2-naphthyl)phenyl]-2-naphthol (28)

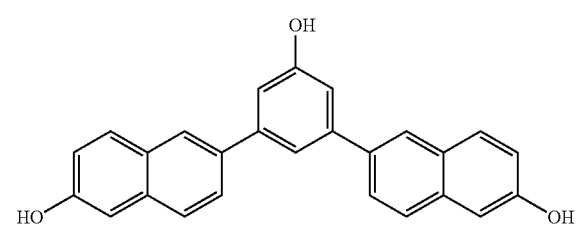 [SMILES: Oc1cc(-c2ccc3cc(O)ccc3c2)cc(-c2ccc3cc(O)ccc3c2)c1]

The compound is prepared by reaction of 2-methoxy-6-[3-methoxy-5-(6-methoxy-2-naphthyl)phenyl]naphthalene (100 mg, 0.24 mmol, 1 eq) with boron tribromide solution (3.6 ml, 3.6 mmol, 15 eq) according to method G. Purification by column chromatography with hexane/ethyl acetate 9/1 yielded the desired product in a yield of 99%, 90 mg.

$C_{26}H_{18}O_3$; MW: 378; $^1$H-NMR (CD$_3$OD): δ 8.06 (s, 2H), 7.84 (d, J=8.5 Hz, 2H), 7.15-7.18 (m, 6H), 7.55 (s, 1H), 7.77 (s, 4H), $^{13}$C-NMR (CD$_3$OD): δ 159.4, 156.7, 144.6, 136.7, 135.8, 130.9, 130.1, 127.8, 126.8, 126.5, 119.8, 118.4, 113.6, 109.8; IR: 3390, 1596, 1180 1/cm; MS (ES): 379 (M+H)$^+$

104.) 3-Hydroxy-5-(6-hydroxynaphthalen-2-yl)-N-methylbenzamide (29)

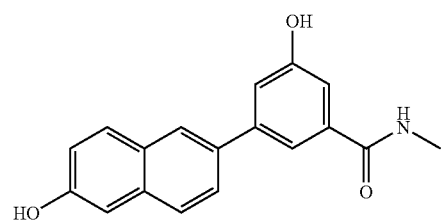

The compound is prepared by reaction of 3-methoxy-5-(6-methoxynaphthalene-2-yl)-N-methylbenzamide (110 mg, 0.34 mmol, 1 eq) with boron tribromide solution (5 eq) according to method G. Purification by column chromatography was not necessary. The desired product was already obtained after the processing in quantitative yield (99.6 mg).

$C_{18}H_{15}NO_3$; MW 293; $^1$H-NMR (CD$_3$OD): δ 8.03 (bs, 1H), 7.82 (d, J=8.8 Hz, 1H), 7.76 (d, J=8.8 Hz, 1H), 7.71 (dd, J=1.6 Hz, J=8.5 Hz, 1H), 7.66-7.65 (m, 1H), 7.33-7.32 (m, 1H), 7.26-7.24 (m, 1H), 7.17 (d, J=2.2 Hz, 1H), 7.14 (dd, J=2.5 Hz, J=8.8 Hz, 1H), 2.98 (s, 3H); $^{13}$C-NMR (CD$_3$OD): δ 173.0, 170.9, 159.3, 156.9, 144.4, 137.5, 136.0, 130.9, 130.0, 127.9, 126.6, 126.4, 119.8, 117.9, 117.8, 113.8, 109.7, 26.9; IR: 3392, 3156, 2927, 1632, 1587, 1551, 1292, 1192 1/cm; MS (ESI): 292 (M–H)⁻

105.) 3-Hydroxy-5-(6-hydroxynaphthalene-2-yl)-N-phenylbenzamide (30)

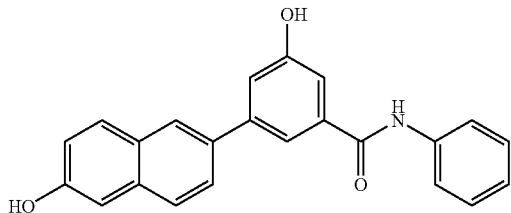 [SMILES: O=C(Nc1ccccc1)c1cc(O)cc(-c2ccc3cc(O)ccc3c2)c1]

The compound is prepared by reaction of 3-methoxy-5-(6-methoxynaphthalene-2-yl)-N-phenylbenzamide (300 mg, 0.78 mmol, 1 eq) with boron tribromide solution (5 eq) according to method G. Purification by column chromatography with hexane/dichloromethane 1/99 yielded the desired product in a yield of 11%, 32 mg.

$C_{23}H_{17}NO_3$; MW 355; ¹H-NMR (acetone-$d_6$): δ 8.10 (bs, 1H), 7.89-7.87 (s, 1H), 9.48 (m, 3H), 7.82 (bs, 1H), 7.79 (d, J=8.5 Hz, 1H), 7.75 (dd, J=1.9 Hz, J=8.5 Hz, 1H), 7.46 (bs, 1H), 7.42 (bs. 1H), 7.38-7.34 (m, 2H), 7.25 (d, J=2.2 Hz, 1H), 7.20 (dd, J=2.2 Hz, J=8.8 Hz, 1H), 7.13-7.10 (m, 1H); ¹³C-NMR (acetone-$d_6$): δ 170.9, 159.0, 156.6, 143.6, 135.5, 135.4, 130.8, 129.5, 127.7, 126.5, 126.3, 124.5, 120.9, 119.8, 117.9, 117.6, 114.1, 109.6; IR: 3275, 1653, 1591, 1530, 1497, 1441, 1331 1/cm; MS (ESI): 356 (M+H)⁺

106.) (E)-3-[3-Hydroxy-5-(6-hydroxynaphthalene-2-yl)phenyl]-N-methylacrylamide (31)

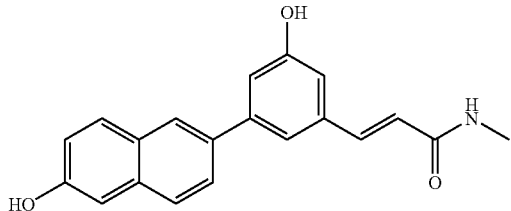 [SMILES: CNC(=O)/C=C/c1cc(O)cc(-c2ccc3cc(O)ccc3c2)c1]

The compound is prepared by reaction of (E)-3-[3-methoxy-5-(6-methoxy-naphthalene-2-yl)phenyl]-N-methylacrylamide (200 mg, 0.58 mmol, 1 eq) with boron tribromide solution (5 eq) according to method G. Purification by preparative thin-layer chromatography with dichloromethane/methanol 90/10 yielded the desired product in a yield of 13%, 25 mg.

$C_{20}H_{17}NO_3$; MW 319; ¹H-NMR (CD₃OD): δ 8.00 (m, 1H), 7.83 (d, J=8.5 Hz, 1H), 7.76 (d, J=8.2 Hz, 1H), 7.69 (dd, J=1.6 Hz, J=8.5 Hz, 1H), 7.58 (d, J=15.8 Hz, 1H), 7.41 (m, 1H), 7.19 (m, 1H), 7.17 (m, 1H), 7.14 (dd, J=2.2 Hz, J=8.5 Hz, 1H), 7.01 (m, 1H), 6.66 (d, J=15.8 Hz, 1H), 2.90 (s, 3H); ¹³C-NMR (CD₃OD): δ 169.3, 159.9, 141.7, 136.3, 135.9, 133.6, 132.4, 130.9, 130.0, 129.9, 127.8, 126.5, 121.9, 119.8, 119.3, 116.5, 113.7, 109.7, 24.0; IR: 3296, 1580, 1289, 1212, 1184 1/cm; MS (ESI): 320 (M+H)⁺

107.) (E)-3-[3-Hydroxy-5-(6-hydroxynaphthalene-2-yl)phenyl]-N-phenylacrylamide (32)

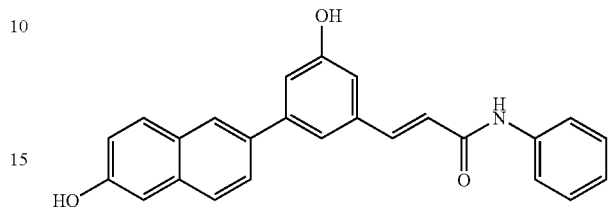

The compound is prepared by reaction of (E)-3-[3-methoxy-5-(6-methoxy-naphthalene-2-yl)phenyl]-N-phenylacrylamide (126 mg, 0.31 mmol, 1 eq) with boron tribromide solution (5 eq) according to method G. Purification by preparative thin-layer chromatography with dichloromethane/methanol 98/2 yielded the desired product in a yield of 14%, 17 mg.

$C_{25}H_{19}NO_3$; MW 381; ¹H-NMR (CD₃OD): δ 8.03 (d, J=1.3 Hz, 1H), 7.84 (d, J=8.5 Hz, 1H), 7.81 (d, J=8.5 Hz, 1H), 7.74-7.71 (m, 4H), 7.47 (m, 1H), 7.40-7.37 (m, 2H), 7.23-7.22 (m, 1H), 7.18-7.14 (m, 3H), 7.07 (m, 1H), 6.89 (d, J=15.4 Hz, 1H); ¹³C-NMR (CD₃OD): δ 183.1, 135.9, 130.9, 129.9, 127.9, 126.5, 121.2, 119.8, 119.5, 116.7, 109.7; IR: 3478, 1594, 1440 1/cm; MS (ESI): 382 (M+H)⁺

108.) 3-[3-Hydroxy-5-(6-hydroxynaphthalene-2-yl)phenyl]-N-methylpropionamide (33)

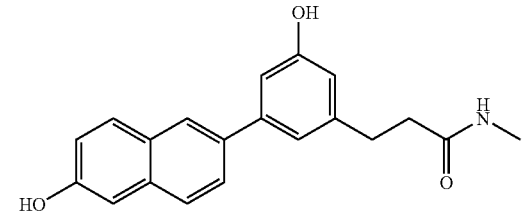 [SMILES: CNC(=O)CCc1cc(O)cc(-c2ccc3cc(O)ccc3c2)c1]

The compound is prepared by reaction of 3-[3-methoxy-5-(6-methoxy-naphthalene-2-yl)phenyl]-N-methylpropionamide (47.8 mg, 0.16 mmol, 1 eq) with aluminum trichloride (213.3 mg, 1.60 mmol, 10 eq) according to method F. Purification by preparative thin-layer chromatography with dichloromethane/methanol 98/2 yielded the desired product in a yield of 35%, 16 mg.

$C_{20}H_{19}NO_3$; MW 321; ¹H-NMR (CD₃OD): δ 7.96 (bs, 1H), 7.80 (d, J=8.8 Hz, 1H), 7.72 (d, J=8.5 Hz, 1H), 7.66 (dd, J=1.5 Hz, J=8.5 Hz, 1H), 7.16 (d, J=2.1 Hz, 1H), 7.13 (dd, J=2.4 Hz, J=8.8 Hz, 1H), 7.09 (m, 1H), 7.00 (t, J=1.8 Hz, 1H), 6.68 (m, 1H), 2.97-2.94 (m, 2H), 2.74 (s, 3H), 2.66-2.53 (m, 2H); ¹³C-NMR (CD₃OD): δ 175.9, 159.0, 156.6, 144.2, 144.1, 136.9, 130.8, 127.7, 126.7, 126.3, 119.7, 119.5, 115.0, 112.8, 109.7, 99.9, 38.9, 33.1, 26.3; IR: 3416, 1721, 1618, 1593 1/cm; MS (ESI): 322 (M+H)+

109.) 3-[3-Hydroxy-5-(6-hydroxynaphthalene-2-yl)phenyl]-N-phenylpropionamide (34)

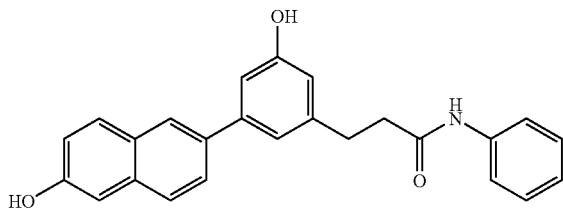 [SMILES: O=C(CCc1cc(O)cc(-c2ccc3cc(O)ccc3c2)c1)Nc1ccccc1]

The compound is prepared by reaction of 3-[3-methoxy-5-(6-methoxy-naphthalene-2-yl)phenyl]-N-phenylpropionamide (55 mg, 0.13 mmol, 1 eq) with aluminum trichloride (291.3 mg, 2.19 mmol, 12 eq) according to method F. Purification by preparative thin-layer chromatography with hexane/ethyl acetate 1/1 yielded the desired product in a yield of 23%, 17 mg.

$C_{25}H_{21}NO_3$; MW 383; $^1$H-NMR (CD$_3$OD): δ 7.91 (m, 1H), 7.74 (d, J=8.5 Hz, 1H), 7.70 (d, J=8.5 Hz, 1H), 7.64 (dd, J=1.8 Hz, J=8.5 Hz, 1H), 7.57-7.56 (m, 2H), 7.34-7.31 (m, 2H), 7.14-7.10 (m, 4H), 7.01-7.00 (m, 1H), 6.74 (m, 1H), 3.08-3.05 (m, 2H), 2.76-2.73 (m, 2H); IR: 3351, 1728, 1596, 1444, 1244 1/cm

110.) N-[2-Hydroxy-4-(6-hydroxy-2-naphthyl)phenyl]acetamide (35)

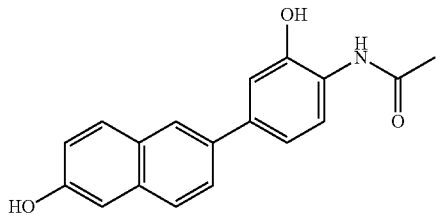 [SMILES: CC(=O)Nc1ccc(-c2ccc3cc(O)ccc3c2)cc1O]

The compound is prepared by reaction of N-[2-methoxy-4-(6-methoxy-2-naphthyl)phenyl]acetamide (54 mg, 0.17 mol, 1 eq) with boron tribromide solution (2.52 ml, 2.52 mmol, 15 eq) according to method G. Purification by preparative thin-layer chromatography with dichloromethane/methanol 95/5 yielded the desired product in a yield of 45%, 22 mg.

$C_{18}H_{15}NO_3$; MW 293; $^1$H-NMR (CD$_3$OD): δ 7.93 (s, 1H), 7.77 (d, J=8.8 Hz, 1H), 7.71 (m, 2H), 7.64 (dd, J=1.9 Hz, J=8.8 Hz, 1H), 7.24 (d, J=1.9 Hz, 1H), 7.19 (dd, J=1.9 Hz, J=8.2 Hz, 1H), 7.13 (m, 1H), 7.10 (dd, J=2.5 Hz, J=8.3 Hz, 1H), 2.22 (s, 3H); IR: 3267 (hydroxy), 1630.1604, 1524, 1505 1/cm; MS (ESI): 294 (M+H)+

111.) N-[2-Hydroxy-4-(6-hydroxy-2-naphthyl)phenyl]benzamide (36)

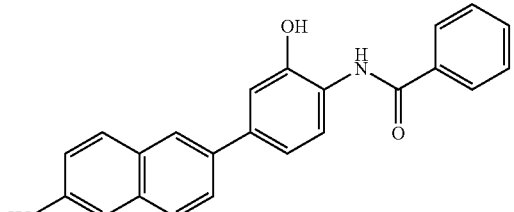

The compound is prepared by reaction of N-[2-methoxy-4-(6-methoxy-2-naphthyl)phenyl]benzamide (49 mg. 0.13 mol, 1 eq) with boron tribromide solution (2.25 ml, 2.25 mmol, 15 eq) according to method G. Purification by preparative thin-layer chromatography with dichloromethane/methanol 95/5 as the eluent yielded the desired product in quantitative yield.

$C_{22}H_{17}NO_3$; MW 355; $^1$H-NMR (CD$_3$OD): δ 8.00-7.96 (m, 4H), 7.79 (d, J=8.8 Hz, 1H), 7.72 (d, J=8.8 Hz, 1H), 7.68 (dd, J=1.6 Hz, J=8.5 Hz, 1H), 7.64-7.61 (m, 1H), 7.58-7.55 (m, 2H), 7.31 (d, J=1.9 Hz, 1H), 7.27 (dd, J=1.9 Hz, J=8.2 Hz, 1H), 7.14 (d, J=2.5 Hz, 1H), 7.11 (dd, J=2.5 Hz, J=8.8 Hz, 1H); $^{13}$C-NMR (CD$_3$OD): δ 168.7, 157.0, 150.5, 140.7, 136.6, 136.1, 136.0, 133.4, 131.1, 130.4, 130.1, 128.8, 128.1, 126.7, 126.6, 126.4, 124.5, 120.1, 119.7, 115.6, 110.1; IR: 3384, 3076, 1675, 1599, 1524, 1495 1/cm; MS (ESI): 356 (M+H)+

112.) 3-Hydroxy-7-(3-hydroxyphenyl)-N-methyl-2-naphthamide (37)

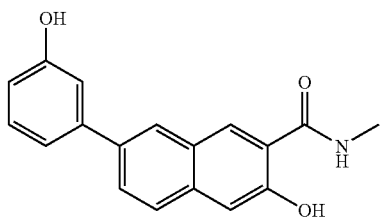 [SMILES: CNC(=O)c1cc2cc(-c3cccc(O)c3)ccc2cc1O]

The compound is prepared by reaction of 3-methoxy-7-(3-methoxyphenyl)-N-methyl-2-naphthamide (93 mg, 0.29 mol, 1 eq) with boron tribromide solution (5.5 ml, 5.5 mmol, 19 eq) according to method G. Purification was not necessary. The desired product was obtained in quantitative yield.

$C_{18}H_{15}NO_3$; MW 293; $^1$H-NMR (CD$_3$OD): δ 8.43 (s, 1H), 8.03 (s, 1H), 7.75 (s, 2H), 7.29 (t, J=7.9 Hz, 1H), 7.26 (s, 1H), 7.19 (d, J=7.6 Hz, 1H), 7.15 (s, 1H), 6.80 (dd, J=2.2 Hz, J=7.9, 1H), 3.02 (s, 3H); $^{13}$C-NMR (CD$_3$OD): δ 159.2, 156.9, 137.4, 131.2, 131.1, 129.1, 127.6, 127.5, 120.4, 119.4, 115.4, 114.9, 112.0; IR: 3327, 2927, 1647, 1599, 1578, 1465 1/cm; MS (ESI): 294 (M+H)$^+$

113.) 3-Hydroxy-7-(3-hydroxyphenyl)-N-phenyl-2-naphthamide (38)

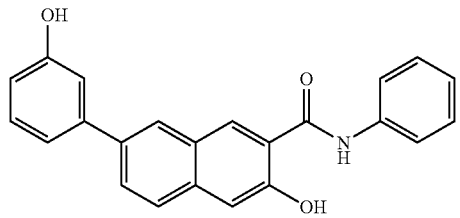 [SMILES: O=C(Nc1ccccc1)c1cc2cc(-c3cccc(O)c3)ccc2cc1O]

The compound is prepared by reaction of 3-methoxy-7-(3-methoxyphenyl)-N-phenyl-2-naphthamide (86 mg, 0.22 mol, 1 eq) with boron tribromide solution (4.45 ml, 4.45 mmol, 20 eq) according to method G. Purification by preparative thin-layer chromatography with hexane/ethyl acetate 6/4 as the eluent yielded the desired product in a yield of 50%, 39 mg.

$C_{23}H_{17}NO_3$; MW 355; $^1$H-NMR (DMSO): δ 11.54 (bs, 1H), 10.14 (bs, 1H), 8.73 (s, 1H), 8.47 (bs, 1H), 8.08 (s, 1H), 7.84-7.81 (m, 4H), 7.42 (dd, J=0.9 Hz, J=8.5 Hz, 2H), 7.36 (s, 1H), 7.31 (t, J=8.2 Hz, 1H), 7.23-7.18 (m, 3H), 6.88-6.86 (m, 1H); $^{13}$C-NMR (DMSO): δ 168.3, 158.4, 156.9, 142.4, 138.5, 136.8, 136.6, 130.4, 130.3, 129.2, 128.5, 127.7, 127.0, 126.6, 125.1, 121.6, 119.2, 118.5, 114.8, 114.1, 111.7; IR: 3371, 3136, 2957, 1694, 1623, 1567, 1499, 1445 1/cm; MS (ESI): 355 (M+H)$^+$

114.) (E)-3-(2-Hydroxy-6-(3-hydroxyphenyl)naphthalene-1-yl)-N-methylacrylamide (39)

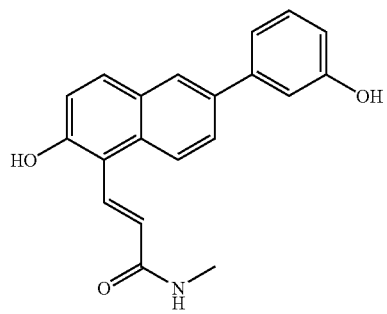 [SMILES: CNC(=O)/C=C/c1c(O)ccc2cc(-c3cccc(O)c3)ccc12]

The compound is prepared by reaction of (E)-3-(2-hydroxy-6-(3-hydroxyphenyl)naphthalene-1-yl)-N-methylacrylamide (127 mg, 0.37 mmol, 1 eq) with boron tribromide solution (2.9 ml, 2.31 mmol, 8 eq) according to method G. Purification by column chromatography with dichloromethane/methanol 95/5 as the eluent yielded the desired product in a yield of 60%, 71 mg.

$C_{20}H_{17}NO_3$; MW 319; $R_f$ value (dichloromethane/methanol 90/10): 0.5; $^1$H-NMR (CD$_3$OD): δ 8.29 (d, J=15.8 Hz, 1H), 8.27 (d, J=9.1 Hz, 1H), 7.99 (d, J=1.9 Hz, 1H), 7.81 (d, J=9.1 Hz, 1H), 7.79 (dd, J=1.9 Hz, J=8.8 Hz, 1H), 7.31 (t, J=7.91 Hz, 1H), 7.24-7.21 (m, 1H), 7.21 (d, J=8.8 Hz, 1H), 7.20-7.19 (m, 1H), 7.11 (d, J=15.8 Hz, 1H), 6.82 (ddd, J=0.9 Hz, J=2.5 Hz, J=7.9 Hz, 1H), 2.93 (s, 3H); $^{13}$C-NMR (CD$_3$OD): δ 170.8, 158.9, 156.7, 143.5, 137.0, 134.6, 134.0, 132.4, 131.0, 130.3, 127.4, 127.3, 126.0, 124.3, 119.5, 119.4, 115.3, 114.9, 26.7; IR: 3064, 1730, 1643, 1581, 1465 1/cm; MS (ESI): 320 (M+H)$^+$

115.) (E)-3-(2-Hydroxy-6-(3-hydroxyphenyl)naphthalene-1-yl)-N-phenylacrylamide (40)

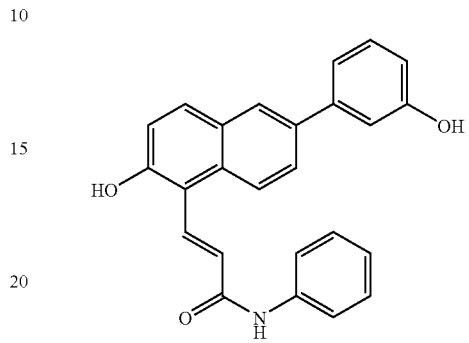

The compound is prepared by reaction of (E)-3-(2-hydroxy-6-(3-hydroxyphenyl)naphthalene-1-yl)-N-phenylacrylamide (50 mg, 0.12 mmol, 1 eq) with boron tribromide solution (0.98 mmol, 8 eq) according to method G. Purification by column chromatography with dichloromethane/methanol 95/5 as the eluent yielded the desired product in a yield of 13%, 6 mg.

$C_{25}H_{19}NO_3$; MW 381; $R_f$ value (dichloromethane/methanol 90/10): 0.6; $^1$H-NMR (CD$_3$OD): δ 8.47 (d, J=15.8 Hz, 1H), 8.34 (d, J=8.8 Hz, 1H), 8.03 (d, J=1.9 Hz, 1H), 7.86 (d, J=9.1 Hz, 1H), 7.83 (dd, J=1.9 Hz, J=8.8 Hz, 1H), 7.76 (d, J=7.6 Hz, 1H), 7.40-7.36 (m, 3H), 7.34-7.31 (m, 1H), 7.26-7.24 (m, 1H), 7.24 (d, J=9.1 Hz, 1H), 7.21-7.20 (m, 1H), 7.17-7.14 (m, 1H), 6.83 (ddd, J=0.9 Hz, J=2.5 Hz, J=7.9 Hz, 1H); IR: 3353, 1710, 1646, 1575, 1498, 1441 1/cm; MS (ESI): 382 (M+H)$^+$

116.) 2-Hydroxy-6-(3-hydroxyphenyl)-N-methyl-1-naphthamide (41)

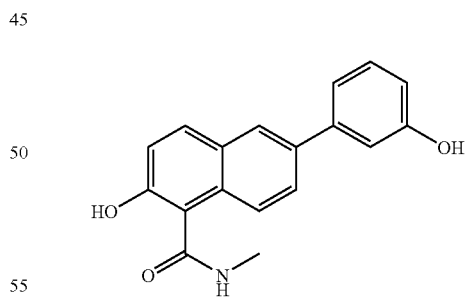

The compound is prepared by reaction of 2-methoxy-6-(3-methoxyphenyl)-N-methyl-1-naphthamide (250 mg, 0.78 mmol, 1 eq) with boron tribromide solution (3.89 mmol, 5 eq) according to method G. Purification by column chromatography with dichloromethane/methanol 98/2 as the eluent yielded the desired product in a yield of 95%, 217 mg.

$C_{18}H_{15}NO_3$; MW 293; $R_f$ value (dichloromethane/methanol 95/5): 0.4; $^1$H-NMR (CD$_3$OD): δ 8.01 (d, J=1.9 Hz, 1H), 7.90 (q, J=2.5 Hz, J=8.8 Hz, 2H), 7.76 (dd, J=1.9 Hz, J=8.8 Hz, 1H), 7.31 (t, J=7.9 Hz, 1H), 7.22 (m, 1H), 7.19 (d, J=8.8

Hz, 1H), 7.17 (m, 1H), 6.82 (ddd, J=0.6 Hz, J=2.2 Hz, J=7.9 Hz, 1H), 3.06 (s, 3H); IR: 3281, 1608, 1580, 1492 1/cm; MS (ESI): 292 (M−H)−

117.) 2-Hydroxy-6-(3-hydroxyphenyl)-N-phenyl-1-naphthamide (42)

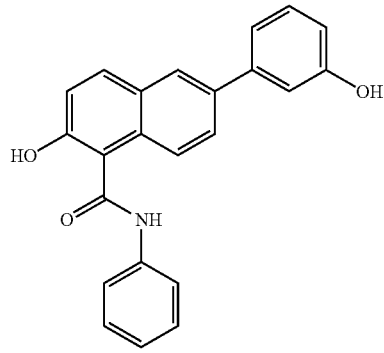 [SMILES: O=C(Nc1ccccc1)c1c(O)ccc2cc(-c3cccc(O)c3)ccc12]

The compound is prepared by reaction of 2-methoxy-6-(3-methoxyphenyl)-N-phenyl-1-naphthamide (217 mg, 0.57 mmol, 1 eq) with boron tribromide solution (3.39 mmol, 6 eq) according to method G. Purification by column chromatography with dichloromethane/methanol 95/5 as the eluent yielded the desired product in a yield of 23%, 47 mg.

$C_{23}H_{17}NO_3$; MW 355; $R_f$ value (dichloromethane/methanol 95/5): 0.4; $^1$H-NMR (CD$_3$OD): δ 7.99 (d, J=1.2 Hz, 1H), 7.93 (d, J=8.8 Hz, 1H), 7.88 (d, J=8.8 Hz, 1H), 7.77 (d, J=7.6 Hz, 2H), 7.74 (dd, J=1.8 Hz, J=8.8 Hz, 1H), 7.38 (t, J=7.9 Hz, 2H), 7.27 (m, 1H), 7.21 (d, J=8.8 Hz, 1H), 7.16 (m, 1H), 7.15 (m, 2H), 6.78 (ddd, J=0.9 Hz, J=2.4 Hz, J=7.9 Hz, 1H); IR: 3271, 1628, 1596, 1494 1/cm; MS (ESI): 356 (M+H)+

118.) 2-Hydroxy-N,6-bis(3-hydroxyphenyl)-1-naphthamide (43)

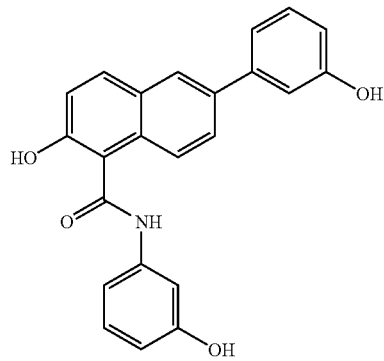 [SMILES: O=C(Nc1cccc(O)c1)c1c(O)ccc2cc(-c3cccc(O)c3)ccc12]

The compound is prepared by reaction of 2-methoxy-N,6-bis(3-methoxyphenyl)-1-naphthamide (150 mg, 0.36 mmol, 1 eq) with boron tribromide solution (2.9 ml, 2.9 mmol, 8 eq) according to method G. Purification by column chromatography with dichloromethane/methanol 93/7 as the eluent yielded the desired product in a yield of 75%, 100 mg.

$C_{23}H_{17}NO_4$; MW 371; $R_f$ value (dichloromethane/methanol 93/7): 0.4; $^1$H-NMR (CD$_3$OD): δ 8.00 (d, J=1.6 Hz, 1H), 7.92 (d, J=8.5 Hz, 1H), 7.88 (d, J=9.1 Hz, 1H), 7.75 (dd, J=1.9 Hz, J=8.8 Hz, 1H), 7.44 (t, J=1.9 Hz, 1H), 7.27 (t, J=7.9 Hz, 1H), 7.18 (m, 5H), 6.78 (m, 1H), 6.61 (m, 1H); IR: 3278, 1602, 1493 1/cm; MS (ESI): 372 (M+H)+

119.) (2-Hydroxy-6-(3-hydroxyphenyl)naphthalene-1-yl)(morpholino)methanone (44)

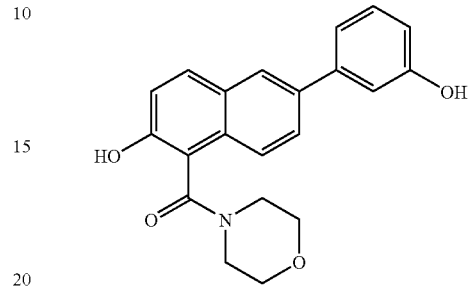

The compound is prepared by reaction of 2-methoxy-6-(3-methoxyphenyl)-naphthalene-1-yl)(morpholino)methanone (195 mg, 0.52 mmol, 1 eq) with boron tribromide solution (2.6 ml, 2.58 mmol, 5 eq) according to method G. Purification by column chromatography with dichloromethane/methanol 95/5 as the eluent yielded the desired product in a yield of 93%, 169 mg.

$C_{21}H_{19}NO_4$; MW 349; $^1$H-NMR (CD$_3$OD): δ 8.04 (d, J=1.6 Hz, 1H), 7.92 (d, J=8.8 Hz, 1H), 7.79 (dd, J=1.9 Hz, J=8.8 Hz, 1H), 7.70 (d, J=8.8 Hz, 1H), 7.33-7.30 (m, 1H), 7.23-7.21 (m, 1H), 7.21 (d, J=8.8 Hz, 1H), 7.18-7.17 (m, 1H), 6.83-6.81 (m, 1H), 3.97 (m, 2H), 3.88-3.87 (m, 2H), 3.71-3.70 (m, 1H), 3.59-3.57 (m, 1H), 3.41-3.36 (m, 1H), 3.31 (m, 1H); IR: 3216, 2923, 1595, 1575, 1273 1/cm; MS (ESI): 348 (M−H)−

120.) (2-Hydroxy-6-(3-hydroxyphenyl)naphthalene-1-yl)(piperazin-1-yl)methanone (45)

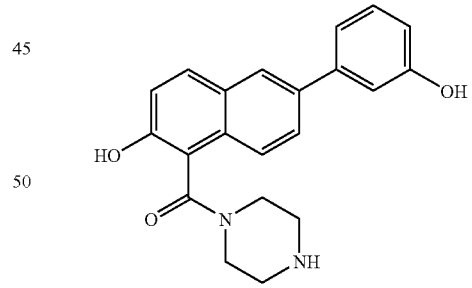

The compound is prepared by reaction of tert-butyl 4-(2-methoxy-6-(3-methoxyphenyl)-1-naphthoyl)piperazine-1-carboxylate (200 mg, 0.42 mmol, 1 eq) with boron tribromide solution (2.5 ml, 2.52 mmol, 6 eq) according to method G. Purification by column chromatography was not necessary. Extraction of the aqueous phase with ethyl acetate yields the desired product in a yield of 60%, 88 mg.

$C_{21}H_{20}N_2O_3$, MW 348; $R_f$ value (dichloromethane/methanol 85/15): 0.04; $^1$H-NMR (CD$_3$OD): δ 8.05 (d, J=1.3 Hz, 1H), 7.93 (d, J=9.1 Hz, 1H), 7.79 (dd, J=1.6, J=8.5 Hz, 1H), 7.69 (d, J=8.8 Hz, 1H), 7.31 (t, J=7.9 Hz, 1H), 7.23 (d, J=8.8 Hz, 1H), 7.21-7.20 (m, 1H), 7.17 (m, 1H), 6.84-6.82 (m, 1H), 4.38-4.35 (m, 1H), 4.08-4.05 (m, 1H), 3.68 (m, 1H), 3.59-3.58 (m, 1H), 3.48-3.47 (m, 1H), 3.42-3.41 (m, 1H), 3.40-3.31 (m, 1H), 3.20-3.19 (m 1H); $^{13}$C-NMR (CD$_3$OD): δ 187.0, 175.3, 170.0, 152.8, 148.8, 137.9, 132.8, 131.0, 128.2, 124.7, 119.4, 119.0, 114.9; IR: 3219, 1712, 1600, 1492, 1440 1/cm; MS (ESI): 349 (M+H)$^+$

121.) 2-Hydroxy-6-(3-hydroxyphenyl)-N-(thiazol-2-yl)-1-naphthamide (46)

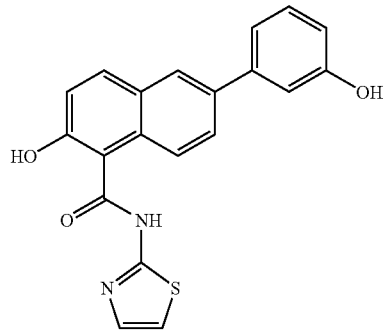 [SMILES: O=C(Nc1nccs1)c1c(O)ccc2cc(-c3cccc(O)c3)ccc12]

The compound is prepared by reaction of 2-methoxy-6-(3-methoxyphenyl)-N(thiazol-2-yl)-1-naphthamide (117 mg, 0.30 mmol, 1 eq) with boron tribromide solution (7 eq) according to method G. Purification by column chromatography with dichloromethane/methanol 95/5 as the eluent yielded the desired product.

$C_{20}H_{14}O_3N_2S$, MW 362, $^1$H-NMR (acetone-d$_6$): δ 10.79 (bs, 1H), 8.45 (d, J=8.5 Hz, 1H), 7.92 (s, 1H), 7.89 (d, J=9.1 Hz, 1H), 7.73 (d, J=7.8 Hz, 1H), 7.35 (s, 1H), 7.27 (t, J=7.5 Hz, 1H), 7.17 (m, 2H), 7.09 (m, 1H), 6.98 (bs, 1H), 6.80 (dd, J=2.5 Hz, J=7.8 Hz, 1H); IR: 3420, 3310, 3024, 2849, 1558, 1471 1/cm; MS (ESI): 361 (M−H)$^-$

122.) N-(3,4-Dimethylisoxazol-5-yl)-2-hydroxy-6-(3-hydroxyphenyl)-1-naphthamide (47)

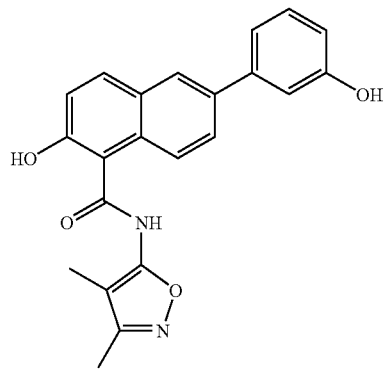 [SMILES: Cc1noc(NC(=O)c2c(O)ccc3cc(-c4cccc(O)c4)ccc23)c1C]

To a solution of the corresponding methoxy compound (130 mg, 0.32 mmol, 1 eq) in dichloromethane (15 ml), BF$_3$-thioetherate (2.52 ml, 24 mmol, 75 eq) is added, followed by stirring at RT for 24 h. Thereafter, the solvent is evaporated, and the reaction mixture is diluted with water (50 ml) and extracted with ethyl acetate (5×25 ml). The combined organic extracts are washed with water, dried over sodium sulfate, filtered and evaporated to dryness on a rotary evaporator. Purification by column chromatography with dichloromethane/methanol 95/5 as the eluent yielded the desired product in a yield of 90%, 108 mg.

$C_{22}H_{18}O_4N_2$, MW 374, melting point: 108° C.; $^1$H-NMR (acetone-d$_6$): δ 9.90 (bs, 1H), 9.81 (s, 1H), 8.48 (s, 1H), 8.20 (d, J=9.1 Hz, 1H), 8.10 (s, 1H), 8.02 (d, J=8.8 Hz. 1H), 7.85 (m, 1H), 7.30 (m, 4H), 6.89 (dd, J=2.1 Hz, J=7.6 Hz, 1H), 2.19 (s, 3H), 2.10 (s, 3H); IR: 3410 (OH), 3244 (NH), 1668, 1581 (C=O), 1494 (phenyl) cm$^{-1}$; MS (ESI): 373 (M−H)$^-$

123.) 2-Hydroxy-6-(3-hydroxyphenyl)-N-(5-methyl-1,3,4-thiadiazol-2-yl)-1-naphthamide (48)

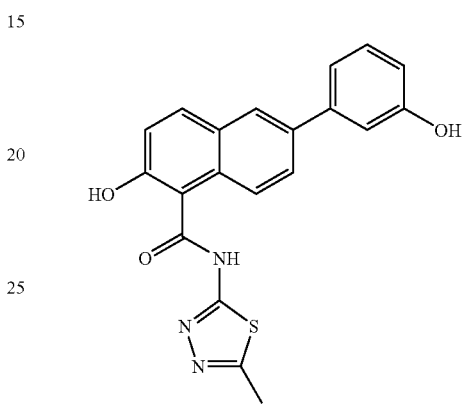

The compound is prepared by reacting the corresponding methoxy compound (117 mg, 0.30 mmol, 1 eq) with boron tribromide solution (7 eq) according to method G. Purification by column chromatography with dichloromethane/methanol 95/5 as the eluent yielded the desired product in a yield of 20%, 23 mg.

$C_{20}H_{15}O_3N_3S$, MW 377, melting point, 265.6° C.; $^1$H-NMR (acetone-d$_6$): δ 12.30 (bs, 1H), 10.03 (s, 1H), 9.07 (s, 1H), 7.66 (s, 1H), 7.55 (d, J=9.1 Hz, 1H), 7.31 (d, J=8.8 Hz, 1H), 7.23 (d, J=7.8 Hz, 1H), 6.84 (t, J=7.8 Hz, 2H), 6.74 (d, J=8.1 Hz, 1H), 6.68 (m, 1H), 6.33 (m, 1H), 2.22 (s, 3H); IR: 3430, 3210, 2910, 2800, 1652, 1545, 1491 cm$^{-1}$; MS (ESI): 378 (M+H)$^+$

124.) 2-Hydroxy-6-(3-hydroxyphenyl)-N-(pyridin-2-yl)-1-naphthamide (49)

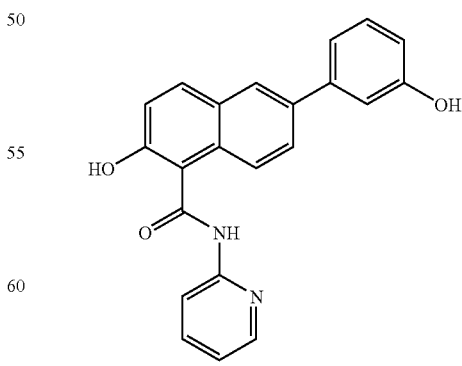

The compound is prepared by reacting the corresponding methoxy compound (117 mg, 0.30 mmol, 1 eq) with boron tribromide solution (7 eq) according to method G. Purification by column chromatography with dichloromethane/methanol 95/5 as the eluent yielded the desired product in a yield of 36%, 38 mg.

$C_{22}H_{16}O_3N_2$, MW 356, melting point: 140° C.; $^1$H-NMR (acetone-$d_6$): δ 9.79 (bs, 1H), 8.48 (d, J=6.3 Hz, 1H), 8.29 (m, 1H), 8.25 (d, J=5.0 Hz, 1H), 8.09 (m, 1H), 8.00 (d, J=8.8 Hz, 1H), 7.89 (m, 1H), 7.82 (dd, J=1.8 Hz, 6.9 Hz, 1H), 7.33 (m, 4H), 7.14 (m, 1H), 6.86 (m, 1H); IR: 3400, 3260, 2925, 2364, 1647, 1576, 1465, 1434 cm$^{-1}$; MS (ESI): 357 (M+H)$^+$

125.) 2-Hydroxy-6-(3-hydroxyphenyl)-N-(pyrimidin-2-yl)-1-naphthamide (50)

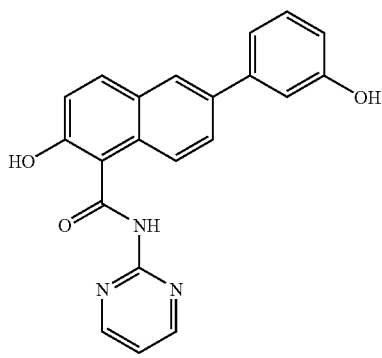 [SMILES: O=C(Nc1ncccn1)c1c(O)ccc2cc(-c3cccc(O)c3)ccc12]

The compound is prepared by reacting the corresponding methoxy compound (117 mg, 0.30 mmol, 1 eq) with boron tribromide solution (7 eq) according to method G. Purification by column chromatography with dichloromethane/methanol 95/5 as the eluent yielded the desired product in a yield of 56%, 60 mg.

$C_{21}H_{15}O_3N_3$; MW 357, melting point: 156° C.; $^1$H-NMR (acetone-$d_6$): δ 9.90 (bs, 1H), 9.60 (s, 1H), 8.59 (d, J=5.8 Hz, 2H), 8.40 (s, 1H), 8.13 (d, J=5.2 Hz, 1H), 8.05 (m, 1H), 7.95 (d, J=9.1 Hz, 1H), 7.75 (dd, J=1.8 Hz, J=6.9 Hz, 1H), 7.28 (t, J=8.1 Hz, 1H), 7.20 (m, 3H), 7.11 (t, J=5.0 Hz, 1H), 6.80 (m, 1H); IR: 3415, 3200, 1696, 1578, 1495, 1435 cm$^{-1}$; MS (ESI): 358 (M+H)$^+$

126.) 1-Bromo-6-(3-hydroxyphenyl)naphthalene-2-ol (52)

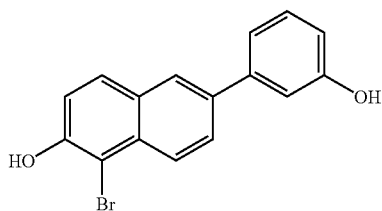 [SMILES: Oc1cccc(-c2ccc3c(Br)c(O)ccc3c2)c1]

The compound is prepared by reaction of 1-bromo-2-methoxy-6-(3-methoxyphenyl)naphthalene (500 mg, 1.46 mmol, 1 eq) with boron tribromide solution (7.3 ml, 7.3 mmol, 5 eq) according to method G. Purification of the raw product was not necessary. The desired product was obtained in quantitative yield (460 mg).

$C_{16}H_{11}BrO_2$; MW 314/316; $^1$H-NMR (CD$_3$OD): δ 8.19 (d, J=8.8 Hz, 1H), 8.02 (d, J=1.9 Hz, 1H), 7.83 (dd, J=0.9 Hz, J=8.5 Hz, 1H), 7.83 (d, J=8.8 Hz, 1H), 7.32 (t, J=7.9 Hz, 1H), 7.24 (d, J=8.8 Hz, 1H), 7.25-7.23 (m, 1H), 7.19 (m, 1H), 6.83 (ddd, J=1.3 Hz, J=2.5 Hz, J=8.2 Hz, 1H); $^{13}$C-NMR (CD$_3$OD): 156.1, 145.8, 140.2, 136.3, 133.5, 132.8, 130.4, 129.5, 129.2, 121.9, 117.8, 117.4, 112.4; IR: 3222, 1595, 1583, 1448, 1207, 1187 1/cm; MS (ESI): 313/315 (M–H)$^-$

127.) 7-Hydroxy-3-(3-hydroxyphenyl)-1-naphthonitrile (53)

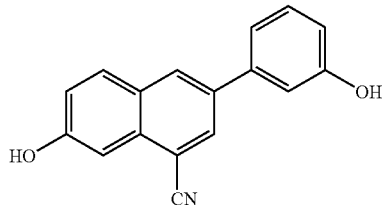 [SMILES: N#Cc1cc(-c2cccc(O)c2)cc2ccc(O)cc12]

7-Methoxy-3-(3-methoxyphenyl)-1-naphthonitrile (110 mg, 0.39 mmol, 1 eq) and pyridinium hydrochloride (4.76 mmol, 12.2 eq) are boiled under reflux for 3 h. After cooling the reaction mixture, it is acidified with 1 N HCl, the resulting precipitate is filtered and dissolved in a small amount of ethyl acetate. The organic phase is washed with water, dried over magnesium sulfate, filtered and concentrated in vacuum on a rotary evaporator. The residue formed is the desired product (yield 62%, 63 mg).

$C_{17}H_{11}NO_2$; MW 261; $R_f$ value (hexane/ethyl acetate 7/3): 0.31; $^1$H-NMR (CD$_3$OD): δ 8.30 (bs, 1H), 8.18 (d, J=1.9 Hz, 1H), 7.98 (d, J=8.8 Hz, 1H), 7.47-7.46 (m, 1H), 7.36-7.33 (m, 1H), 7.28 (dd, J=2.2 Hz, J=8.8 Hz, 1H), 7.24-7.22 (m, 1H), 7.17-7.16 (m, 1H), 6.87-6.85 (m, 1H); IR: 3274, 2239, 1599, 1588 1/cm; MS (ESI): 260 (M–H)$^-$

128.) 3-Hydroxy-7-(3-hydroxyphenyl)-1-naphthonitrile (54)

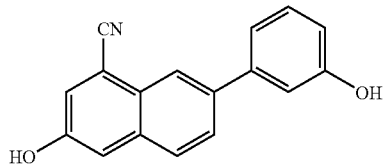 [SMILES: N#Cc1cc(O)cc2ccc(-c3cccc(O)c3)cc12]

3-Methoxy-7-(3-methoxyphenyl)-1-naphthonitrile (100 mg, 0.35 mmol, 1 eq) and pyridinium hydrochloride (492 mg, 4.3 mmol, 12.2 eq) are boiled under reflux for 3 h. After cooling the reaction mixture, it is acidified with 1 N HCl, the resulting precipitate is filtered and dissolved in a small amount of ethyl acetate. The organic phase is washed with water, dried over magnesium sulfate, filtered and concentrated in vacuum on a rotary evaporator. The residue formed is the desired product (yield 64%, 58 mg).

$C_{17}H_{11}NO_2$; MW 261; $R_f$ value (hexane/ethyl acetate 7/3): 0.21; $^1$H-NMR (CD$_3$OD): δ 8.20 (s, 1H), 7.89 (d, J=8.5 Hz, 1H), 7.85 (dd, J=1.9 Hz, J=6.9 Hz, 1H), 7.61 (d, J=2.2 Hz, 1H), 7.50 (d, J=2.5 Hz, 1H), 7.35 (dd, J=2.2 Hz, J=7.6 Hz, 1H), 7.24 (m, 1H), 7.20 (dd, J=2.2 Hz, J=1.9 Hz, 1H), 6.87 (m, 1H); IR: 3413, 3293, 3204, 2362.2240, 791, 781, 702 1/cm; MS (ESI): 260 (M−H)⁻

129.) 3-(2-Hydroxy-6-(3-hydroxyphenyl)naphthalene-1-yl)-N-methylpropanamide (55)

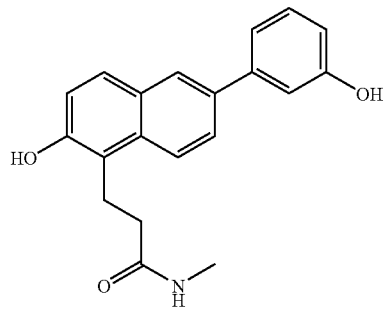 [SMILES: CNC(=O)CCc1c(O)ccc2cc(-c3cccc(O)c3)ccc12]

(E)-3-(2-Hydroxy-6-(3-hydroxyphenyl)naphthalene-1-yl)-N-methylacrylamide is stirred over night with Pd(OH)₂ in ethanol/THF 2/1 (1.5 ml) under a hydrogen atmosphere at RT. The reaction mixture is filtered, and the solvent is removed in vacuum on a rotary evaporator. The desired product was obtained in quantitative yield.

C₂₀H₁₉NO₃; MW 321; $R_f$ value (dichloromethane/methanol 90/10): 0.6; ¹H-NMR (CD₃OD): δ 8.04 (d, J=8.8 Hz, 1H), 7.98 (d, J=2.2 Hz, 1H), 7.76 (dd, J=1.9 Hz, J=8.8 Hz, 1H), 7.72 (d, J=8.8 Hz, 1H), 7.31 (t, J=7.91 Hz, 1H), 7.23-7.22 (m, 1H), 7.18 (m, 1H), 7.16 (d, J=8.8 Hz, 1H), 6.80 (ddd, J=0.9 Hz, J=2.5 Hz, J=7.9 Hz, 1H), 3.41-3.38 (m, 2H), 2.74 (s, 3H), 2.60-2.57 (m, 2H); IR: 3272, 2951, 1611, 1494, 1278 1/cm; MS (ESI): 322 (M+H)⁺

130.) 1-(3-Aminophenyl)-6-(3-hydroxyphenyl)naphthalene-2-ol (68)

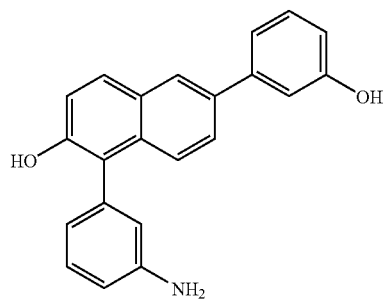 [SMILES: Nc1cccc(-c2c(O)ccc3cc(-c4cccc(O)c4)ccc23)c1]

The compound is prepared by the reaction of 3-(2-methoxy-6-(3-methoxyphenyl)naphthalene-1-yl)benzeneamine (1 g, 2.82 mmol, 1 eq) with boron tribromide solution (14.1 ml, 14.1 mmol, 5 eq) according to method G. Purification by column chromatography was not necessary, and the desired product was obtained in quantitative yield (922 mg) after processing.

C₂₂H₁₇NO₂; MW 327; $R_f$ value (dichloromethane/methanol 95/5): 0.5; ¹H-NMR (CD₃OD): δ 8.00 (d, J=1.6 Hz, 1H), 7.82 (d, J=8.8 Hz, 1H), 7.58 (dd, J=1.9 Hz, J=8.8 Hz, 1H), 7.54 (d, J=8.8 Hz, 1H), 7.32-7.29 (m, 1H), 7.29 (t, J=7.9 Hz, 1H), 7.23 (d, J=9.1 Hz, 1H), 7.22-7.20 (m, 1H), 7.17-7.16 (m, 1H), 6.87-6.85 (m, 1H), 6.81-6.79 (m, 2H), 6.75-6.73 (m, 1H); ¹³C-NMR (CD₃OD): 158.9, 152.4, 148.9, 143.9, 136.6, 134.6, 130.8, 130.2, 130.0, 126.5, 126.4, 126.3, 123.5, 122.1, 119.5, 119.4, 119.3, 115.7, 115.0, 114.8; IR: 3387, 3282 1/cm; MS (ESI): 326 (M−H)⁻

131.) 3-(2-Hydroxy-6-(3-hydroxyphenyl)naphthalene-1-yl)-N-(thiazol-2-yl)-benzenesulfonamide (69)

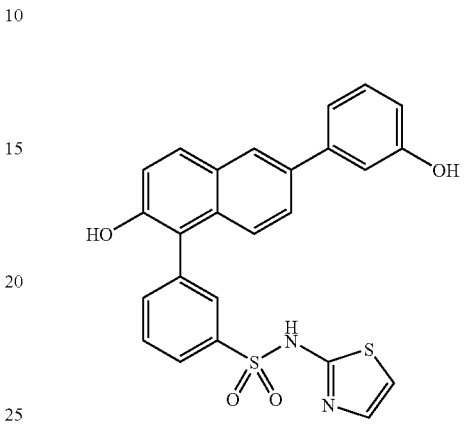

The compound is prepared by the reaction of 3-(2-methoxy-6-(3-methoxyphenyl)naphthalene-1-yl)-N-(thiazol-2-yl)benzenesulfonamide (75.3 mg, 0.15 mmol, 1 eq) with boron tribromide solution (14.1 ml, 14.1 mmol, 5 eq) according to method G. Purification by preparative thin-layer chromatography with dichloromethane/methanol 92.5/7.5 as the eluent yielded the desired compound in a yield of 27%, 19 mg.

C₂₅H₁₈N₂O₄S₂; MW 474; ¹H-NMR (CD₃OD): δ 7.90 (d, J=1.6 Hz, 1H), 7.86-7.84 (m, 1H), 7.82 (m, 1H), 7.75 (d, J=8.8 Hz, 1H), 7.55 (t, J=7.6, 1H), 7.51-7.50 (m, 1H), 7.45 (dd, J=1.9 Hz, J=8.8 Hz), 7.25 (d, J=9.1 Hz, 1H), 7.16 (t, J=7.9, 1H), 7.13 (d, J=8.8 Hz, 1H), 7.08-7.07 (m, 1H), 7.03-7.02 (m, 1H), 7.01 (d, J=4.4 Hz, 1H), 6.68-6.66 (m, 1H), 6.62 (d, J=4.7 Hz, 1H); IR fehlt; MS (ESI): 473 (M−H)⁻

132.) 3-(2-Hydroxy-6-(3-hydroxyphenyl)naphthalene-1-yl)-N-(5-methyl-1,3,4-thiadiazol-2-yl)benzenesulfonamide (70)

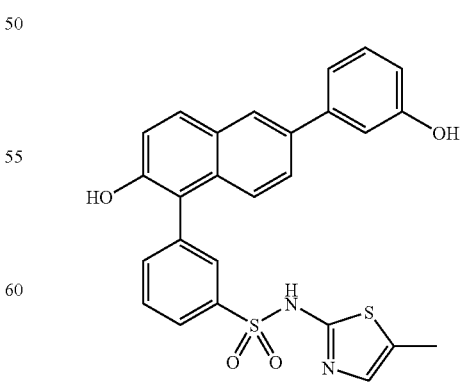

The compound is prepared by the reaction of 3-(2-methoxy-6-(3-methoxyphenyl)naphthalene-1-yl)-N-(5-methyl-1, 3,4-thiadiazole-2-yl)benzenesulfonamide (0.28 mmol, 1 eq) with boron tribromide solution (2.8 ml, 2.8 mmol, 10 eq) according to method G. Purification by column chromatography with dichloromethane/methanol 95/5 as the eluent yielded the desired compound in a yield of 47%, 64 mg.

$C_{25}H_{19}N_3O_4S_2$; MW 489; $^1$H-NMR (CD$_3$OD): δ 8.05 (d, J=1.9 Hz, 1H), 7.97-7.95 (m, 1H), 7.93-7.92 (m, 1H), 7.89 (d, J=8.8 Hz, 1H), 7.70 (t, J=7.8, 1H), 7.67-7.66 (m, 1H), 7.60 (dd, J=1.9 Hz, J=8.8 Hz), 7.40 (d, J=8.8 Hz, 1H), 7.32-7.28 (m, 1H), 7.27 (d, J=9.1 Hz, 1H), 7.22-7.21 (m, 1H), 7.17-7.16 (m, 1H), 6.81 (d, J=0.9 Hz, J=2.5 Hz, J=8.2 Hz, 1H), 2.50 (s, 3H); IR: 3317, 1541, 1274 1/cm; MS (ESI): 490 (M+H)$^+$

133.) 3-(2-Hydroxy-6-(3-hydroxyphenyl)naphthalene-1-yl)-N-(thiazol-2-yl)benzamide (71)

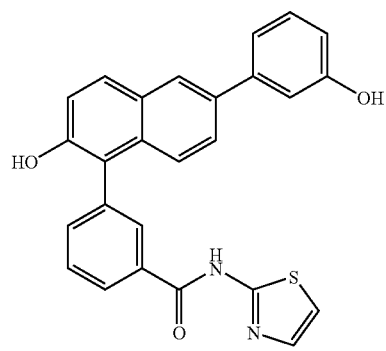 [SMILES: O=C(Nc1nccs1)c1cccc(-c2c(O)ccc3cc(-c4cccc(O)c4)ccc23)c1]

To 3-(2-hydroxy-6-(3-hydroxyphenyl)naphthalene-1-yl)benzoic acid (79 mg, 0.22 mmol, 1 eq), which is dissolved under a nitrogen atmosphere in 2 ml of dry DME, thionyl chloride (100 μl) is added, and the mixture is stirred at RT for 2 h. After the excess thionyl chloride has been removed in vacuum on a rotary evaporator, the residue is dissolved in dry DME and added dropwise to a suspension of 2-aminothiazole (22.2 mg, 0.22 mmol, 1 eq) in dry dichloromethane cooled at 0° C. The reaction mixture is stirred at RT over night, followed by removing the solvent on a rotary evaporator. Purification of the raw product by column chromatography with dichloromethane/methanol 95/5 as the eluent yielded the desired compound in a yield of 13%, 13 mg.

$C_{26}H_{18}N_2O_3S$; MW 438; R$_f$ value (hexane/ethyl acetate 1/1): 0.7; $^1$H-NMR (CD$_3$OD+3 drops of CDCl$_3$): δ 8.19 (d, J=8.8 Hz, 1H), 8.06-8.04 (m, 2H), 8.00 (d, J=1.6 Hz, 1H), 7.83-7.80 (m, 2H), 7.59-7.56 (m, 2H), 7.54-7.53 (d, J=3.5 Hz, 1H), 7.31 (t, J=7.9 Hz, 1H), 7.24 (d, J=8.8 Hz, 1H), 7.24-7.22 (m, 1H), 7.18 (t, J=2.2 Hz, 1H), 7.18 (d, J=3.5 Hz, 1H), 6.83 (ddd, J=0.9 Hz, J=2.5 Hz, J=7.9 Hz, 1H); IR: 3260, 1651, 1599, 1543, 1291 1/cm

134.) 3-(2-Hydroxy-6-(3-hydroxyphenyl)naphthalene-1-yl)-N-(5-methyl-1,3,4-thiadiazol-2-yl)benzamide (72)

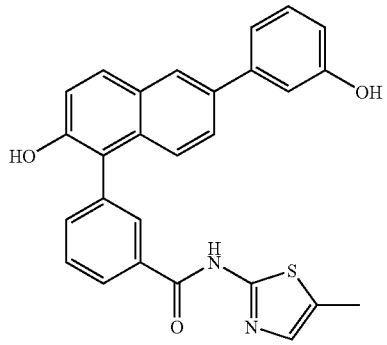 [SMILES: Cc1cnc(NC(=O)c2cccc(-c3c(O)ccc4cc(-c5cccc(O)c5)ccc34)c2)s1]

To 3-(2-hydroxy-6-(3-hydroxyphenyl)naphthalene-1-yl)benzoic acid (220 mg, 0.62 mmol, 1 eq), which is dissolved under a nitrogen atmosphere in 5 ml of dry DME, thionyl chloride (600 μl) is added, and the mixture is stirred at RT for 2 h. After the excess thionyl chloride has been removed in vacuum on a rotary evaporator, the residue is dissolved in dry THF and added dropwise to a suspension of 5-methyl-1,3,4-thiadiazole-2-amine (42.6 mg, 0.74 mmol, 1.2 eq) in dry dichloromethane cooled at 0° C. The reaction mixture is stirred at RT over night, followed by removing the solvent on a rotary evaporator. Purification of the raw product by column chromatography with dichloromethane/methanol 95/5 as the eluent yielded the desired compound in a yield of 47%, 132 mg.

$C_{26}H_{19}N_3O_3S$; MW 453; R$_f$ value (dichloromethane/methanol 90/10): 0.7; $^1$H-NMR (CDCl$_3$+3 drops of CD$_3$OD): δ 8.07-8.05 (m, 1H), 7.97-7.96 (m, 2H), 7.87 (d, J=1.9 Hz, 1H), 7.72 (dd, J=1.9 Hz, J=8.8 Hz, 1H), 7.68 (d, J=8.5 Hz, 1H), 7.55-7.54 (m, 1H), 7.48-7.45 (m, 2H), 7.16 (d, J=8.8 Hz, 1H), 7.14-7.13 (m, 1H), 7.10 (m, 1H), 6.77 (ddd, J=0.9 Hz, J=2.5 Hz, J=8.2 Hz, 1H), 2.65 (s, 3H); IR: 3406, 1541, 1247 1/cm

135.) 3-(2-Hydroxy-6-(3-hydroxyphenyl)naphthalene-1-yl)-N-(methylsulfonyl)-benzamide (90)

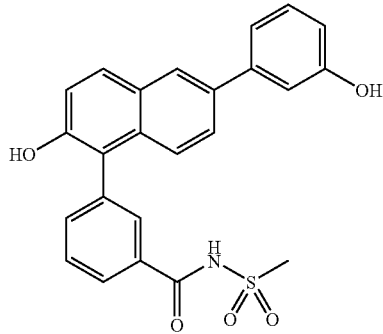 [SMILES: CS(=O)(=O)NC(=O)c1cccc(-c2c(O)ccc3cc(-c4cccc(O)c4)ccc23)c1]

The compound was prepared by refluxing 3-(2-methoxy-6-(3-methoxyphenyl)-naphthalene-1-yl)-N-(methylsulfonyl)benzamide (80 mg, 0.17 mmol, 1 eq) with pyridinium hydrochloride (302 mg, 15 eq) for two hours. After cooling, 2 ml of 1 N HCl was added, and the water phase was extracted with ethyl acetate. The organic phase was dried and concentrated in vacuum. After purification by column chromatography with 10% methanol in dichloromethane, the desired compound was obtained in 42% yield, 31 mg.

$C_{24}H_{19}NO_5S$, MW 433, $^1$H-NMR (CD$_3$OD+3 drops of CDCl$_3$): δ 8.04-8.03 (m, 1H), 7.95-7.89 (m, 2H), 7.72-7.71 (m, 1H), 7.53-7.49 (m, 2H), 7.48-7.45 (m, 1H), 7.31-7.28 (m, 1H), 7.20-7.17 (m, 1H), 7.14 (d, J=3.8, J=8.8, 1H), 7.09-7.07 (m, 1H), 7.05-7.04 (m, 1H), 6.73-6.71 (m, 1H), 1.93 (s, 3H); IR: 3265, 1705, 1382, 1275 1/cm; MS (ESI): 432 (M−H)⁻

Compounds 73-89 were all prepared according to method H.

Sulfonyl chloride (1.2 eq) dissolved in 2 ml THF is added to a solution of 1-(3-aminophenyl)-6-(3-hydroxyphenyl) naphthalene-2-ol (25 mg, 0.05 mmol, 1 eq) and 55 mg of polymer-bound morpholine in 2 ml of THF. The reaction mixtures are stirred at RT for 15 h. Thereafter, a spatula-tipful of polymer-bound DMAP is added to all reactions, and stirring at RT is continued for another night. After the night, the reactions for the preparation of compounds 75, 77, 81 were processed as follows: In order to quench excess acid chloride, a spatula-tipful of polymer-bound tris(2-aminoethyl)amine was added, and to quench the excess amine, a spatula-tipful of polymer-bound isocyanate was employed. After filtration and evaporating, these reactions were purified by means of preparative HPLC (Waters Fraktion Lynx Autopurification System, Varian Inertsil C18 column 50×21 mm, particle size 3 μm, gradient with isocratic end period, solvent: acetonitrile, water, formic acid (0.01%) 0-100%). The remaining 12 reactions were stirred over night at 60° C. and thereafter processed in the same way as the five reactions above. In these cases, the processing was effected through a Combiflash system with a gradient of hexane/ethyl acetate 2/1 to 1/1 as the eluent.

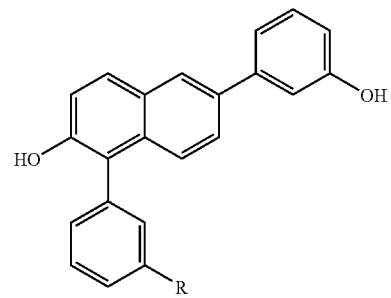

| Compound | R | MW | Area ELSD (%) | MS retention time | Yield [%] |
|---|---|---|---|---|---|
| 73 | | 518 | 100 | 5.88 | 31 |
| 74 | | 507 | 100 | 6.14 | 35 |
| 75 | | 512 | 99.54 | 5.94 | 76 |
| 76 | | 492 | 90.12 | 5.78 | 84 |

-continued
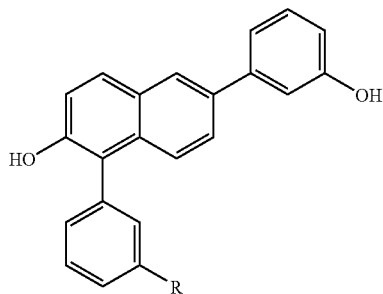
| Compound | R | MW | Area ELSD (%) | MS retention time | Yield [%] |
|---|---|---|---|---|---|
| 77 | methyl sulfonamide, 3-NO2, 4-Cl phenyl | 546 | 100 | 6.12 | 83 |
| 78 | methyl sulfonamide thiophene with 3-OMe, methyl ester | 561 | 100 | 5.90 | 19 |
| 79 | methyl sulfonamide, 4-NHAc phenyl | 524 | 99.2 | 5.43 | 32 |
| 80 | methyl sulfonamide thiophene, 2-(methylthio)pyrimidine | 597 | 100 | 6.15 | 22 |
| 81 | methyl sulfonamide, 4-NO2 phenyl | 512 | 98.93 | 5.95 | 84 |
| 82 | methyl sulfonamide, 2-OCF3, 4-Br phenyl | 629 | 100 | 6.50 | 66 |

-continued

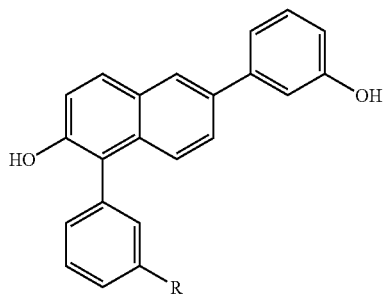

| Compound | R | MW | Area ELSD (%) | MS retention time | Yield [%] |
|---|---|---|---|---|---|
| 83 | ![R group: N-methylsulfamoyl-2-nitro-4-trifluoromethylphenyl] | 580 | 97.93 | 6.25 | 18 |
| 84 | ![R group: N-methylsulfamoyl-6-chloroimidazo[2,1-b]thiazol-5-yl] | 547 | 93.1 | 5.78 | 24 |
| 85 | ![R group: N-methylsulfamoyl-4,5-dibromothiophen-2-yl] | 628 | 95.93 | 6.42 | 21 |
| 86 | ![R group: N-methylsulfamoyl-benzothiazol-6-yl] | 524 | 100 | 5.68 | 42 |
| 87 | ![R group: N-methylsulfamoyl-thiophen-2-yl] | 473 | 100 | 5.81 | 45 |
| 88 | ![R group: N-methylsulfamoyl-4-(2-(trifluoroacetamido)ethyl)phenyl] | 606 | 100 | 5.92 | 43 |
| 89 | ![R group: N-methylsulfamoyl-4-bromo-2,5-difluorophenyl] | 581 | 99.73 | 6.23 | 32 |

136.) 2-Methoxy-6-(3-methoxyphenyl)-1-(phenyl-sulfanyl)naphthalene

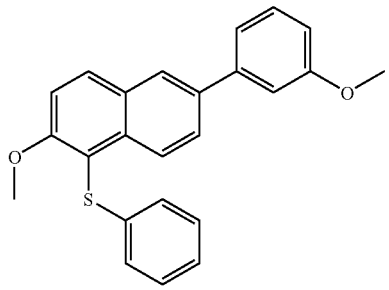 [SMILES: COc1cccc(-c2ccc3c(Sc4ccccc4)c(OC)ccc3c2)c1]

A mixture of 1-bromo-2-methoxy-6-methoxyphenylnaphthalene (850 mg, 2.47 mmol, 1 eq), sodium benzenthiolate (391 mg, 2.96 mmol, 1.2 eq) and anhydrous DMF (10 ml) was refluxed under nitrogen for 11 hours. After cooling to room temperature, the mixture was poured onto ice. The precipitate was filtered off, washed with water and dried. Yield: 385 mg, 42%.

137.) 6-(3-Hydroxyphenyl)-1-(phenylsulfanyl)-2-naphthol

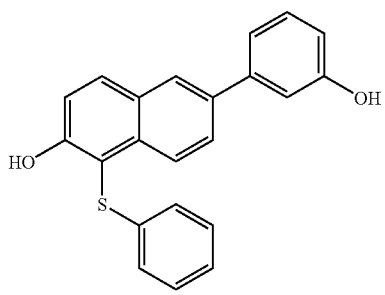 [SMILES: Oc1cccc(-c2ccc3c(Sc4ccccc4)c(O)ccc3c2)c1]

The compound was prepared by reacting 2-methoxy-6-(3-methoxyphenyl)-1-(phenylsulfanyl)naphthalene (376 mg, 1.01 mmol, 1 eq.) with boron tribromide (8 ml of a 1 M solution in cyclohexane, 8 mmol, 8 eq) according to method G. Yield: 325 mg (94%)

$C_{22}H_{16}O_2S$; MW 344; $^1$H-NMR (acetone-$d_6$): δ 8.67 (s, 1H), 8.53 (s, 1H), 8.40 (d, J=8.8 Hz, 1H), 8.23 (d, J=1.9 Hz, 1H), 8.17 (d, J=9.1 Hz, 1H), 7.88 (dd, J=1.9 Hz, J=8.8 Hz, 1H), 7.47 (d, J=9.1 Hz, 1H), 7.38 (t, J=7.2 Hz, 1H), 7.32-7.27 (m, 2H), 7.20-7.17 (m, 1H), 7.13 (m, 2H), 6.95 (m, 1H); MS (ESI): 343 (M−H)⁻

138.) 6-(3-Hydroxyphenyl)-1-(phenylsulfonyl)-2-naphthol (91)

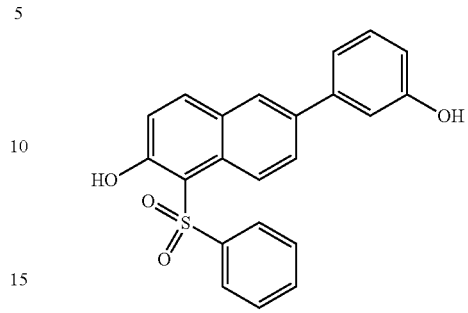

To a solution of 6-(3-hydroxyphenyl)-1-(phenylsulfanyl)-2-naphthol (71 mg, 0.21 mmol, 1 eq) in anhydrous dichloromethane (10 ml), m-CPBA (192 mg, 0.82 mmol, 3.9 eq) in dichloromethane (10 ml) was added dropwise at 0° C. The reaction mixture was stirred at first at 0° C. for one hour, then at room temperature for twelve hours, and subsequently poured into ice water. The aqueous phase was extracted with ethyl acetate. The combined organic phases were washed with sodium hydrogencarbonate solution and water and dried over $Na_2SO_4$. Purification by column chromatography ($SiO_2$; dichloromethane: methanol=95:5) yielded the analytically pure compound. Yield: 38 mg (50%).

$C_{22}H_{16}O_4S$; MW 376; $^1$H-NMR (acetone-$d_6$): δ 8.49 (d, J=9.1 Hz, 1H), 8.23 (d, J=8.8 Hz, 1H), 8.11 (s, 1H), 8.06 (d, J=7.9 Hz, 1H), 7.82 (dd, J=1.8 Hz, J=8.8 Hz, 1H), 7.70-7.62 (m, 3H), 7.27 (m, 2H), 7.16 (m, 2H), 6.85 (dt, J=1.8 Hz, J=8.8 Hz, 1H); MS (ESI): 375 (M−H)⁻

139.) 6-(3-Hydroxyphenyl)-1-(4-methylphenyl)sulfonyl)-2-naphthol (92)

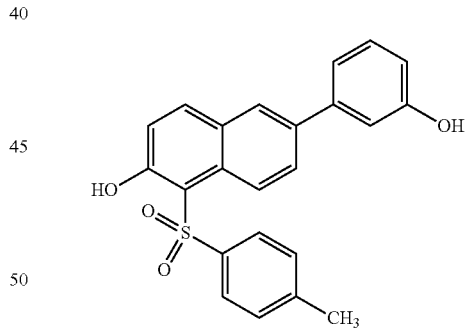

To a solution of 2-methoxy-6-(3-methoxyphenyl)-1-[(4-methylphenyl)sulfanyl]-naphthalene (385 mg, 1.03 mmol, 1 eq; prepared by analogy with 6-(3-hydroxyphenyl)-1-(phenylsulfanyl)-2-naphthol from 1-bromo-2-methoxy-6-methoxyphenyl)naphthalene and 4-methylbenzenethiolate, followed by ether cleavage of the intermediate compound (method G)) in anhydrous dichloromethane (10 ml), a solution of m-CPBA (1.42 g, 8.24 mmol, 8.2 eq) in dichloromethane (10 ml) was added dropwise at 0° C. The reaction mixture was stirred at first at 0° C. for one hour, then at room temperature for twelve hours, and subsequently poured into ice water. The aqueous phase was extracted with ethyl acetate. The combined organic phases were washed with sodium hydrogencarbonate solution and water and dried over Na$_2$SO$_4$. Purification by column chromatography (SiO$_2$; dichloromethane: methanol=95:5) yielded the analytically pure compound. Yield: 80 mg (79%).

C$_{23}$H$_{18}$O$_4$S; MW 390; $^1$H-NMR (acetone-d$_6$): δ 8.49 (d, J=8.8 Hz, 1H), 8.22 (d, J=8.8 Hz, 1H), 8.12 (d, J=2.1 Hz, 1H), 7.95 (d, J=8.5 Hz, 1H), 7.82 (dd, J=2.1 Hz, J=8.3 Hz, 1H), 7.43 (d, J=8.8 Hz, 2H), 7.31-7.26 (m, 2H), 7.19 (m, 2H), 6.87 (m, 1H); MS (ESI): 389 (M–H)$^-$.

Biological Data

1.) 17β-HSD1 Test Assay:

Recombinant protein obtained from Sf9 insect cells (0.1 μg/ml) is incubated with 20 mM KH$_2$PO$_4$, pH 7.4, 30 nM $^3$H-estrone and 1 mM NADPH for 30 min at RT in the presence of the potential inhibitor in a concentration of 1 μM or 100 nM. The stock solutions of the compounds are prepared in DMSO (dimethylsulfoxide) so that the final concentration of DMSO in the sample is 1%. After the prescribed incubation time, the reaction is quenched by adding trichloroacetic acid (10% final concentration). The samples are centrifuged in microtitration plates at 400 rpm for 10 min, and the supernatants are charged on a reversed-phase HPLC equipped with a Waters Symmetrie C18 column and Waters Sentry Guard column. The isocratic HPLC run is performed at RT with a flow rate of 1 ml/min and acetonitrile/water 48:52 as the eluent. The radioactivity was measured by means of a Packard Flow Scintillation Analyzer. The total radioactivity of estrone and estradiol was calculated by means of the following formula:

$$\% \text{ conversion} = 100 * \frac{cpm \text{ estradiol in sample with inhibitor}}{(cpm \text{ estrone in sample with inhibitor}) + (cpm \text{ estradiol in sample with inhibitor})} \cdot \frac{cpm \text{ estradiol in sample with no inhibitor}}{(cpm \text{ estrone in sample with no inhibitor}) + (cpm \text{ estradiol in sample with no inhibitor})}$$

The percent inhibition is calculated therefrom as follows:

% inhibition=100−% conversion (cpm=counts per minute)

2.) 17β-HSD2 Test Assay:

Recombinant protein obtained from Sf9 insect cells (0.1 μg/ml) is incubated with 20 mM KH$_2$PO$_4$, pH 7.4, 30 nM $^3$H-estradiol and 1 mM NAD+ for 30 min at RT in the presence of the potential inhibitor in a concentration of 1 μM or 100 nM. The stock solutions of the compounds are prepared in DMSO so that the final concentration of DMSO in the sample is 1%. After the prescribed incubation time, the reaction is quenched by adding trichloroacetic acid (10% final concentration). The samples are centrifuged in microtitration plates at 400 rpm for 10 min, and the supernatants are charged on a reversed-phase HPLC equipped with a Waters Symmetrie C18 column and Waters Sentry Guard column. The isocratic HPLC run is performed at RT with a flow rate of 1 ml/min and acetonitrile/water 48:52 as the eluent. The radioactivity was measured by means of a Packard Flow Scintillation Analyzer. The percent inhibition was calculated by means of the formulas stated above. The results are summarized in the Table.

TABLE 1

| | 17β-HSD test assay | | | |
|---|---|---|---|---|
| Compound | HSD1 100 nM | HSD 1 μM | HSD2 100 nM | HSD2 1 μM |
| 1 | no inh. | no inh. | n.d. | n.d. |
| 14 | no inh. | no inh. | n.d. | n.d. |
| 13 | no inh. | no inh. | n.d. | n.d. |
| 15 | no inh. | no inh. | n.d. | n.d. |
| 16 | 24.0 | 56.9 | n.d. | n.d. |
| 12 | 24.0 | 56.9 | n.d. | n.d. |
| 17 | 30.3 | 57.7 | n.d. | n.d. |
| 3 | 26 | 61 | n.d. | n.d. |
| 2 | no inh. | no inh. | n.d. | n.d. |
| 18 | no inh. | no inh. | n.d. | n.d. |
| 19 | 91.4 | 94.0 | 12.4 | 16.6 |
| 20 | no inh. | no inh. | n.d. | n.d. |
| 21 | no inh. | no inh. | n.d. | n.d. |
| 22 | no inh. | no inh. | n.d. | n.d. |
| 24 | no inh. | no inh. | n.d. | n.d. |
| 25 | no inh. | no inh. | n.d. | n.d. |
| 22 | no inh. | no inh. | n.d. | n.d. |
| 23 | no inh. | no inh. | n.d. | n.d. |
| 7 | 36.3 | 75.8 | n.d. | n.d. |
| 9 | no inh. | 18.5 | n.d. | n.d. |
| 10 | no inh. | no inh. | n.d. | n.d. |
| 11 | no inh. | 12.9 | n.d. | n.d. |
| 8 | no inh. | no inh. | n.d. | n.d. |
| 5 | no inh. | no inh. | n.d. | n.d. |
| 6 | no inh. | no inh. | n.d. | n.d. |
| 4 | no inh. | 31.6 | n.d. | n.d. |
| 26 | 14.3 | 41.7 | n.d. | n.d. |
| 27 | no inh. | no inh. | n.d. | n.d. |
| 28 | no inh. | no inh. | n.d. | n.d. |
| 29 | no inh. | no inh. | n.d. | n.d. |
| 30 | no inh. | no inh. | n.d. | n.d. |
| 31 | no inh. | no inh. | n.d. | n.d. |
| 32 | no inh. | 19.6 | n.d. | n.d. |
| 33 | no inh. | no inh. | n.d. | n.d. |
| 34 | no inh. | 13.6 | n.d. | n.d. |
| 35 | no inh. | no inh. | n.d. | n.d. |
| 36 | no inh. | no inh. | n.d. | n.d. |
| 37 | no inh. | 18 | n.d. | n.d. |
| 38 | 17 | 62 | n.d. | n.d. |
| 39 | 19.2 | 57.6 | 33.9 | 73.2 |
| 40 | no inh. | 60.4 | 28.1 | 76.9 |
| 55 | no inh. | 80.0 | no inh. | 35.8 |
| 41 | 21.8 | 76.3 | no inh. | 21.6 |
| 42 | 40.0 | 80.2 | no inh. | 16.3 |
| 43 | 20.5 | 69.9 | no inh. | no inh. |
| 44 | 27.8 | 62.4 | n.d. | n.d. |
| 51 | 28.8 | 73.4 | n.d. | n.d. |
| 45 | no inh. | 44.5 | n.d. | n.d. |
| 46 | no inh. | 53 | n.d. | n.d. |
| 47 | 43 | 70 | n.d. | n.d. |
| 48 | n.d. | 68 | n.d. | 24 |
| 49 | 37 | 84 | n.d. | n.d. |
| 50 | no inh. | 40 | n.d. | n.d. |
| 53 | 32.3 | 74.4 | 18 | 67 |
| 54 | 83.0 | 94.0 | n.d. | n.d. |
| 52 | 82.9 | 88.4 | 19 | 69 |
| 59 | 87.4 | 92.3 | 66.1 | 90.3 |
| 60 | 74.4 | 85.9 | 12.2 | 48.5 |
| 58 | 83.0 | 89.1 | 60.6 | 92.3 |
| 61 | no inh. | 22.1 | 15.5 | 51.7 |
| 56 | 76.2 | 89.4 | 22.1 | 77.2 |
| 57 | 82.9 | 92.6 | no inh. | 40.1 |
| 63 | 44.7 | 80.0 | no inh. | 34.2 |
| 68 | 74.1 | 87.3 | no inh. | 39.1 |
| 65 | 31.9 | 64.9 | 12.4 | 31.9 |
| 67 | no inh. | 62.3 | 24.2 | 68.0 |
| 62 | 85.9 | 89.2 | 24.3 | 67.2 |
| 66 | 35.1 | 81.5 | 24.1 | 63.6 |
| 64 | 88.1 | 90.8 | 31.1 | 71.3 |
| 71 | 66.4 | 74.7 | n.d. | n.d. |
| 72 | 62.2 | 74.0 | n.d. | n.d. |
| 90 | 16.5 | 77.3 | n.d. | n.d. |
| 69 | 87.0 | 96.3 | 24 | 71 |
| 70 | 82.2 | n.d. | n.d. | n.d. |
| 89 | 68.0 | 78.2 | n.d. | n.d. |

TABLE 1-continued

17β-HSD test assay

| Compound | HSD1 100 nM | HSD 1 μM | HSD2 100 nM | HSD2 1 μM |
|---|---|---|---|---|
| 88 | 76.8 | 82.4 | n.d. | n.d. |
| 73 | 71.2 | 80.5 | n.d. | n.d. |
| 74 | 46.4 | 78.0 | n.d. | n.d. |
| 75 | 72.8 | 78.9 | n.d. | n.d. |
| 76 | 62.1 | 79.7 | n.d. | n.d. |
| 77 | 73.2 | 79.9 | n.d. | n.d. |
| 78 | 63.7 | 79.2 | n.d. | n.d. |
| 79 | 73.8 | 80.2 | n.d. | n.d. |
| 80 | 64.7 | 79.4 | n.d. | n.d. |
| 81 | 71.5 | 82.9 | n.d. | n.d. |
| 82 | 40.5 | 78.4 | n.d. | n.d. |
| 83 | 49.8 | 78.1 | n.d. | n.d. |
| 84 | 66.3 | 79.3 | n.d. | n.d. |
| 85 | 54.5 | 77.7 | n.d. | n.d. |
| 86 | 71.6 | 80.9 | n.d. | n.d. |
| 87 | 71.7 | 80.6 | n.d. | n.d. |
| 91 | n.d. | 33 | n.d. | n.d. |
| 92 | n.d. | 75 | n.d. | n.d. | no inh. = no inhibition (inhibition below 10%)
n.d. = not determined

3. Estrogen Receptor Binding Assay:

The percent binding of the compounds to estrogen receptors α and β was determined in accordance with the method described by Zimmermann et al. (Zimmermann, J. et al., J. Steroid Biochem. Mol. Biol., 94: 57-66 (2005)). Slight changes were introduced, namely the binding incubation was effected at RT for 2 h with shaking, and after the addition of hydroxylapatite (HAP), the mixture was incubated on ice for 15 min and vortexed every 5 min. The results are summarized in Table 2.

TABLE 2

Estrogen receptor binding assay

| Compound | RBA ERα [%] | RBA ERβ [%] |
|---|---|---|
| 19 | 0.23 | 0.80 |
| 52 | 0.081 | 0.10 |
| 56 | 0.055 | 0.044 |
| 57 | 0.0013 | 0.020 |
| 58 | 0.022 | 0.024 |
| 60 | 0.0068 | 0.003 |
| 64 | 0.012 | 0.007 |
| 69 | 0.015 | 0.010 |
| Estrone | 2.1 | 1.6 |
| Estradiol | 100 | 100 |

RBA: relative binding affinity (estradiol: 100%)

4. Determination of the $IC_{50}$ Values:

The determination of the $IC_{50}$ values was performed with enzyme isolated from human placenta (Luu-The, V. et al., J. Steroid Biochem. Mol. Biol., 55: 581-587 (1995); Sam, K. M. et al., Drug Des. Discov., 15: 157-180 (1997)). The microsomal fraction obtained by processing contains the enzyme 17β-HSD2, while the 17β-HSD1, which is required for the test, is found in the cytosolic fraction. To this partially purified 17β-HSD1 is added 20 mM $KH_2PO_4$, pH 7.4, 10 nM [$^3$H]-estrone/490 nM estrone, 500 μM NADH and the compound to be tested in different concentrations. This solution is incubated with shaking at 37° C. for 30 min. The reaction is quenched by adding 10 mM $HgCl_2$. After addition of 1 ml of diethyl ether and shaking for 10 min, the samples are centrifuged at 6000 rpm for 5 min. The ether phase is transferred and evaporated. The residue is dissolved in acetonitrile, and the estrone/estradiol mixture contained therein is separated by means of HPLC, and the radioactivity is determined by means of scintillation measurement. Using the thus obtained values, it is possible to calculate the amount of transformed estrone and the percent inhibition. The results are summarized in Table 3.

TABLE 3

Determination of $IC_{50}$ values

| Compound | 17β-HSD1 $IC_{50}$ (nM) | 17β-HSD2 $IC_{50}$ (nM) | Selectivity $IC_{50}(HSD2)/IC_{50}(HSD1)$ |
|---|---|---|---|
| 19 | 70 | 5641 | 80 |
| 42 | 500 | 4190 | 8 |
| 52 | 39 | 583 | 15 |
| 54 | 840 | 500 | 0.6 |
| 56 | 23 | 540 | 24 |
| 57 | 20 | 959 | 48 |
| 58 | 40 | 527 | 13 |
| 59 | 20 | 1160 | 58 |
| 60 | 90 | 2937 | 33 |
| 62 | 50 | 458 | 9 |
| 63 | 140 | n.d. | n.d. |
| 64 | 10 | 403 | 40 |
| 66 | 114 | n.d. | n.d. |
| 68 | 50 | 1760 | 44 |
| 69 | 7 | 601 | 87 |
| 70 | 30 | 195 | 6.5 |
| 71 | 60 | n.d. | n.d. | n.d. = not determined

5. CaCo-2 Assay:

Caco-2 cell culture and transport experiments were performed according to Yee (Yee, S., Pharm. Res., 14: 763-766 (1997)), but slight modifications were introduced. The cultivation times were reduced from 21 to 10 days by increasing the sowing density from $6.3 \cdot 10^4$ to $1.65 \cdot 10^5$ cells per well. Four reference compounds (atenolol, testosterone, ketoprofene and erythromycin) were employed in each assay for evaluating the transport properties of the CaCo-2 cells. The initial concentration of the compounds in the donor compartment was 50 μM (in buffer with 1% ethanol or DMSO). Samples were taken from the acceptor side after 60, 120 and 180 min and from the donor side after 0 and 180 min. For glycoprotein P (P-gp) studies, bidirectional experiments were performed. The absorptive and secretory permeabilities ($P_{app(a-b)}$ and $P_{app(b-a)}$) were determined. Thus, erythromycin was used as a substrate, and verapamil was used as an inhibitor of P-gp. Each experiment was performed in triplicate. The integrity of the monolayer was determined by means of TEER (transepithelial electric resistance) and the permeability for each assay was determined using Lucifer Yellow. All samples of the CaCo-2 transport experiments were analyzed by means of LC/MS/MS after dilution with buffer (1:1 with 2% acetic acid). The apparent permeability coefficient ($P_{app}$) was calculated by means of formula (1) as given below, where dQ/dt represents the recovery rate of the mass in the acceptor compartment, A represents the surface area of the transwell membrane, and $c_0$ represents the initial concentration in the donor compartment. The results are summarized in Table 4.

$$P_{app} = \frac{dQ}{dt \cdot A \cdot c_0} \quad (1)$$

TABLE 4

CaCo-2 assay

| Compound | final basolateral concentration [μM ± SD] | $P_{app}$ values [×10$^6$ cm/s] | mass balance [% ± SD] | Permeability |
|---|---|---|---|---|
| 19 | 6.5 ± 0.2 | 8.9 | 37.5 ± 3.0 | moderate |
| 42 | 1.1 ± 0.1 | 1.5 | 7.6 ± 0.5 | moderate |
| 54 | 3.7 ± 0.3 | 4.4 | 30.5 ± 3.1 | moderate |
| 59 | 11.0 ± 0.5 | 13.8 | 29.9 ± 2.4 | high |
| 68 | 13.9 ± 0.8 | 16.4 | 52.7 ± 3.6 | high |
| 70 | 0.9 ± 0.08 | 1.5 | 23.0 ± 2.3 | moderate |

6. Test for Metabolic Stability
LC-MS:

As a starting solution for the LC-MS to be performed, a 1 mg/ml solution in acetonitrile was used, which was diluted with a mixture of acetonitrile and 10 mM ammonium acetate/ 0.1% formic acid (1:1, v/v) to a final concentration of 10 μg/ml. Full scan mass spectra were recorded in positive mode. Characteristic fragments were recorded using the following parameters: 350° C. temperature of the ion source, 3.8 kV capillary voltage, 0.8 mbar argon.

Metabolic Stability:

The stock solutions (10 mM in ACN) are diluted to obtain working concentrations in 20% ACN which are 10 times higher than the incubation concentrations of the compounds. The assay was performed with liver microsomes of rats.

The incubation solution (180 μl) consists of 90 μl of a microsomal suspension of 0.33 mg/ml protein in 100 mM phosphate buffer, pH 7.4, with 90 μl NADP-regenerating system (NADP: 1 mM, glucose-6-phosphate 5 mM, glucose-6-phosphate dehydrogenase: 5 U/ml, MgCl$_2$ 5 mM).

The reaction is started by adding 20 μl of the compound to be tested in 20% ACN to the microsome/buffer mixture preincubated at 37° C. After 0, 15, 30 and 60 minutes, 200 μl of sample solution is withdrawn and subjected to ACN precipitation. The isolation of the compounds is effected by adding 200 μl ACN that contains the internal standard (1 μM) to 200 μl of sample solution and calibration standard. After shaking for 10 s and centrifugation at 4000 g, an aliquot of the supernatant is subjected to LC-MS/MS. Two controls are included, namely a positive control with 7-ethoxycoumarin as a reference to verify the microsomal enzyme activity, and a negative control in which microsomes are used that were heated for 25 minutes without a regenerating system, in order to ensure that the loss of substance is actually due to metabolization.

The amount of compound in a sample is expressed as the percent fraction of the compound remaining as compared to time t=0 (100%). The percent fraction is plotted versus time. The results are summarized in Table 5.

TABLE 5

Test for metabolic stability:

| Compound | Slope (−k) | Correlation (R$^2$) | Linearity range (min) | Half life (min) | Intrinsic clearance (μl/min/mg protein) |
|---|---|---|---|---|---|
| 59 | −0.051 | 0.991 | 0-30 | 13.6 | 339.5 |
| 19 | −0.055 | 0.996 | 0-30 | 12.6 | 366.9 |
| 62 | −0.014 | 0.985 | 0-30 | 49.8 | 92.8 |
| 70 | −0.002 | 0.923 | 0-30 | 449.8 | 10.3 |
| diazepam | −0.017 | 0.994 | 0-30 | 40.77 | 113.3 |
| diphenhydramine | −0.102 | 0.999 | 0-30 | 6.80 | 679.6 |

7. Inhibition of P450 Enzymes

TABLE 6

Final concentrations in P450 screening assay

| | CYP1A2 | CYP2B6 | CYP2C9 | CYP C19 | CYP2D6 | CYP3A4 |
|---|---|---|---|---|---|---|
| Substrates | CEC | EFC | MFC | CEC | AMMC | BFC |
| | 5 μM | 2.5 μM | 75 μM | 25 μM | 1.5 μM | 50 μM |
| Metabolites formed | CHC | HFC | HFC | CHC | AHMC | HFC |
| NADP$^+$ | 1.3 mM | 1.3 mM | 1.3 mM | 1.3 mM | 8.2 μM | 1.3 mM |
| Glucose-6-phosphates | 3.3 mM | 3.3 mM | 3.3 mM | 3.3 mM | 0.41 mM | 3.3 mM |
| MgCl$_2$*6H$_2$O | 3.3 mM | 3.3 mM | 3.3 mM | 3.3 mM | 0.41 mM | 3.3 mM |
| Glucose-6-phosphate dehydrogenase | 0.4 U/ml | 0.4 U/ml | 0.4 U/ml | 0.4 U/ml | 0.4 U/ml | 0.4 U/ml |
| PO$_4^{3-}$, pH 7.4 | 100 mM | 100 mM | 25 mM | 50 mM | 100 mM | 200 mM |
| Enzyme | 2.5 pmol/ml | 5 pmol/ml | 5 pmol/ml | 2.5 pmol/ml | 7.5 pmol/ml | 15 pmol/ml |
| positive control (highest conc.) | Furafylline | Tranylcypromine | Sulfaphenazole | Tranylcypromine | Quinidine | Ketoconazole |
| | 100 μM | 125 μM | 10 μM | 100 μM | 0.5 μM | 5 μM |
| Test conc. compounds | 2 μM | 5 μM | 0.3 μM | 2 μM | 0.02 μM | 0.05 μM |
| | 20 μM | 50 μM | 3 μM | 20 μM | 0.2 μM | 0.5 μM |

Abbreviations:
CEC 3-cyano-7-ethoxycoumarin,
MFC 7-methoxy-4-trifluoro-methylcoumarin,
AMMC 3-[2-(N,N-diethyl-N-methylamino)ethyl]-7-methoxy-4-methylcoumarin,
BFC 7-benzyloxytrifluoromethylcoumarin,
CHC 3-cyano-7-hydroxycoumarin,
HFC 7-hydroxytrifluoromethylcoumarin,
EFC 7-ethoxy-4-trifluoromethylcoumarin and
AHMC 3-[2-(N,N-diethylamino)ethyl]-7-hydroxy-4-methylcoumarin.

P450 Inhibition Assay:

The assay is performed in 96 well plates. The compounds to be tested are dissolved in acetonitrile in a concentration of 50 mM, wherein the solubility of the compounds may be increased by adding 3% (v/v) 1 N HCl if needed. For the determination of the $IC_{50}$ values, the 50 mM stock solution in the first well is diluted 50 times, followed by a 1:3 dilution from well 1 to well 8. For CYP1A2, a 1 mM stock solution is used. A cofactor mix consisting of an NADP+-regenerating system and a cofactor acetonitrile mix is used. The final concentration of acetonitrile is 1%.

After 10 min preincubation at 37° C., the reaction is started by adding the preheated enzyme/substrate mixture. The incubation of the 200 μl/well is effected at 37° C. for 15 min. The reaction is quenched by adding 75 μl/well of stock solution consisting of 60% acetonitrile and 40% 0.1 M Tris, pH 9.

Fluorescence Measurement:

The fluorescent metabolites were determined by means of Wallac Victor. Excitation and emission wavelengths are stated in Table 7.

TABLE 7

Excitation and emission wavelengths

| | CYP1A2 | CYP2B6 | CYP2C9 | CYP C19 | CYP2D6 | CYP3A4 |
|---|---|---|---|---|---|---|
| Metabolites | CHC | HFC | HFC | CHC | AHMC | HFC |
| Excitation wavelength | 405 nm | 409 nm | 405 nm | 405 nm | 380 nm | 405 nm |
| Emission wavelength | 460 nm | 530 nm | 535 nm | 460 nm | 460 nm | 535 nm |

$IC_{50}$ Calculation:

The calculation of the $IC_{50}$ value was effected according to the following formula (2). The results are summarized in Table 8.

$$IC_{50} = \frac{(50\% - \text{Low \% Inhibition})}{(\text{High \% Inhibtion} - \text{Low \% Inhibition})} \times (HighConc. - LowConc.) + LowConc. \quad (2)$$

8. In Vivo Pharmacokinetics (Rat)

Single Administration:

Upon oral administration of compounds 68 or 59 to adult male Wistar rats (n=5; vehicle: Labrasol/water 1/1), the plasma profiles were established by means of LC-MS/MS. The data obtained are summarized in Table 9.

TABLE 9

Single administration to male Wistar rats

| | Compound | |
|---|---|---|
| Parameter | 68 | 59 |
| Dose (mg/kg) | 50 | 50 |
| $C_{max\,obs}$ (ng/kg) | 44.1 | 15.7 |
| $C_z$ (ng/kg) | 13.5 | 18.0 |
| $t_{max\,obs}$ (h) | 2.0 | 2.0 |
| $t_z$ (h) | 8.0 | 8.0 |
| $t_{1/2z}$ (h) | 1.59 | 1.54 |

TABLE 9-continued

Single administration to male Wistar rats

| | Compound | |
|---|---|---|
| Parameter | 68 | 59 |
| $AUC_{0-z}$ (ng · h/ml) | 336.7 | 203.4 |
| $AUC_{0-\infty}$ (ng · h/ml) | 336.7 | 203.4 |

$C_{max\,obs}$ highest measured concentration

TABLE 8

$IC_{50}$ values [μM] of the test compounds and control inhibitors for the CYP enzymes

| | $IC_{50}$ (mean ± SD) [μM] | | | | | |
|---|---|---|---|---|---|---|
| Iso-enzyme | CYP1A2 | CYP2B6 | CYP2C9 | CYP2C19 | CYP2D6 | CYP3A4 |
| 59 | 0.014 ± 0.00 | 5.34 ± 0.391 | 0.15 ± 0.03 | 0.88 ± 0.03 | 22.90 ± 1.85 | 0.221 ± 0.002 |
| 19 | 3.99 ± 0.25 | 13.4 ± 0.45 | 1.05 ± 0.02 | 7.54 ± 0.51 | 32.56 ± 0.72 | 1.58 ± 0.04 |
| 62 | 10.45 ± 0.29 | 10.4 ± 0.14 | 1.25 ± 0.07 | 0.680 ± 0.056 | 40.00 ± 0.08 | 1.07 ± 0.05 |
| 54 | 0.259 ± 0.010 | autofl., 405 nm | 0.224 ± 0.002 | 1.21 ± 0.19 | autofl., 405 nm | 2.05 ± 0.18 |
| 70 | 37.50 ± 0.786 | 13.60 ± 1.08 | 0.03 ± 0.00 | 8.83 ± 0.49 | 39.35 ± 0.14 | 2.25 ± 0.12 |
| Positive control | Furafylline | Tranylcypromine | Sulfaphenazole | Tranylcypromine | Quinidine | Ketoconazole |
| $IC_{50}$ [μM] | 3.04 ± 0.08 | 6.96 ± 0.025 | 0.250 ± 0.027 | 3.04 ± 0.17 | 0.011 ± 0.001 | 0.054 ± 0.001 |

TABLE 9-continued

Single administration to male Wistar rats

| Parameter | Compound | |
|---|---|---|
| | 68 | 59 |

$C_z$ last analytically quantifiable concentration
$t_{max\ obs}$ time to reach the highest measured concentration
$t_z$ time to withdrawal of the last sample with analytically quantifiable concentration
$t_{1/2z}$ half life (determined from the slope of the declining portion of the concentration vs. time curve
$AUC_{0-tz}$ area below the concentration vs. time curve up to time $t_Z$
$AUC_{0-\infty}$ area below the concentration vs. time curve, extrapolated to $\infty$ Cassette Dosing Method:

Compounds 19, 56, 57, 64 and 68 (as reference) were administered perorally to adult male Wistar rats (n=4) in a cassette dosing method (vehicle: Labrasol/water 1/1). The plasma profiles were established by means of LC-MS/MS. The data obtained are summarized in Table 10.

TABLE 10

Cassette dosing with male Wistar rats

| Parameter | Compound | | | | |
|---|---|---|---|---|---|
| | 68 | 19 | 56 | 57 | 64 |
| Dose (mg/kg) | 10 | 10 | 10 | 10 | 10 |
| $C_{max\ obs}$ (ng/kg) | 43.2 | 2226.5 | 860.5 | 843.7 | 110.0 |
| $C_z$ (ng/kg) | 0.38 | 159.06 | 114.57 | 557.27 | 66.58 |
| $t_{max\ obs}$ (h) | 2.0 | 6.0 | 4.0 | 6.0 | 2.0 |
| $t_z$ (h) | 24.0 | 24.0 | 24.0 | 10.0 | 10.0 |
| $T_{1/2z}$ (h) | 2.4 | 4.4 | 5.9 | 0.9 | 1.1 |
| $AUC_{0-tz}$ (ng · h/ml) | 539.0 | 29693.8 | 11701.5 | 10680.6 | 1331.6 |
| $AUC_{0-\infty}$ (ng · h/ml) | 540.3 | 30698.0 | 12669.3 | 10680.6 | 1331.6 |

Legend see Table 9.

The invention claimed is:
1. A compound of the structure (I):

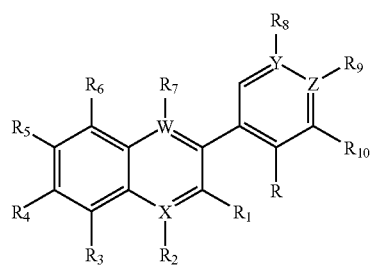

(I)

wherein
W and X each represent —C═
Y and Z are independently —C═ or —N═,
R is H, halogen, alkyl, alkoxy or alkylsulfanyl,
$R_1$ is H, halogen, OH, CN, COOH, alkyl, alkoxy, alkylsulfanyl, aryl, heteroaryl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R' or —SOR',
$R_2$ is H, halogen, OH, CN, COOH, alkyl, alkoxy, alkylsulfanyl, aryl, heteroaryl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R' or —SOR',
$R_3$ is H, halogen, OH, CN, COOH, alkyl, alkoxy, alkylsulfanyl, aryl, heteroaryl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R', or —SOR',
$R_4$ is OH,
$R_5$ is H, halogen, OH, CN, COOH, alkyl, alkoxy, alkylsulfanyl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R' or —SOR',
$R_6$ is H, halogen, OH, CN, COOH, alkyl, alkoxy, alkylsulfanyl, aryl, heteroaryl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R' or —SOR',
$R_7$ is H, halogen, OH, CN, COOH, alkyl, alkoxy, alkylsulfanyl, aryl, heteroaryl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R' or —SOR',
$R_8$ is H, halogen, OH, CN, COOH, alkyl, alkoxy, alkylsulfanyl, aryl, heteroaryl, arylsulfanyl, —NHSO₂R', —R"—NHSO₂R', —SO₂NHR', —R"—SO₂NHR', —NHCOR', —CONHR', —R"—NHCOR', —R"—CONHR', —COOR', —OOCR', —R"—COOR', —R"—OOCR', —CHNR', —SO₂R' or —SOR', or is absent if Y is —N═,
$R_9$ is H, halogen, CN, COOH or CH₂OH, or is absent if Z is —N═, and
$R_{10}$ is H, OH, CN, COOH, CH₂OH, NO₂ or NH₂,
with the proviso that at least one of $R_8$ and $R_{10}$ is OH or COOH,
R' is alkyl, aryl or heteroaryl,
R" is alkylene, arylene or heteroarylene,
the aryl, arylene, heteroaryl and heteroarylene residues in $R_1$, $R_2$, $R_3$, $R_5$, $R_6$, $R_7$, $R_8$, R' and R" may be substituted with 1 to 5 residues R'" and wherein the residues R'" are independently selected from halogen, OH, CN, alkyl, alkoxy, halogenated alkyl, halogenated alkoxy, alkylsulfanyl, arylsulfanyl, heteroarylsulfanyl, aryl, heteroaryl (wherein these aryl and heteroaryl residues may optionally have up to 3 substituents selected from halogen, OH, CN, lower alkyl, lower alkoxy, halogenated lower alkyl, halogenated lower alkoxy, (lower alkyl)sulfanyl, —COOR₁₁, —CH₂OH, —NO₂ and —N(R₁₁)₂), -(lower alkylene)-NHSO₂R"", -(lower alkylene)-SO₂NHR"", -(lower alkylene)-NH-COR"", -(lower alkylene)-CONHR"", -(lower alkylene)-COOR"", -(lower alkylene)-OOCR"", (wherein R"" is optionally halogenated lower alkyl, optionally halogenated lower alkoxy, aryl or heteroaryl), —COOR₁₁, —CH₂OH, —NO₂ and —N(R₁₁)₂,
the alkyl, alkoxy- and alkylene residues in R, $R_1$, $R_2$, $R_3$, $R_5$, $R_6$, $R_7$, $R_8$, R' and R" may be substituted with 1 to 3 residues independently selected from halogen, OH, CN, lower alkyl, lower alkoxy, halogenated lower alkyl, halogenated lower alkoxy, (lower alkyl)sulfanyl, —COOR₁₁, —CH₂OH, —NO₂ and N(R₁₁)₂, and $R_{11}$ is independently selected from H and lower alkyl, or two residues $R_{11}$ form a 5- to 7-membered saturated heterocycle together with the N atom linking them, or a pharmacologically acceptable salt thereof, with the proviso that:

if W, X, Y and Z are —C=, $R_4$ is OH, R, $R_1$, $R_2$, $R_3$, $R_5$, $R_6$, $R_7$ and $R_9$ are H, then one of $R_8$ and $R_{10}$ is not OH and the other is H.

2. A pharmaceutical composition comprising at least one of the compounds according to claim 1 and optionally a pharmacologically suitable carrier.

3. The compound according to claim 1, wherein:
(i) R is H, halogen, lower alkyl, lower alkoxy or (lower alkyl)sulfanyl; and/or
(ii) one of $R_3$ and $R_5$ is H, halogen, OH, CN, COOH, alkyl, alkoxy, alkylsulfanyl, arylsulfanyl, —NHSO$_2$R', —R"—NHSO$_2$R', —SO$_2$NHR', —R"—SO$_2$NHR', —NHCOR', —CONHR', —R"—NHCOR', —R"—CONHR', —COOR', —OOCR', —R"—COOR', —R"—OOCR', —CHNR', —SO$_2$R' or —SOR' (wherein R' and R" have the meanings as stated in claim 1 and, like the aryl, arylene, heteroaryl and heteroarylene residues, may be substituted with 1 to 3 residues R''', and R''' has the meaning as stated in claim 1), and the other of the two residues $R_3$ and $R_5$, like the residues $R_1$, $R_2$, $R_6$ and $R_7$, is optionally selected from H, halogen, OH, CN, COOH, lower alkyl, lower alkoxy, (lower alkyl)sulfanyl, arylsulfanyl, —NHSO$_2$R', —SO$_2$NHR', —NHCOR', —CONHR', —COOR', —OOCR', CHNR', —SO$_2$R' and —SOR' (wherein R' is lower alkyl, phenyl or pyridinyl); and/or
(iii) $R_8$ is H, halogen, hydroxy, CN, COOH, lower alkyl, lower alkoxy, (lower alkyl)sulfanyl, aryl, heteroaryl, arylsulfanyl, —NHSO$_2$R', —SO$_2$NHR', —NHCOR', —CONHR', —COOR', —OOCR', —CHNR', —SO$_2$R' or —SOR' (wherein R' is lower alkyl, phenyl or pyridinyl); and/or
(iv) $R_9$ is H, CN, COOH or CH$_2$OH, or is absent if Z is —N=; and/or
(v) a compound is excluded in which W, X, Y and Z are —C=, $R_4$ is OH, R, $R_1$, $R_2$, $R_3$, $R_5$, $R_6$, $R_7$ and $R_9$ are H, and one of $R_8$ and $R_{10}$ is OH and the other is H.

4. The compound according to claim 1, wherein:
(i) W, X, Y and Z are —C=; and/or
(ii) $R_3$ is selected from H, halogen, OH, CN, COOH, alkyl, alkoxy, alkylsulfanyl, aryl, heteroaryl, arylsulfanyl, —NHSO$_2$R', —R"—NHSO$_2$R', —SO$_2$NHR', —R"—SO$_2$NHR', —NHCOR', —CONHR', —R"—NHCOR', —R"—CONHR', —COOR', —OOCR', —R"—COOR', —R"—OOCR', —CHNR', —SO$_2$R' and —SOR' (wherein R' and R" have the meanings as stated in claim 1 and may be substituted with 1 to 3 residues R''' and R''' has the meaning as stated in claim 1); and/or
(iii) $R_1$, $R_2$, $R_6$ and $R_7$ are independently selected from H, halogen, hydroxy, CN, COOH, lower alkyl, lower alkoxy, (lower alkyl)sulfanyl, phenyl, pyridyl, phenylsulfanyl, —NHSO$_2$R', —SO$_2$NHR', —NHCOR', —CONHR', SO$_2$R' and —SOR' (wherein R' is lower alkyl, phenyl or pyridinyl); and/or
(iv) $R_8$ is H, halogen, hydroxy, CN, COOH, lower alkyl, lower alkoxy, (lower alkyl)sulfanyl, phenyl, pyridyl, phenylsulfanyl, —NHSO$_2$R', —SO$_2$NHR', —NHCOR', —CONHR', —SO$_2$R' or —SOR' (wherein R' is lower alkyl, phenyl or pyridinyl); and/or
(v) $R_{10}$ is H, OH, CN, COOH or CH$_2$OH; and/or
(vi) at least one of $R_8$ and $R_{10}$ is OH.

5. The compound according to claim 4, wherein:
W, X, Y and Z are —C=;
R, $R_1$, $R_5$, $R_7$ and $R_9$ are H;
at least one of $R_8$ and $R_{10}$ is OH, and
$R_2$, $R_3$, and $R_6$ independently have the meaning as stated in claim 4.

6. The compound according to claim 1, wherein the compound of structure (I) is selected from the following compounds: 3-(2-naphthyl)phenol (3), 3-(6-hydroxy-2-naphthyl)pyridine (4), 3-(6-hydroxy-2-naphthyl)benzoic acid (7), 4-(6-hydroxy-2-naphthyl)benzoic acid (8), N-[3-(6-hydroxy-2-naphthyl)phenyl]acetamide (9), 6-[3-(hydroxymethyl)phenyl]-2-naphthol (10), 6-[4-(hydroxymethyl)phenyl]-2-naphthol (11), 2-(3-hydroxyphenyl)quinoline-6-ol (12), 3-(quinoline-3-yl)phenol (13), 3-(4-hydroxyphenyl)-quinoline-7-ol (15), 3-(3-hydroxyphenyl)quinoline-7-ol (16), 5-(6-hydroxynaphthalene-2-yl)pyridine-3-ol (17), 6-(2-hydroxyphenyl)-2-naphthol (18), 6-(3-hydroxyphenyl)-1-naphthol (24), 6-(3-hydroxy-5-methylphenyl)-2-naphthol (26), 5-(6-hydroxy-2-naphthyl)-1,1'-biphenyl-3,4'-diol (27), 6-[3-hydroxy-5-(6-hydroxy-2-naphthyl)phenyl]-2-naphthol (28), 3-hydroxy-5-(6-hydroxy-2-naphthyl)-N-methylbenzamide (29), 3-hydroxy-5-(6-hydroxy-2-naphthyl)-N-phenylbenzamide (30), (E)-3-[3-hydroxy-5-(6-hydroxy-2-naphthyl)phenyl]-N-methylacrylamide (31), (E)-3-[3-hydroxy-5-(6-hydroxy-2-naphthyl)phenyl]-N-phenylacrylamide (32), 3-[3-hydroxy-5-(6-hydroxy-2-naphthyl)phenyl]-N-methylpropionamide (33), 3-[3-hydroxy-5-(6-hydroxy-2-naphthyl)phenyl]-N-phenylpropionamide (34), N-[2-hydroxy-4-(6-hydroxy-2-naphthyl)phenyl]acetamide (35), N-[2-hydroxy-4-(6-hydroxy-2-naphthyl)phenyl]benzamide (36), (E)-3-[2-hydroxy-6-(3-hydroxyphenyl)-1-naphthyl]-N-methylacrylamide (39), (E)-3-[2-hydroxy-6-(3-hydroxyphenyl)-1-naphthyl]-N-phenylacrylamide (40), 2-hydroxy-6-(3-hydroxyphenyl)-N-methyl-1-naphthamide (41), 2-hydroxy-6-(3-hydroxyphenyl)-N-phenyl-1-naphthamide (42), 2-hydroxy-N,6-bis(3-hydroxyphenyl)-1-naphthamide (43), [2-hydroxy-6-(3-hydroxyphenyl)-1-naphthyl](morpholino)methanone (44), [2-hydroxy-6-(3-hydroxyphenyl)-1-naphthyl](piperazin-1-yl)methanone (45), 2-hydroxy-6-(3-hydroxyphenyl)-N-(thiazol-2-yl)-1-naphthamide (46), N-(3,4-dimethylisoxazol-5-yl)-2-hydroxy-6-(3-hydroxyphenyl)-1-naphthamide (47), 2-hydroxy-6-(3-hydroxyphenyl)-N-(5-methyl-1,3,4-thiadiazol-2-yl)-1-naphthamide (48), 2-hydroxy-6-(3-hydroxyphenyl)-N-(pyridin-2-yl)-1-naphthamide (49), 2-hydroxy-6-(3-hydroxyphenyl)-N-(pyrimidin-2-yl)-1-naphthamide (50), [2-hydroxy-6-(3-hydroxyphenyl)-1-naphthyl](piperidin-1-yl)methanone (51), 1-bromo-6-(3-hydroxyphenyl)-2-naphthol (52), 7-hydroxy-3-(3-hydroxyphenyl)-1-naphthonitrile (53), 3-hydroxy-7-(3-hydroxyphenyl)-1-naphthonitrile (54), 3-[2-hydroxy-6-(3-hydroxyphenyl)-1-naphthyl]-N-methylpropanamide (55), 6-(3-hydroxyphenyl)-1-phenyl-2-naphthol (56), 1,6-bis(3-hydroxyphenyl)-2-naphthol (57), 1-(3-furyl)-6-(3-hydroxyphenyl)-2-naphthol (58), 6-(3-hydroxyphenyl)-1-(pyridin-3-yl)-2-naphthol (59), 6-(3-hydroxyphenyl)-1-(4-pyridyl)-2-naphthol (60), 6-(3-hydroxyphenyl)-1-(pyrimidin-5-yl)-2-naphthol (61), 6-(3-hydroxyphenyl)-1-(6-methoxy-3-pyridyl)-2-naphthol (62), 3-[2-hydroxy-6-(3-hydroxyphenyl)-1-naphthyl]benzoic acid (63), N-{3-[2-hydroxy-6-(3-hydroxyphenyl)-1-naphthyl]phenyl}methanesulfonamide (64), 6-(3-hydroxyphenyl)-1-(4-morpholinphenyl)-2-naphthol (65), N-{3-[2-hydroxy-6-(3-hydroxyphenyl)-1-naphthyl]phenyl}acetamide (66), 4-[4-(2-hydroxy-6-(3-hydroxyphenyl)-1-naphthyl]phenylamino)-4-oxobutanoic acid (67), 1-(3-aminophenyl)-6-(3-hydroxyphenyl)-2-naphthol (68), 3-[2-hydroxy-6-(3-hydroxyphenyl)-1-naphthyl]-N-(thiazol-2-yl)

benzenesulfonamide (69), 3-[2-hydroxy-6-(3-hydroxyphenyl)-1-naphthyl]-N-(5-methyl-1,3,4-thiadiazol-2-yl)benzenesulfonamide (70), 3-[2-hydroxy-6-(3-hydroxyphenyl)-1-naphthyl]-N-(1,3-thiazol-2-yl)benzamide (71), 3-[2-hydroxy-6-(3-hydroxyphenyl)-1-naphthyl]-N-(5-methyl-1,3,4-thiadiazol-2-yl)benzamide (72), N-{3-[2-hydroxy-6-(3-hydroxyphenyl)-1-naphthyl]phenyl}quinoline-8-sulfonamide (73), 5-chloro-N-{3-[2-hydroxy-6-(3-hydroxyphenyl)-1-naphthyl]phenyl}thiophene-2-sulfonamide (74), N-{3-[2-hydroxy-6-(3-hydroxyphenyl)-1-naphthyl]phenyl-3-nitrobenzenesulfonamide (75), 2-cyano-N-{3-[2-hydroxy-6-(3-hydroxyphenyl)-1-naphthyl]phenyl}benzenesulfonamide (76), 4-chloro-N-{3-[2-hydroxy-6-(3-hydroxyphenyl)-1-naphthyl]phenyl}-3-nitrobenzenesulfonamide (77), methyl 5-{3-[2-hydroxy-6-(3-hydroxyphenyl)-1-naphthyl]phenylsulfamoyl}-4-methoxythiophene-3-carboxylate (78), N-(4-{3-[2-hydroxy-6-(3-hydroxyphenyl)-1-naphthyl]phenylsulfamoyl}phenyl)acetamide (79), N-{3-[2-hydroxy-6-(3-hydroxyphenyl)-1-naphthyl]phenyl}-5-[2-(methylsulfanyl)pyrimidin-4-yl]thiophene-2-sulfonamide (80), N-{3-[2-hydroxy-6-(3-hydroxyphenyl)-1-naphthyl]phenyl}-4-nitrobenzenesulfonamide (81), 4-bromo-N-{3-[2-hydroxy-6-(3-hydroxyphenyl)-1-naphthyl]phenyl}-2-(trifluoromethoxy)-benzenesulfonamide (82), 2-nitro-N-{3-[2-hydroxy-6-(3-hydroxyphenyl)-1-naphthyl]phenyl}-4-(trifluoromethyl)benzenesulfonamide (83), N-{3-[2-hydroxy-6-(3-hydroxyphenyl)-1-naphthyl]phenyl}imidazo[2,1-b][1,3]thiazole-5-sulfonamide (84), 4,5-dibromo-N-{3-[2-hydroxy-6-(3-hydroxyphenyl)-1-naphthyl]phenyl}thiophene-2-sulfonamide (85), N-{3-[2-hydroxy-6-(3-hydroxyphenyl)-1-naphthyl]phenyl}-1,3-benzothiazole-6-sulfonamide (86), N-{3-[2-hydroxy-6-(3-hydroxyphenyl)-1-naphthyl]phenyl}thiophene-2-sulfonamide (87), 2,2,2-trifluoro-N-[2-(4-{3-[2-hydroxy-6-(3-hydroxyphenyl)-1-naphthyl]phenylsulfamoyl}phenyl)ethyl]acetamide (88), 4-bromo-2,5-difluoro-N-{3-[2-hydroxy-6-(3-hydroxyphenyl)-1-naphthyl]phenyl}benzenesulfonamide (89), 3-[2-hydroxy-6-(3-hydroxyphenyl)-1-naphthyl]-N-(methylsulfonyl)benzamide (90), 6-(3-hydroxyphenyl)-1-(phenylsulfonyl)-2-naphthol (91), 6-(3-hydroxyphenyl)-1-(4-methylphenyl)sulfonyl)-2-naphthol (92) and pharmacologically acceptable salts thereof.

7. A process for the preparation of the compound having the structure (I) according to claim 1, comprising reacting compounds (II) and (III):

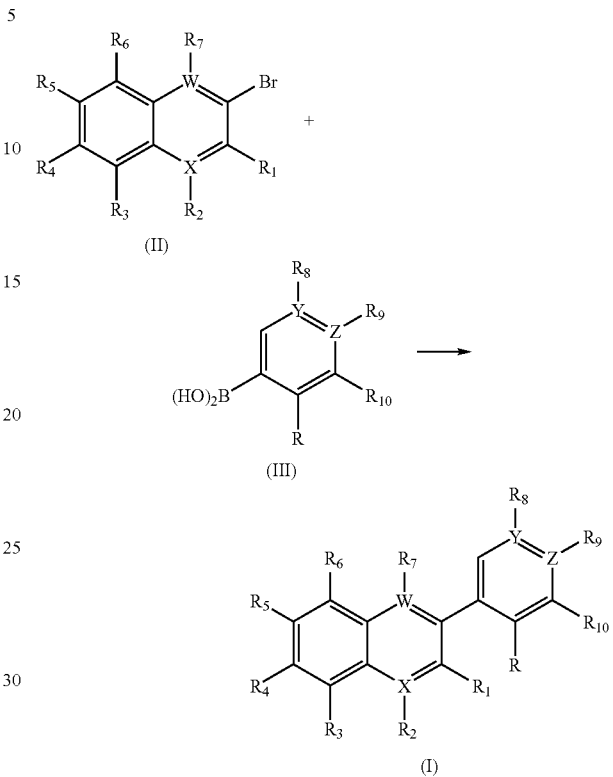

wherein W, X, Y, Z, R and $R_1$ to $R_{10}$ have the meanings as stated in claim 1 or are protected variants thereof.

8. A method for or treating a hormone-related disease selected from the group consisting of endometriosis, endometrial carcinoma, adenomyosis, breast cancer and ovarian carcinoma, said method comprising administering to a patient in need of such treatment an effective amount therefor of a compound having the structure (I) as defined in claim 1.

* * * * *

UNITED STATES PATENT AND TRADEMARK OFFICE
CERTIFICATE OF CORRECTION

| | | |
|---|---|---|
| PATENT NO. | : 8,546,392 B2 | Page 1 of 1 |
| APPLICATION NO. | : 12/593134 | |
| DATED | : October 1, 2013 | |
| INVENTOR(S) | : Hartmann et al. | |

It is certified that error appears in the above-identified patent and that said Letters Patent is hereby corrected as shown below:

IN THE SPECIFICATION

Column 32, line 38, "$C_{21}H_8O_4$" -- should read -- $C_{21}H_{18}O_4$ --.

Column 43, line 26, "$C_{21}H_8O_4$" -- should read -- $C_{21}H_{18}O_4$ --.

Column 70, line 8, "$C_{15}H_{11}NO_2$" -- should read -- $C_{15}H_{11}NO$ --.

IN THE CLAIMS

Column 114, line 38, "method for or treating" -- should read -- method for treating --.

Signed and Sealed this
Seventeenth Day of November, 2015

Michelle K. Lee
*Director of the United States Patent and Trademark Office*